US010919903B2

(12) United States Patent
Xu

(10) Patent No.: US 10,919,903 B2
(45) Date of Patent: Feb. 16, 2021

(54) NITROGEN-CONTAINING HETEROCYCLIC COMPOUNDS AS FXR MODULATORS

(71) Applicant: Hepagene Therapeutics (HK) Limited, Wan Chai (HK)

(72) Inventor: Xiaodong Xu, Doylestown, PA (US)

(73) Assignee: Hepagene Therapeutics (HK) Limited, Wan Chai (HK)

( * ) Notice: Subject to any disclaimer, the term of this patent is extended or adjusted under 35 U.S.C. 154(b) by 0 days.

(21) Appl. No.: 16/346,807

(22) PCT Filed: Oct. 27, 2017

(86) PCT No.: PCT/US2017/058802

§ 371 (c)(1),
(2) Date: May 1, 2019

(87) PCT Pub. No.: WO2018/085148

PCT Pub. Date: May 11, 2018

(65) Prior Publication Data

US 2019/0276465 A1 Sep. 12, 2019

Related U.S. Application Data

(60) Provisional application No. 62/424,813, filed on Nov. 21, 2016.

(30) Foreign Application Priority Data

Nov. 4, 2016 (CN) .......................... 2016 1 0974016

(51) Int. Cl.

| | |
|---|---|
| *C07D 487/08* | (2006.01) |
| *C07D 413/14* | (2006.01) |
| *C07D 417/14* | (2006.01) |
| *C07D 487/04* | (2006.01) |

(52) U.S. Cl.

CPC ......... *C07D 487/08* (2013.01); *C07D 413/14* (2013.01); *C07D 417/14* (2013.01); *C07D 487/04* (2013.01)

(58) Field of Classification Search

CPC .. C07D 487/04; C07D 487/08; C07D 413/14; C07D 4817/14

See application file for complete search history.

(56) References Cited

U.S. PATENT DOCUMENTS

2016/0185815 A1 6/2016 Wang et al.

FOREIGN PATENT DOCUMENTS

| | | | |
|---|---|---|---|
| WO | WO2009/012125 | | 1/2009 |
| WO | WO2009/127321 | | 10/2009 |
| WO | WO2012/087519 | | 6/2012 |
| WO | WO2012/087520 | | 6/2012 |
| WO | WO2016/097933 | | 6/2016 |
| WO | WO 2018067704 | * | 4/2018 |

OTHER PUBLICATIONS

Wang. Histology and Histopathology, 2008, 23:621-627 (Year: 2008).*

Wang. Cell Research, 2008, 18: 1087-1095 (Year: 2008).*

International Preliminary Report on Patentability and Written Opinion re Application No. PCT/US2017/058802 dated May 7, 2019; 8 pgs.

Journal of Medicinal Chemistry; Recent Progress on Bile Acid Receptor Modulators for Treatment of Metabolic Diseases; Mar. 2, 2015; 27 pgs.

* cited by examiner

*Primary Examiner* — Noble E Jarrell

(74) *Attorney, Agent, or Firm* — Foley & Lardner LLP

(57) ABSTRACT

The present technology is directed to compounds, compositions, and methods related to modulation of FXR. In particular, the present compounds and compositions may be used to treat FXR-mediated disorders and conditions, including, e.g., liver disease, hyperlipidemia, hypercholesteremia, obesity, metabolic syndrome, cardiovascular disease, gastrointestinal disease, and atherosclerosis, and renal disease.

33 Claims, No Drawings

NITROGEN-CONTAINING HETEROCYCLIC COMPOUNDS AS FXR MODULATORS

CROSS REFERENCE TO RELATED APPLICATIONS

This application is a U.S. national stage application under 35 U.S.C. § 371 of International Application No. PCT/US2017/058802, filed on Oct. 27, 2017, which claims the benefit of U.S. Provisional Application 62/424,813, filed Nov. 21, 2016, and Chinese Application 201610974016.1, filed Nov. 4, 2016, each of which is incorporated by reference in their entirety.

FIELD

The present technology is directed to compounds, compositions, and methods related to modulation of farnesoid X receptor (FXR). In particular, the present compounds and compositions may be used to treat FXR-mediated disorders and conditions, including, e.g., liver disease, hyperlipidemia, hypercholesteremia, obesity, metabolic syndrome, cardiovascular disease, gastrointestinal disease, atherosclerosis, and renal disease.

BACKGROUND

The Farnesoid X receptor (FXR, NR1H4) is an orphan member of the nuclear receptor gene family that is activated by farnesol metabolites (Forman et al. "Identification of a nuclear receptor that is activated by farnesol metabolites" *Cell* 1995, 81, 687-693; Seol et al. "Isolation of proteins that interact specifically with the retinoid X receptor: two novel orphan receptors" *Mol. Endocrinol.* 1995, 9, 72-85). FXR is highly expressed in the liver, gall bladder, intestine, kidney and adrenal glands.

Subsequently, bile acids were identified as natural ligands for FXR. Bile acid has many physiological functions and plays a critical role in the digestion, absorption, transportation, distribution of fat and lipid-soluble vitamins; maintain homeostasis of cholesterol and glucose. Through regulation of gene expression of bile acids, FXR serves as a key controller of bile acid homeostasis. Therefore, FXR modulation is expected to provide treatments for diseases such as cholestasis, liver fibrosis, liver cancer, atherosclerosis, diabetes and the like. FXR agonists were also reported as a treatment option for HBV infection (Radreau et al. "Reciprocal regulation of farnesoid X receptor a activity and hepatitis B virus replication in differentiated HepaRG cells and primary human hepatocytes" *FASEB J,* 2016, 30, 3146-3154).

In recent years, a variety of primary and secondary bile acids such as chenodeoxycholic acid (CDCA) that can activate FXR have been found. In 2002, Pellicciari et al. reported the first synthesis of highly active steroid FXR agonist, 6-ethyl-CDCA (Pellicciari et al. "6α-ethyl-chenodeoxycholic acid (6-ECDCA), a potent and selective FXR agonist endowed with anticholestatic activity" *J. Med. Chem.* 2002, 45, 3569-72). 6-EDCA, also known as obeticholic acid, is in clinical trials for treatment of NAFLD, NASH, liver cirrhosis and other liver conditions. It has been approved for treatment in the US for the treatment of primary biliary cholangitis. Thus, FXR modulators have been shown to be therapeutically effective in a number of FXR-mediated diseases and disorders.

SUMMARY

In one aspect, the present technology provides a compound according to formula I (I)

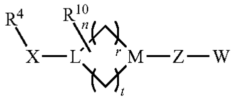

stereoisomers, and/or salts thereof, wherein

L and M are independently selected from N and $CR^7$, provided that at least one of L and M is N;

Z is a substituted or unsubstituted $C_1$-$C_4$ alkylene, O—$C_1$-$C_4$ alkylene, cyclopropylalkylene, or oxetanylalkylene group;

W is

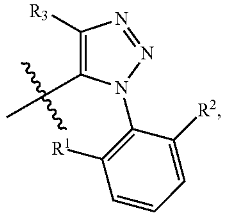

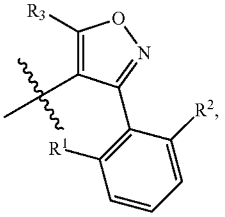

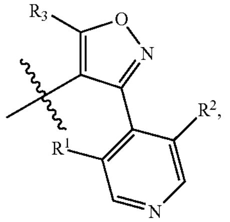

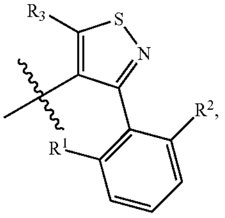

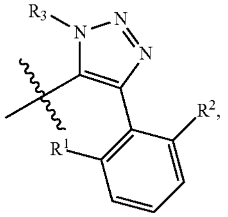

or

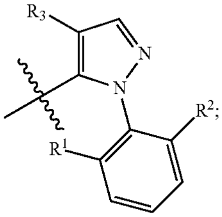

X is

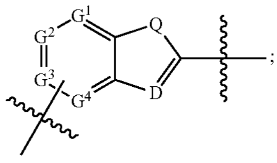

D is N or $CR^9$;

one of $G^1$, $G^2$, $G^3$, and $G^4$ is $CR^{13}$ and the others are selected from the group consisting of CH and $CR^{11}$;

Q is O, S, or $NR^{12}$;

$R^1$ and $R^2$ are independently H, OH, halo, CN, carboxyl, $NR^aR^b$, or a substituted or unsubstituted alkyl, alkoxy, or hydroxyalkyl group;

$R^3$ is a substituted or unsubstituted alkyl or cycloalkyl group;

$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;

$R^7$ is H, OH, halo, CN, carboxyl, amido, $NR^aR^b$, or a substituted or unsubstituted alkyl, alkoxy, hydroxyalkyl, or aminoalkyl group;

$R^9$ and $R^{13}$ are independently H, halo, or a substituted or unsubstituted $C_1$-$C_6$ alkyl, or O—($C_1$-$C_6$ alkyl) group;

$R^{10}$ at each occurrence is independently halo, $CO_2R$, or a substituted or unsubstituted alkyl, alkoxy, hydroxyalkyl, cycloalkyl, or fluorinated cycloalkyl group, or, when n is 2 or 3, two of the $R^{10}$ groups together may be a substituted or unsubstituted $C_2$-$C_5$ alkylene, heteroalkylene, alkenylene or heteroalkenylene group having 2 separate points of attachment to the same carbon or different carbons of the nitrogen containing ring to which it is attached;

$R^{11}$ at each occurrence are independently OH, halo, $CF_3$, CN, carboxyl, $NR^aR^b$, or a substituted or unsubstituted alkyl, alkoxy group, or phenyl group;

$R^{12}$ is H or a substituted or unsubstituted $C_1$-$C_6$ alkyl group; and $R^a$ at each occurrence is independently H, or a substituted or unsubstituted alkyl, haloalkyl, cycloalkyl, aryl, or $SO_2$-alkyl group;

$R^b$ at each occurrence is H or a substituted or unsubstituted alkyl, or haloalkyl group;

$R^c$ is H or a substituted or unsubstituted alkyl, alkenyl, alkynyl, or cycloalkyl group;

n is 0, 1, 2, 3, or 4; and r and t are each independently 1, 2, or 3.

In a second aspect, the present technology provides a compound according to formula IA, IB, or IC:

(IA)

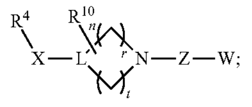

(IB)

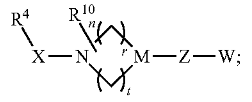

(IC)

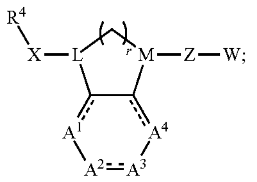

stereoisomers, and/or salts thereof; wherein $A^1$, $A^2$, $A^3$, and $A^4$ are independently selected from the group consisting of $CR^5R^6$ and $NR^8$, or when involved in a double bond, are selected from the group consisting of $CR^5$ and N, provided that not more than two of A, $A^2$, $A^3$, and $A^4$ are N or $NR^8$;

L and M are independently N or $CR^7$;

Z is a substituted or unsubstituted $C_1$-$C_4$ alkylene, O—$C_1$-$C_4$ alkylene, cyclopropylalkylene, or oxetanylalkylene group;

W is

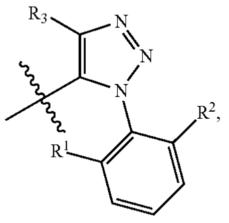

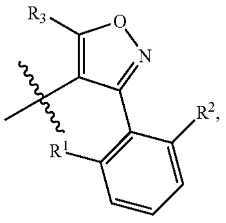

-continued

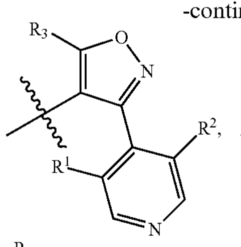

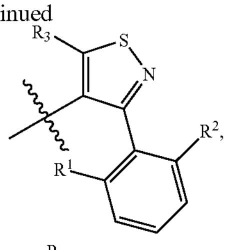

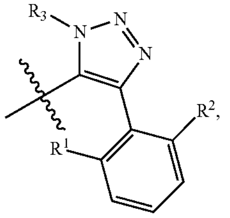

or

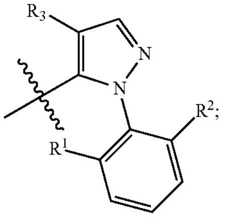

X is

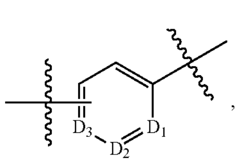

,

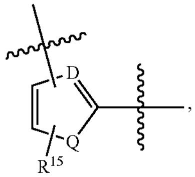

, or

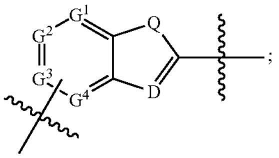

D is N or $CR^9$;

$D^1$, $D^2$ and $D^3$ are independently selected from CH or $CR^{14}$, and optionally one of $D^1$, $D^2$ and $D^3$ is N;

one of $G^1$, $G^2$, $G^3$, and $G^4$ is $CR^{13}$ and the others are selected from the group consisting of CH, $CR^{11}$, and N, provided that not more than one of $G^1$, $G^2$, $G^3$, and $G^4$ is N;

Q is O, S, or NR12;

$R^1$ and $R^2$ are independently H, OH, halo, CN, carboxyl, $NR^aR^b$, or a substituted or unsubstituted alkyl, alkoxy, or hydroxyalkyl group;

$R^3$ is a substituted or unsubstituted alkyl or cycloalkyl group;

$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;

$R^5$ and $R^7$ are independently H, OH, halo, CN, carboxyl, amido, $NR^aR^b$, or a substituted or unsubstituted alkyl, alkoxy, hydroxyalkyl, or aminoalkyl group;

$R^6$ at each occurrence is independently H, OH, halo, CN, carboxyl, amido, $NR^aR^b$, or a substituted or unsubstituted alkyl, alkoxy, hydroxyalkyl, or aminoalkyl group;

$R^8$ at each occurrence is independently H or a substituted or unsubstituted alkyl group;

$R^9$ and $R^{13}$ are independently H, halo, or a substituted or unsubstituted $C_1$-$C_6$ alkyl, or O—($C_1$-$C_6$ alkyl) group;

$R^{10}$ at each occurrence is independently halo, $CO_2R^c$, or a substituted or unsubstituted alkyl, alkoxy, hydroxyalkyl, cycloalkyl, or fluorinated cycloalkyl group;

$R^{11}$ and $R^{14}$ at each occurrence are independently OH, halo, $CF_3$, CN, carboxyl, $NR^aR^b$, or a substituted or unsubstituted alkyl, alkoxy group, or phenyl group;

$R^{12}$ is H or a substituted or unsubstituted $C_1$-$C_6$ alkyl group; and $R^a$ at each occurrence is independently H, or a substituted or unsubstituted alkyl, haloalkyl, cycloalkyl, aryl, or $SO_2$-alkyl group;

$R^b$ at each occurrence is H or a substituted or unsubstituted alkyl, or haloalkyl group;

$R^c$ is H or a substituted or unsubstituted alkyl, alkenyl, alkynyl, or cycloalkyl group;

n is 0, 1, 2, 3, or 4;

r and t are each independently 1, 2, or 3; and

------ indicates a single or double bond.

In a related aspect, a composition is provided that includes the compound of any one of the compounds disclosed herein (including but not limited to compounds of formulae I, IA, IB, and IC) and a pharmaceutically accepT carrier.

In another aspect, a pharmaceutical composition is provided, the pharmaceutical composition including an effective amount of the compound of any one of the above embodiments for treating an FXR-mediated disorder or condition.

In another aspect, a method is provided that includes administering an effective amount of a compound of any one of the above embodiments, or administering a pharmaceutical composition including an effective amount of a compound of any one of the above embodiments, to a subject suffering from an FXR-mediated disorder or condition.

In another aspect, a method is provided that includes modulating FXR in a subject by contacting FXR with an effective amount of a compound of any one of the compounds of described herein, including but not limited to compounds of formulae I, IA, IB, and IC.

DETAILED DESCRIPTION

In various aspects, the present technology provides compounds and methods for modulating FXR and the treatment of FXR-mediated disorders and conditions. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); $CF_3$; hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., SFs), sulfonamides; amines; N-oxides; hydrazines; hydrazides; hydrazones; azides; amides; amines; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $-C{\equiv}CH$, $-C{\equiv}CCH_3$, $-CH_2C{\equiv}CCH_3$, $-C{\equiv}CCH_2CH(CH_2CH_3)_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heteroalkyl groups are alkyl groups in which 1 or 2 carbons are replaced with a heteroatom selected from N, O or S. Thus, heteroalkyl groups may include straight chain and branched chain heteroalkyl groups having from 1 to 11 carbon atoms, and typically from 1 to 10 carbons or, in some embodiments, from 1 to 8, 1 to 6, or 1 to 4 carbon atoms. Heteroalkyl groups include for example, methoxy, methoxyethyl, methylthio, methylthiopropyl, ethyloxymethyl, and methylaminobutyl. Heteroalkyl groups may be substituted one or more times just as alkyl groups are with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, oxadiazolonyl (including 1,2,4-oxazol-5(4H)-one-3-yl), isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups; divalent aryl groups are arylene groups; divalent heteroalkyl groups are heteroalkylene groups; heteroaryl groups are divalent heteroarylene groups; and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to $—COOR^{70}$ and —C(O)O-G groups. $R^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., $—C(O)NR^{71}R^{72}$, and $—NR^{71}C(O)R^{72}$ groups, respectively. $R^{71}$ and $R^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups ($—C(O)NH_2$) and formamide groups (—NHC(O)H). In some embodiments, the amide is $—NR^{71}C(O)—(C_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., $—NR^{73}C(O)OR^{74}$ and $—OC(O)NR^{73}R^{74}$ groups, respectively. $R^{73}$ and $R^{74}$ are independently a substituted or unsubstituted alkyl, alkenyl, alkynyl, cycloalkyl, aryl, aralkyl, heterocyclylalkyl, or heterocyclyl group as defined herein. $R^{73}$ may also be H.

The term "amine" (or "amino") as used herein refers to $—NR^{75}R^{76}$ groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "sulfonamido" includes S- and N-sulfonamide groups, i.e., $—SO_2NR^{78}R^{79}$ and $—NR^{78}SO_2R^{79}$ groups, respectively. $R^{78}$ and $R^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups ($—SO_2NH_2$). In some embodiments herein, the sulfonamido is $—NHSO_2$-alkyl and is referred to as the "alkylsulfonylamino" group.

The term "thiol" refers to —SH groups, while "sulfides" include $—SR^{80}$ groups, "sulfoxides" include $—S(O)R^{81}$ groups, "sulfones" include $—SO_2R^{82}$ groups, and "sulfonyls" include $—SO_2OR^{83}$. $R^{80}$, $R^{81}$, $R^{82}$, and $R^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to $—NR^{84}—C(O)—NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to $—C(NR^{87})NR^{88}R^{89}$ and $—NR^{87}C(NR^{88})R^{89}$, wherein $R^{87}$, $R^{88}$, and $R^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to $—NR^{90}C(NR^{91})NR^{92}R^{93}$, wherein $R^{90}$, $R^{91}$, $R^{92}$ and $R^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to $—C(R^{94})═C(R^{95})NR^{96}R^{97}$ and $—NR^{94}C(R^{95})═C(R^{96})R^{97}$, wherein $R^{94}$, $R^{95}$, $R^{96}$ and $R^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—. A "hydroxyalkyl" group is a hydroxyl-substituted alkyl group, such as $HO—CH_2—$.

The term "imide" refers to $—C(O)NR^{98}C(O)R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to $—CR^{100}(NR^{101})$ and $—N(CR^{100}R^{101})$ groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an $—NO_2$ group.

The term "trifluoromethyl" as used herein refers to $—CF_3$.

The term "trifluoromethoxy" as used herein refers to $—OCF_3$.

The term "azido" refers to $—N_3$.

The term "trialkyl ammonium" refers to a $—N(alkyl)_3$ group. A trialkylammonium group is positively charged and thus typically has an associated anion, such as halogen anion.

The term "isocyano" refers to —NC.

The term "isothiocyano" refers to —NCS.

The phrase "selectively modulates" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular receptor over other receptors, such as an FXR over a GR receptor, LXR, PPARγ, TGR5 or PXR. This phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

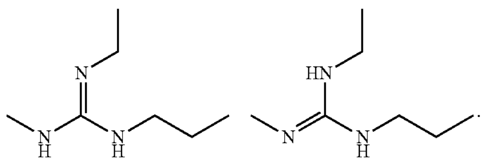

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In one aspect, the present technology provides heterocyclic derivatives such as pyrrolidines, imidazolidines, piperidines, piperazines, azepanes and diazepanes that modulate FXR and intermediates for making such compounds. The compounds include, but are not limited to compounds of formulae I, IA, IB, and IC as described herein.

In some aspects or embodiments of compounds of the present technology, compounds of formula IA are provided:

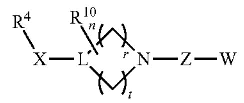

(IA)

wherein X, L, Z, W, $R^4$, $R^{10}$, n, r, and t may have any of the values of any of the aspects or embodiments of compounds described herein. In certain such embodiments, L is N. In other embodiments, L is $CR^7$.

In some aspects or embodiments of compounds of the present technology, compounds of formula IB are provided:

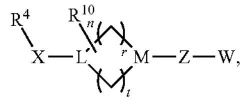

(IB)

wherein X, M, Z, W, $R^4$, $R^{10}$, n, r, and t may have any of the values of any of the aspects or embodiments of compounds described herein. In certain embodiments of compounds of formula IB, M is N. In other embodiments, M is $CR^7$.

In some aspects and embodiments of the present compounds (including but not limited to compounds of formulae I, IA, IB, and IC), r and t are each independently 1, 2, or 3, as noted above. In certain embodiments, r is 1 or 2. In some embodiments, r is 2. In some embodiments, t is 1. In other embodiments t is 2. In some embodiments t is 3. In some embodiments, the sum of r+t is greater than 2 but less than 6 (i.e., 2<r+t<6). Thus, in some embodiments the present compounds include but are not limited to pyrrolidines, piperidines, piperazines, azepanes and diazepanes. For example, in some embodiments compounds of formula I include, but are not limited to, compounds of formulas IA1 (r=1, t=2, L=CH), IA2 (r=2, t=2, L=CH), IA3 (r=2, t=2, L=N), IA4 (r=2, t=3, L=CH), and IA5 (r=2, t=3, L=N), below. In other embodiments, compounds of formula I include but are not limited to compounds of formulas IB1 (r=1, t=2, M=CH), IB2 (r=1, t=2, M=N), IB3 (r=2, t=2, M=CH), and IB4 (r=2, t=3, M=CH), below.

IA1

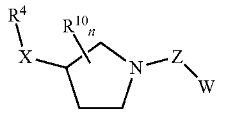

IA2

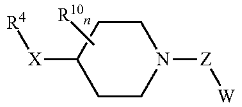

IA3

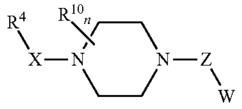

-continued

IA4

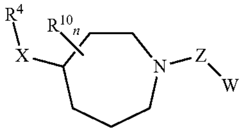

IA5

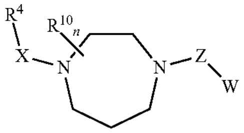

IB1

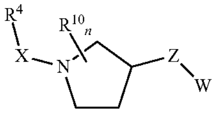

IB2

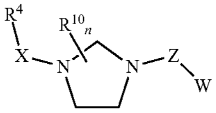

IB3

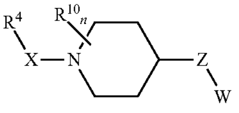

IB4

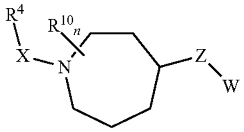

In some embodiments, n is 1 or 2. In some embodiments, n is 0. In some embodiments, $R^{10}$ at each occurrence is independently halo, $CO_2R^c$, or a substituted or unsubstituted alkyl, alkoxy, hydroxyalkyl, cycloalkyl, or fluorinated cycloalkyl group. For example, in some embodiments, $R^{10}$ at each occurrence is independently $CO_2H$, substituted or unsubstituted $C_1$-$C_3$ alkyl, $C_1$-$C_3$ hydroxyalkyl, or $C_3$-$C_6$ cycloalkyl group. In some embodiments, $R^{10}$ at each occurrence is independently $CO_2H$, $CH_3$, $CH_2OH$, or a cyclopropyl group. In other embodiments, $R^{10}$ at each occurrence is independently $CH_3$, $CH_2CH_3$, or $CH(CH_3)_2$. In certain embodiments, when n is 2 or 3, two of the $R^{10}$ groups together may be a substituted or unsubstituted $C_2$-$C_5$ (i.e., a C2, C3, C4, or C5 alkylene group) alkylene, heteroalkylene, alkenylene or heteroalkenylene group having 2 separate points of attachment to the same carbon or different carbons of the nitrogen containing ring to which it is attached. In some such embodiments, $R^{10}$ may be a substituted or unsubstituted C2-C5 alkylene group having 2 separate points of attachment to the same carbon or different carbons of the nitrogen containing ring to which it is attached. In some such embodiments, $R^{10}$ is an unsubstituted C2-C5 alkylene group having 2 separate points of attachment to the same carbon, thus forming a spirocyclic group (e.g., a spirocyclic cyclopropyl group, spirocyclic cyclobutyl group, spirocyclic cyclopentyl group, spirocyclic cyclohexyl group). In some embodiments, $R^{10}$ is an unsubstituted C2, C3, C4 or C5 alkylene group having 2 separate points of attachment to different carbons, thus forming fused bicyclic rings, e.g., octahydroquinoxaline, 3,8-diazabicyclo[3.2.1]octane, and 3,9-diazabicyclo[3.3.1]nonane. Thus, in some embodiments, the compounds of formula I have the formulae IIA, IIB and IIC:

(IIA)

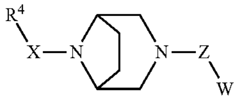

(IIB)

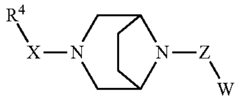

(IIC)

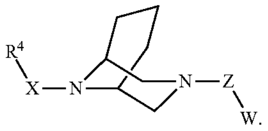

In some embodiments of the present compounds, $R^4$ is $CO_2H$, CN, $CONH_2$, $SO_2NH_2$, or a substituted or unsubstituted $CO_2$—$C_1$-$C_6$ alkyl, $CO_2$—$C_3$-$C_6$ cycloalkyl, CONH—$C_1$-$C_6$ alkyl, CONH—$C_3$-$C_6$ cycloalkyl, NH—$SO_2$—$C_1$-$C_6$ alkyl, or tetrazolyl group. In some embodiments, $R^4$ is $CO_2H$, CN, $CONH_2$, or a substituted or unsubstituted $CO_2$—$C_1$-$C_6$ alkyl, CONH—$C_1$-$C_6$ alkyl, or tetrazolyl group. In yet other embodiments, $R^4$ is $CO_2H$, or an unsubstituted $CO_2$—$C_1$-$C_6$ alkyl, $CONH_2$, or tetrazolyl group. In some embodiments, $R^4$ is $CO_2H$.

In the present compounds, X may be

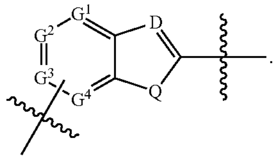

It will be understood that as depicted, X is attached to $R^4$ via the open valence on the left side of the structure, and X is attached to the central nitrogen-containing heterocycle via the open valence on the right side of the structure.

In some embodiments, one of $G^1$, $G^2$, $G^3$, and $G^4$ is $CR^{13}$ and the others are CH (it being understood that $R^4$ is attached in place of H at one of the G variables defined as CH). In other embodiments, one of $G^1$, $G^2$, $G^3$, and $G^4$ is $CR^{13}$ and one is $CR^{11}$. In some embodiments, D is N and in others, D is $CR^9$. In some embodiments, Q is S. In others, Q is 0, and in still others, Q is $NR^{12}$. In some embodiments, D is N and Q is S. In others, D is N and Q is $NR^{12}$. In some embodiments D is $CR^9$ and Q is S, or D is $CR^9$ and Q is $NR^{12}$.

Thus, in some embodiments, X is

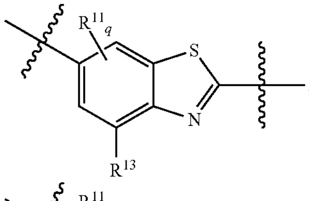

,

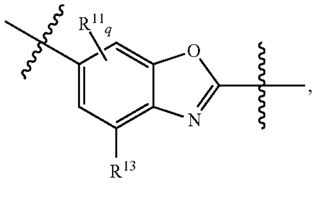

,

-continued

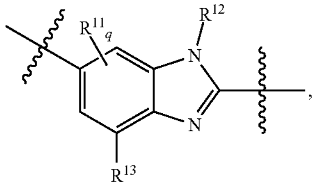

,

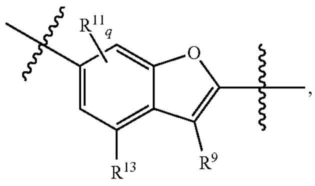

,

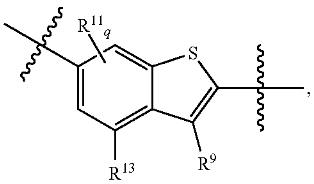

, or

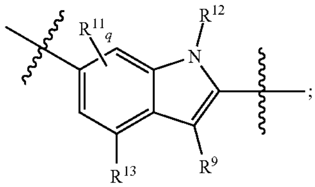

;

wherein q is 0, 1, or 2. In some such embodiments, q is 0. In other embodiments, q is 1. In the foregoing embodiments of X, $R^9$, $R^{11}$, $R^{12}$ and $R^{13}$ may have any of the values described herein for compounds of the present technology.

In some embodiments of the present compounds, $R^9$ and $R^{13}$ are independently H, halo, or a substituted or unsubstituted $C_1$-$C_4$ alkyl, or O—($C_1$-$C_4$ alkyl) group. In some embodiments, $R^9$ is H, F, or Cl. In some embodiments, $R^{13}$ is H, F, or a substituted or unsubstituted $C_1$-$C_3$ alkyl, or O—($C_1$-$C_3$ alkyl) group. In some embodiments, $R^{13}$ is H, F, $CH_3$, or $OCH_3$. In some embodiments, $R^9$ is H.

In some embodiments, $R^{11}$ at each occurrence is independently halo, $CF_3$, or a substituted or unsubstituted alkyl or alkoxy group. In certain embodiments, $R^{11}$ is F, Cl, or $CF_3$. In some embodiments, $R^{12}$ is H or a substituted or unsubstituted $C_1$-$C_6$ alkyl group. In some embodiments, $R^{12}$ is H or $CH_3$.

In some embodiments, Z is a substituted or unsubstituted $C_1$-$C_4$ alkylene or O—$C_1$-$C_4$ alkylene group. In some embodiments, Z is a substituted or unsubstituted $C_1$-$C_2$ alkylene or O—$C_1$-$C_2$ alkylene group. In some embodiments, Z is a substituted or unsubstituted $C_1$-$C_4$ alkylene group. In some embodiments, Z is a substituted or unsubstituted $C_1$-$C_2$ alkylene group. In some embodiments, Z is a substituted or unsubstituted methylene, e.g., —$CH_2$—. In some embodiments, Z is a substituted or unsubstituted cyclopropylalkylene group. In some embodiments, Z may be substituted with halo or OH. In some embodiments, Z may be substituted with F or OH. In some embodiments, Z may be substituted with F, OH, or $CF_3$.

In some embodiments, W is

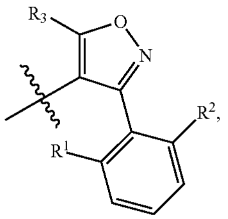

,

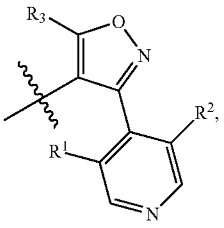

, or

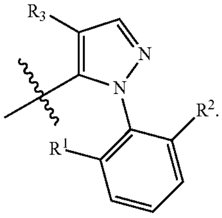

.

In some embodiments of the present compounds, $R^1$ and $R^2$ are independently halo, CN, $CO_2R^e$, $NR^eR^f$, or a substituted or unsubstituted $C_1$-$C_6$ alkyl, $C_1$-$C_6$ alkoxy, or $C_1$-$C_6$ hydroxyalkyl group; and wherein $R^e$ and $R^f$ at each occurrence are independently H or a substituted or unsubstituted $C_1$-$C_6$ alkyl group. In some embodiments, $R^1$ and $R^2$ are independently H, F, Cl, CN, $CO_2H$, $NR^eR^f$, or a substituted or unsubstituted $C_1$-$C_3$ alkyl, $C_1$-$C_3$ alkoxy, or $C_1$-$C_3$ hydroxyalkyl group. In some embodiments, $R^1$ and $R^2$ are independently H, F, Cl, CN, $CO_2H$, $NH_2$, $CH_3$, $CH_2NH_2$, $OCF_3$, or $OCH_3$. In some embodiments, $R^1$ and $R^2$ are both Cl. In some embodiments, one of $R^1$ and $R^2$ is H and the other is $OCF_3$.

In some embodiments, $R^3$ is a substituted or unsubstituted $C_1$-$C_6$ alkyl or $C_3$-$C_6$ cycloalkyl group. In some embodiments, $R^3$ is $CH_3$, $CH_2CH_3$, $CH(CH_3)_2$, $CH_2CH(CH_3)_2$, $CH(CH_2CH_3)_2$, $CH(CH_2CH_3)(CH_3)$, $C(CH_3)_3$, or cyclopropyl. In some embodiments, $R^3$ is an isopropyl or cyclopropyl group.

In a third aspect, the present technology provides a compound according to formula IA, IB, or IC:

(IA)

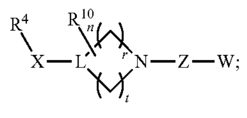

(IB)

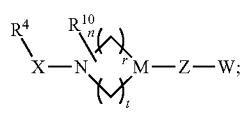

stereoisomers, and/or salts thereof; wherein

L and M are independently N or $CR^7$;

Z is a substituted or unsubstituted $C_1$-$C_4$ alkylene, O—$C_1$-$C_4$ alkylene, cyclopropylalkylene, or oxetanylalkylene group;

W is

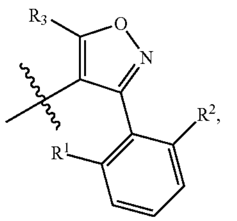

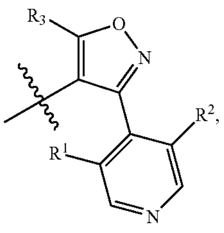

or

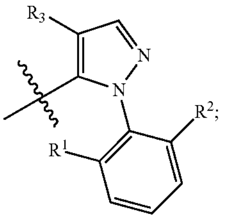

X is

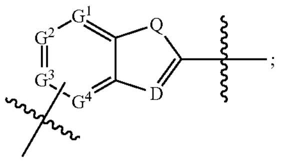

D is N or $CR^9$;

one of $G^1$, $G^2$, $G^3$, and $G^4$ is $CR^{13}$ and the others are selected from the group consisting of CH and $CR^{11}$;

Q is O, S, or $NR^{12}$;

$R^1$ and $R^2$ are independently H, OH, halo, CN, carboxyl, $NR^aR^b$, or a substituted or unsubstituted alkyl, alkoxy, or hydroxyalkyl group;

$R^3$ is a substituted or unsubstituted alkyl or cycloalkyl group;

$R^4$ is $SO_3H$, $CONR^aR^b$, $SO_2NR^aR^b$, $NHSO_2R^b$, $SO_2NHCOR^a$, $CO_2R^c$, or an unsubstituted tetrazolyl group;

$R^7$ is H, OH, halo, CN, carboxyl, amido, $NR^aR^b$, or a substituted or unsubstituted alkyl, alkoxy, hydroxyalkyl, or aminoalkyl group;

$R^9$ and $R^{13}$ are independently H, halo, or a substituted or unsubstituted $C_1$-$C_6$ alkyl, or O—($C_1$-$C_6$ alkyl) group;

$R^{10}$ at each occurrence is independently halo, $CO_2R^c$, or a substituted or unsubstituted alkyl, alkoxy, hydroxyalkyl, cycloalkyl, or fluorinated cycloalkyl group, or, when n is 2 or 3, two of the $R^{10}$ groups together may be a substituted or unsubstituted C2-C5 alkylene or alkenylene group having 2 separate points of attachment to the same carbon or different carbons of the nitrogen containing ring to which it is attached;

$R^{11}$ is OH, halo, $CF_3$, CN, carboxyl, $NR^aR^b$, or a substituted or unsubstituted alkyl or alkoxy group;

$R^{12}$ is H or a substituted or unsubstituted $C_1$-$C_6$ alkyl group; and $R^a$ at each occurrence is independently H, or a substituted or unsubstituted alkyl, haloalkyl, cycloalkyl, aryl, or $SO_2$-alkyl group;

$R^b$ at each occurrence is H or a substituted or unsubstituted alkyl, or haloalkyl group;

$R^c$ is H or a substituted or unsubstituted alkyl, alkenyl, or cycloalkyl group;

n is 0, 1, 2, 3, or 4; and r and t are each independently 1, 2, or 3.

In an aspect of the present technology, a composition is provided that includes any one of the aspects and embodiments of compounds of formulas I-III and a pharmaceutically acceptable carrier. In a related aspect, a pharmaceutical composition is provided which includes an effective amount of the compound of any one of the aspects and embodiments of compounds of formulas I-IV for treating an FXR-mediated disorder or condition. The FXR-mediated disorder or condition may be liver disease, hyperlipidemia, hypercholesteremia, obesity, metabolic syndrome, cardiovascular disease, gastrointestinal disease, atherosclerosis, or renal disease. For example, the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

In a further related aspect, a method is provided that includes administering an effective amount of a compound of any one of the aspects and embodiments of compounds of formulas I-IV or administering a pharmaceutical composition comprising an effective amount of a compound of any one of the aspects and embodiments of compounds of formula I-IV to a subject suffering from an FXR-mediated disorder or condition. The FXR-mediated disorder or condition may be liver disease, hyperlipidemia, hypercholesteremia, obesity, metabolic syndrome, cardiovascular disease, gastrointestinal disease, atherosclerosis, or renal disease. In some embodiments, the disorder or condition is the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of hyperlipidemia. Another example of an effective amount includes amounts or dosages that are capable of reducing symptoms associated with metabolic syndrome, such as, for example, obesity and/or metabolic syndrome. The effective amount of the compound may selectively modulate FXR. As used herein, a "subject" or "patient" is a mammal, such as a cat, dog, rodent or primate. Typically the subject is a human, and, preferably, a human suffering from or suspected of suffering from an FXR-mediated disorder or condition. The term "subject" and "patient" can be used interchangeably.

In still another aspect, the present technology provides methods of modulating FXR by contacting FXR with an effective amount of any compound as described herein, including but not limited to a compound of formula I, II, III, or IV.

Thus, the instant present technology provides pharmaceutical compositions and medicaments comprising any of the compounds disclosed herein (e.g., compounds of formulas I-IV) and a pharmaceutically acceptable carrier or one or more excipients or fillers. The compositions may be used in the methods and treatments described herein. Such compositions and medicaments include a therapeutically effective amount of any compound as described herein, including but not limited to a compound of formula I, II, III, or IV. The pharmaceutical composition may be packaged in unit dosage form.

The pharmaceutical compositions and medicaments may be prepared by mixing one or more compounds of the present technology, stereoisomers thereof, and/or pharmaceutically acceptable salts thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with or mediated by FXR, including but not limited to liver disease, hyperlipidemia, hypercholesteremia, obesity, metabolic syndrome, cardiovascular disease, gastrointestinal disease, atherosclerosis and renal disease. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until for example, (for metabolic syndrome and/or obesity) the elevated plasma or elevated white blood cell count or hepatic cholesterol or triglycerides or progression of the disease state is reduced or stopped. For metabolic syndrome and/or obesity, the progression of the disease state can be assessed using in vivo imaging, as described, or by taking a tissue sample from a patient and observing the target of interest therein.

The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of hyperlipidemia, such as, for example, a decrease in triglycerides in the blood stream. Effectiveness of the compositions and methods of the present technology may also be demonstrated by a decrease in the signs and symptoms of liver disease, hyperlipidemia, hypercholesteremia, obesity, metabolic syndrome, cardiovascular disease, gastrointestinal disease, atherosclerosis, or renal disease.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of liver disease, hyperlipidemia, hypercholesteremia, obesity, metabolic syndrome, cardiovascular disease, gastrointestinal disease, atherosclerosis, or renal disease. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially be effective for the treatment of liver disease, hyperlipidemia, hypercholesteremia, obesity, metabolic syndrome, cardiovascular disease, gastrointestinal disease, atherosclerosis, or renal disease.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a KOR. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

List of Abbreviations

ACN acetonitrile
t-Bu tert-butyl
DCM dichloromethane
DIAD diisopropyl azodicarboxylate
DMF dimethylformamide
DMA dimethylacetamide
DMAP 4-dimethylaminopyridine
DMP tert-2,2-dimethoxypropane
DMSO dimethyl sulfoxide
Et ethyl
HATU (1-[bis(dimethylamino)methylene]-1H-1,2,3-triazolo[4,5-b]pyridinium 3-oxid hexafluorophosphate)
LAH lithium aluminum hydride
Me methyl
MeCN acetonitrile
NCS N-chlorosuccinimide
PCC pyridinium chlorochromate
PE petroleum ether
Ph phenyl
STAB sodium triacetoxyborohydride
TEA triethylamine
TFA trifluoroacetic acid
TFAA trifluoroacetic anhydride
THF tetrahydrofuran
TLC thin layer chromatography
TMS trimethylsilyl
TsOH p-toluenesulfonic acid

Common Intermediates Synthetic Schemes

Scheme 1 (Compound INT-001)

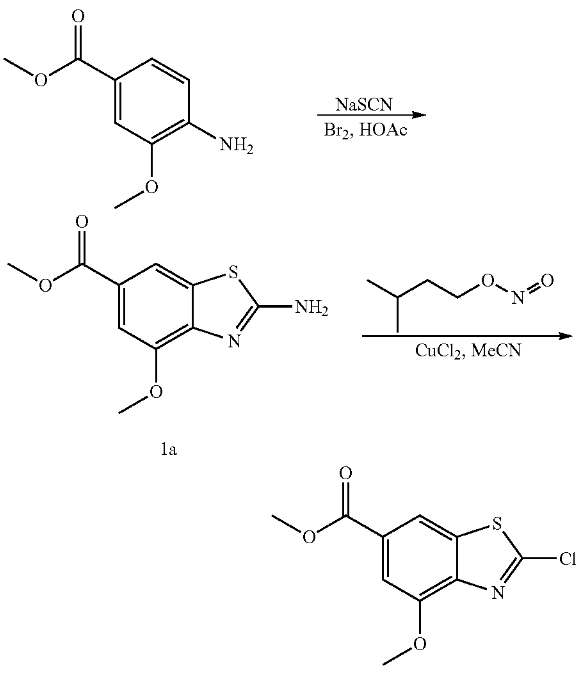

1a

INT-001

Experimental Details for INT-001 (Scheme 1)

Methyl 2-amino-4-methoxybenzo[d]thiazole-6-carboxylate (Compound 1a)

To a solution of methyl 4-amino-3-methoxybenzoate (20 g, 110 mmol) in acetic acid (340 mL) was added NaSCN (35.8 g, 330 mmol) and $Br_2$ (26.2 g, 165 mmol) sequentially. The mixture was stirred overnight at room temperature. The mixture was concentrated under vacuum. The residue was suspended in 100 mL of water. The pH value of the mixture was adjusted to 8 with NaOH (2 M). The solids were collected and dried under vacuum. This resulted in 22.5 g of the title compound as a yellow solid (crude product). LC-MS (ESI, m/z): $[M+H]^+$=239.1.

Methyl 2-chloro-4-methoxybenzo[d]thiazole-6-carboxylate (Compound INT-001)

To a suspension of Compound 1a (22.5 g, 94 mmol) in MeCN (320 mL) was added $CuCl_2$ (25 g, 188 mmol). The mixture was stirred for 5 min at room temperature before 3-methylbutyl nitrite (16.5 g, 141 mmol) was added dropwise at room temperature. The reaction was stirred for another 1 h at 60° C. The reaction was then quenched by the addition of 60 mL of water. The resulting mixture was extracted with ethyl acetate several times. The organic layers were combined. The organic phase was washed with water and brine. The residue was concentrated under vacuum after dried over anhydrous sodium sulfate. The residue was applied onto a silica gel column with ethyl acetate/petroleum ether (1:5). This resulted in 13 g (54%) of the title compound as a yellow solid. LC-MS (ESI, m/z): $[M+H]^+=258.2$.

Following the procedure described above for Scheme 1 and substituting the appropriate reagents, starting materials and purification methods known to those skilled in the art, the following common intermediates were prepared as shown in Table 1.

TABLE 1

| Compound | Structure | LC-MS $(M + H)^+$ |
| --- | --- | --- |
| INT-002 | 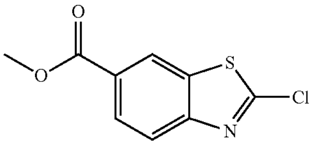 | 228.0 |
| INT-003 | 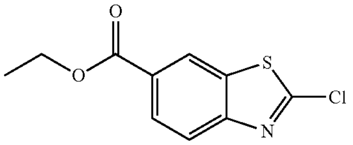 | 242.3 |
| INT-004 | 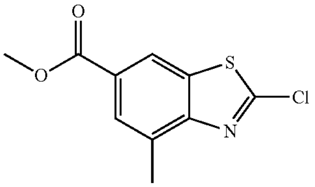 | 242.0 |
| INT-005 | 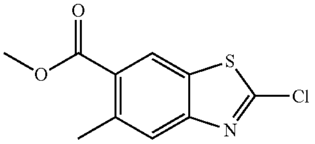 | 242.3 |
| INT-006 | 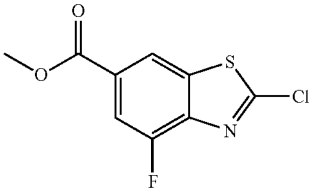 | 246.0 |
| INT-007 | 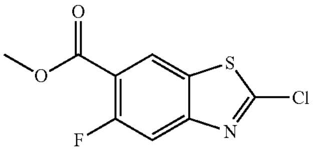 | 246.3 |

TABLE 1-continued

| Compound | Structure | LC-MS $(M + H)^+$ |
| --- | --- | --- |
| INT-008 | 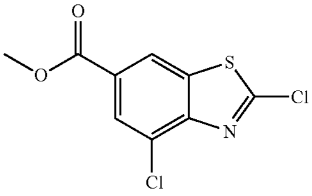 | 262.1 |

Scheme 2 (INT-011)

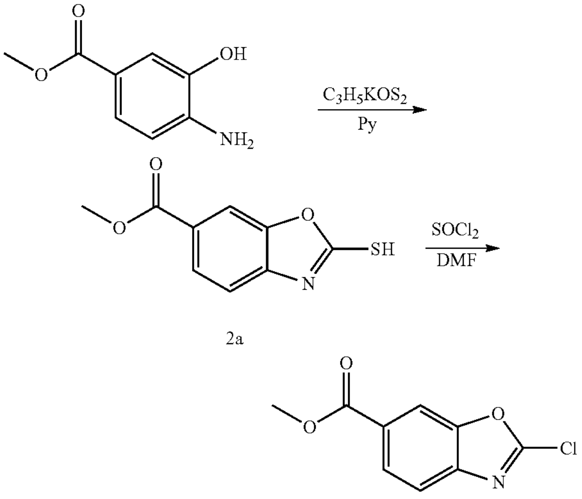

2a

INT-011

Experimental Details for INT-011 (Scheme 2)

Methyl 2-mercaptobenzo[d]oxazole-6-carboxylate (Compound 2a)

To a stirring solution of methyl 4-amino-3-hydroxybenzoate (5 g, 29.91 mmol) in pyridine (60 mL) was added ethoxy(potassiosulfanyl)methanethione (5 g, 31.19 mmol). The resulting solution was stirred for 5 h at 115° C. The reaction was quenched with water. The resulting solution was extracted with 3×30 mL of dichloromethane. The organic layers were combined and washed successively with water and brine. The residue was concentrated under vacuum after dried over anhydrous sodium sulfate. This resulted in 3.5 g (56%) of the title compound as a yellow solid.

Methyl 2-chlorobenzo[d]oxazole-6-carboxylate (Compound INT-011)

To a suspension of Compound 2a (1 g, 4.78 mmol) in thionyl dichloride (5 mL) was added DMF (0.1 mL). The resulting solution was stirred for 15 min at 80° C. The reaction solution was concentrated under vacuum. The crude was diluted with DCM and washed successively with saturated $NaHCO_3$ solution, water and brine. The residue was concentrated under vacuum after dried over anhydrous sodium sulfate. The residue was applied onto a silica gel column with ethyl acetate/petroleum ether (23:77). This resulted in 520 mg (51%) of the title compound as a white solid.

Scheme 3 (INT-012)

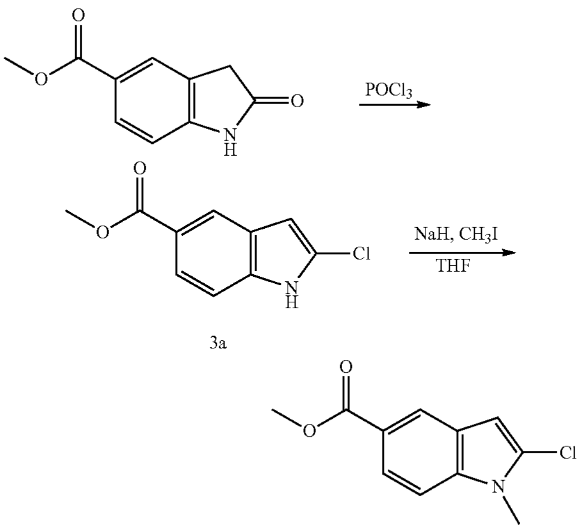

3a

INT-012

Experimental Details for INT-012 (Scheme 3)

Methyl 2-chloro-1H-indole-5-carboxylate (Compound 3a)

To a solution of phosphoryl trichloride (4 mL) was added methyl 2-oxo-2,3-dihydro-1H-indole-5-carboxylate (500 mg, 2.62 mmol). The resulting solution was stirred for 30 min at 50° C. The resulting solution was diluted with 10 mL of ethyl acetate. The resulting solution was washed successively with water and brine. The residue was concentrated under vacuum after dried over anhydrous sodium sulfate. The crude product was applied onto a silica gel column with ethyl acetate/petroleum ether (1:9). This resulted in 0.15 g (27%) of the title compound as a white solid. LC-MS (ESI, m/z): $[M+H]^+=210.0$.

Methyl 2-chloro-1-methyl-1H-indole-5-carboxylate (Compound INT-012)

To a solution of Compound 3a (150 mg, 0.72 mmol) in THF (5 mL) was added sodium hydride (71 mg, 2.96 mmol) batchwise at 0° C. The mixture was stirred for 30 min at room temperature then $CH_3I$ (254 mg, 1.79 mmol) was added. The mixture was stirred for 6 h at room temperature. The reaction was quenched by adding 5 mL of water. The resulting solution was extracted with 3×5 mL of ethyl acetate and the organic layers were combined. The resulted organic phase was washed successively with water and brine. The residue was concentrated under vacuum after dried over anhydrous sodium sulfate. The residue was applied onto a silica gel column with ethyl acetate/petroleum ether (1:10). This resulted in 125 mg (78%) of the title compound as a white solid. LC-MS (ESI, m/z): $[M+H]^+=224.0$.

Following the procedure described above for Scheme 3 and substituting the appropriate reagents, starting material and purification method known to those skilled in the art, the following common intermediate was prepared.

TABLE 11

| Compound | Structure | LC-MS $(M + H)^+$ |
|---|---|---|
| INT-013 | 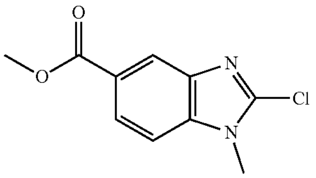 | 225.0 |

Final Compounds Synthetic Schemes

Scheme 4 (Compound II-03)

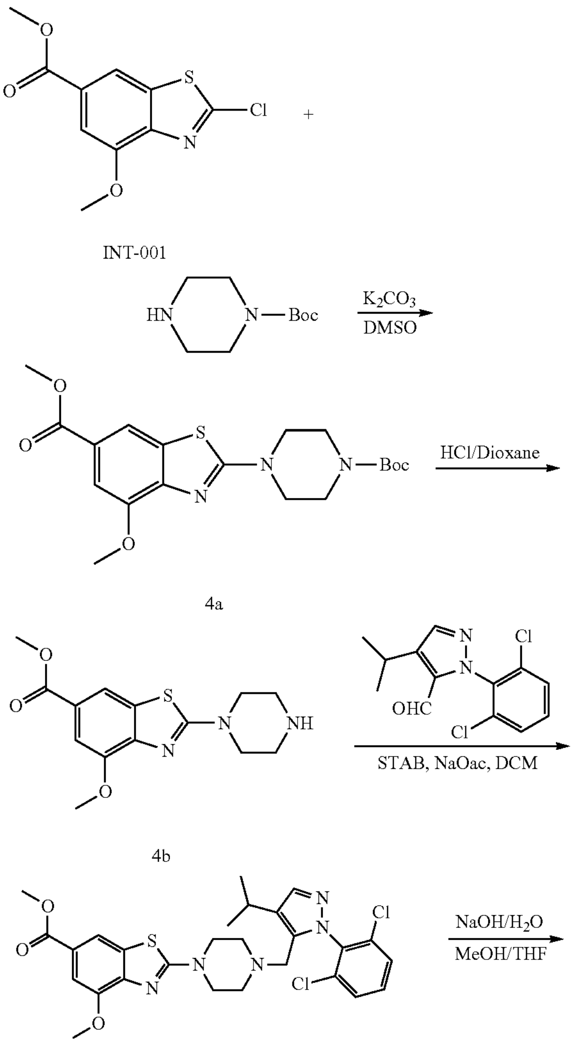

INT-001

4a

4b

4c

-continued

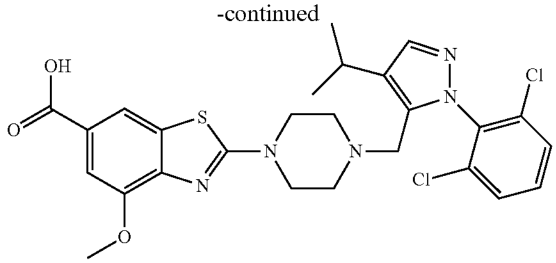

II-03

Experimental Details for Compound II-03 (Scheme 4)

Methyl 2-[4-[(tert-butoxy) carbonyl]piperazin-1-yl]-4-methoxy-1,3-benzothiazole-6-carboxylate (Compound 4a)

To a solution of methyl 2-chloro-4-methoxy-1,3-benzothiazole-6-carboxylate (1 g, 3.88 mmol) in DMSO (10 mL) was added tert-butyl piperazine-1-carboxylate (720 mg, 3.87 mmol) and potassium carbonate (800 mg, 5.79 mmol). The resulting solution was stirred for 2 h at 120° C. The reaction was diluted with water and extracted with 3×50 mL of dichloromethane. The organic layers were combined and washed with water and brine, then dried over anhydrous sodium sulfate and concentrated under vacuum. The residue was applied onto a silica gel column with ethyl acetate/petroleum ether (1:5). This resulted in 1.5 g of the title compound as a yellow solid. LC-MS (ESI): $[M+H]^+=408.2$.

Methyl 4-methoxy-2-(piperazin-1-yl)benzo[d]thiazole-6-carboxylate (Compound 4b)

To a solution of Compound 4a (1.5 g, 3.7 mmol) in dichloromethane (10 mL) was added a solution of HCl in dioxane (10 mL, 4M). The resulting solution was stirred for 2 h at room temperature. The reaction mixture was concentrated under vacuum and the residue dissolved in methanol. The pH value of the solution was adjusted to 6-7 with potassium carbonate and the solids were filtered out. The resulting mixture was concentrated under vacuum. This resulted in 1.01 g of the title compound as a white solid. The resulted product used directly without further purification. LC-MS (ESI): $[M+H]^+=308.3$.

Methyl 2-(4-[[1-(2,6-dichlorophenyl)-4-(propan-2-yl)-1H-pyrazol-5-yl]methyl]piperazin-1-yl)-4-methoxy-1,3-benzothiazole-6-carboxylate (Compound 4c)

To a solution of Compound 4b (131 mg, 0.43 mmol) and 1-(2,6-dichlorophenyl)-4-(propan-2-yl)-1H-pyrazole-5-carbaldehyde (100 mg, 0.35 mmol) in dichloromethane (5 mL) was added NaOAc (96 mg, 0.71 mmol). The mixture was stirred for 1 h at room temperature then $NaBH(OAc)_3$ (300 mg, 1.42 mmol) was added. The resulting solution was stirred overnight at room temperature. The mixture was concentrated under vacuum. The residue was applied onto a silica gel column with ethyl acetate/petroleum ether (1:3). This resulted in 125 mg (51%) of the title compound as a white oil. LC-MS (ESI, m/z): [M+H]+=574.1.

2-(4-[[1-(2,6-Dichlorophenyl)-4-(propan-2-yl)-1H-pyrazol-5-yl]methyl]piperazin-1-yl)-4-methoxy-1,3-benzothiazole-6-carboxylic acid (Compound II-03)

To a solution of Compound 4c (80 mg, 0.14 mmol) in a mixed solvent of methanol (1 mL) and tetrahydrofuran (1 mL) was added a solution of sodium hydroxide (49 mg, 1.23 mmol) in water (1 mL). The resulting solution was stirred for 2 h at 50° C. The pH value of the solution was adjusted to 5 with hydrogen chloride (2 N). The mixture was concentrated under vacuum. The residue was applied onto a silica gel column with dichloromethane/methanol (15:1). This resulted in 27.1 mg (35%) of the title compound as a white solid. LC-MS (ESI, m/z): $[M+H]^+=560.2$. $^1H$ NMR (400 MHz, DMSO-$d_6$, ppm): δ 7.96 (s, 1H), 7.69-7.67 (m, 3H), 7.58-7.54 (m, 1H), 7.40 (s, 1H), 3.87 (s, 3H), 3.41 (s, 2H), 3.34-3.36 (m, 4H), 3.01-2.94 (m, 1H), 2.34-2.31 (m, 4H), 1.23 (d, J=7.2 Hz, 6H).

Scheme 5 (Compound II-07)

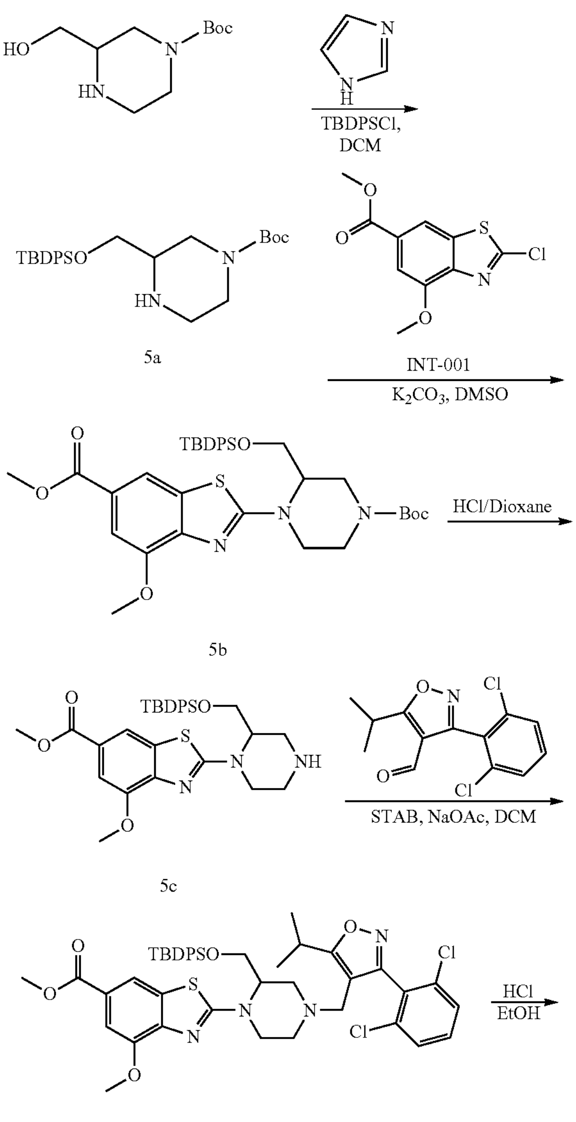

5a

5b

5c

5d

-continued

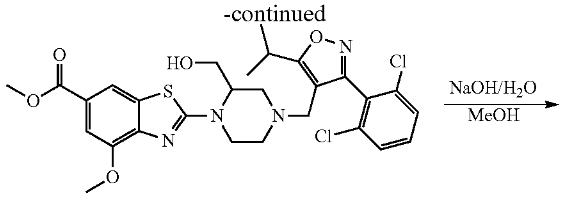

5e

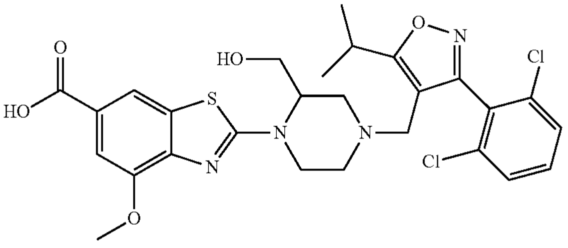

II-07

Experimental Details for Compound II-07 (Scheme 5)

tert-Butyl 3-[[(tert-butyldiphenylsilyl)oxy]methyl] piperazine-1-carboxylate (Compound 5a)

To a solution of tert-butyl 3-(hydroxymethyl)piperazine-1-carboxylate (1 g, 4.62 mmol) in dichloromethane (10 mL) was added 1H-imidazole (629 mg, 9.24 mmol). This was followed by addition of a solution of TBDPSCl (1.18 mL, 1.30 mmol) in dichloromethane (10 mL) dropwise with stirring. The mixture was allowed warm to room temperature and stirred for 3 h. The resulting solution was extracted with 3×50 mL of dichloromethane and the organic layers were combined. The resulting mixture was washed with 3×50 mL of sodium bicarbonate and 1×50 mL of brine. The resulting mixture was concentrated under vacuum after dried over anhydrous sodium sulfate. The residue was applied onto a silica gel column with ethyl acetate/petroleum ether (7:3). This resulted in 1.4 g (67%) of the title compound as a light yellow oil. LC-MS (ESI, m/z): [M+H]+=455.3.

Methyl 2-[4-[(tert-butoxy)carbonyl]-2-[[(tert-butyldiphenylsilyl)oxy]methyl]piperazin-1-yl]-4-methoxy-1,3-benzothiazole-6-carboxylate (Compound 5b)

To a solution of Compound 5a (455 mg, 1.0 mmol) in DMSO (10 mL) was added methyl 2-chloro-4-methoxy-1,3-benzothiazole-6-carboxylate (223 mg, 0.87 mmol) and potassium carbonate (207 mg, 1.50 mmol). After stirring for 3 h at 120° C., the resulting mixture was diluted with ethyl acetate (100 mL). The resulted mixture was washed with water and brine. The residue was concentrated under vacuum after dried over anhydrous sodium sulfate. The residue was applied onto a silica gel column with ethyl acetate/petroleum ether (1:4). This resulted in 300 mg (44%) of the title compound as a white solid. LC-MS (ESI, m/z): [M+H]+=676.2.

Methyl 2-(2-[[(tert-butyldiphenylsilyl)oxy]methyl] piperazin-1-yl)-4-methoxy-1,3-benzothiazole-6-carboxylate (Compound 5c)

To a solution of Compound 5b (300 mg, 0.44 mmol) in dioxane (5 mL) was added a solution of hydrogen chloride in dioxane (5 mL, 4M). After stirring for 1 h at room temperature, the resulting mixture was concentrated under vacuum. The resulted solids were washed with ethyl acetate and dried under vacuum. This resulted in 120 mg (47%) of the title compound as a light yellow oil. LC-MS (ESI, m/z): $[M+H]^+$=576.3.

Methyl 2-(2-[[(tert-butyldiphenylsilyl)oxy]methyl]-4-[[3-(2,6-dichlorophenyl)-5-(propan-2-yl)-1,2-oxazol-4-yl]methyl]piperazin-1-yl)-4-methoxy-1,3-benzothiazole-6-carboxylate (Compound 5d)

To a solution of Compound 5c (100 mg, 0.17 mmol) and 3-(2,6-dichlorophenyl)-5-(propan-2-yl)-1,2-oxazole-4-carbaldehyde (49.39 mg, 0.17 mmol) in dichloromethane (5 mL) was added sodium acetate (14.6 mg, 0.18 mmol). After stirring for 30 min, $NaBH(OAc)_3$ (111 mg, 0.52 mmol) was added. The resulting solution was stirred for 16 h at room temperature. The resulting mixture was concentrated under vacuum. The residue was applied onto a silica gel column with ethyl acetate/petroleum ether (1:4). This resulted in 72.4 mg (49%) of the title compound as a white solid. LC-MS (ESI, m/z): [M+H]+=843.1.

Methyl 2-(4-[[3-(2,6-dichlorophenyl)-5-(propan-2-yl)-1,2-oxazol-4-yl]methyl]-2-(hydroxymethyl)piperazin-1-yl)-4-methoxy-1,3-benzothiazole-6-carboxylate (Compound 5e)

To a solution of Compound 5d (70 mg, 0.08 mmol) in ethanol (10 mL) was added hydrogen chloride (2 mL, 6M). The resulting solution was stirred for 16 h at room temperature. The residue was applied onto a silica gel column with ethyl acetate/petroleum ether (2:1). This resulted in 30 mg (60%) of the title compound as a white solid. LC-MS (ESI, m/z): $[M+H]^+$=605.2.

2-(4-[[3-(2,6-Dichlorophenyl)-5-(propan-2-yl)-1,2-oxazol-4-yl]methyl]-2-(hydroxymethyl)piperazin-1-yl)-4-methoxy-1,3-benzothiazole-6-carboxylic acid (Compound II-07)

Into a 25-mL round-bottom flask, was placed a solution of Compound 5e (100 mg, 0.17 mmol) in methanol (4 mL), then a solution of sodium hydroxide (64 mg, 1.60 mmol) in water (2 mL) was added. After stirring for 2 h at 50° C., the mixture was concentrated under vacuum. The residue was applied onto a silica gel column with $CH_3CN/H_2O$ (4:1). This resulted in 16.1 mg (16%) of the title compound as a white solid. LC-MS (ESI, m/z): $[M+H]^+$=591.3. $^1$H-NMR (300 MHz, $CDCl_3$, ppm): δ 7.99 (s, 1H), 7.67-7.51 (m, 4H), 4.62-4.22 (m, 5H), 4.04 (s, 3H), 3.93-3.68 (m, 3H), 3.37-3.33 (m, 1H), 2.88-2.73 (m, 3H), 1.48 (brs, 6H).

Scheme 6 (Compound II-22)

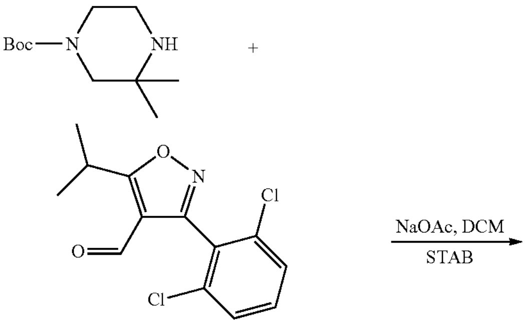

-continued

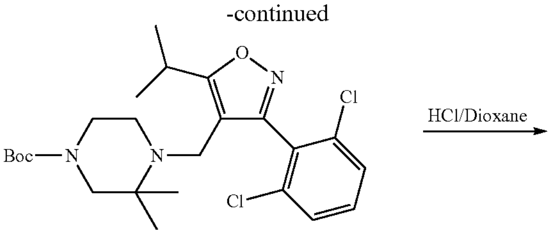

6a

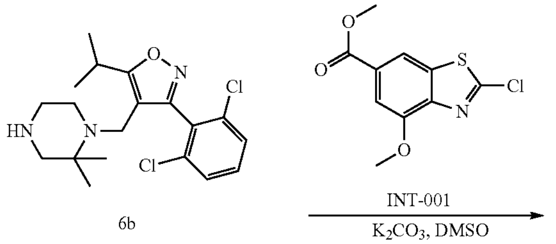

6b

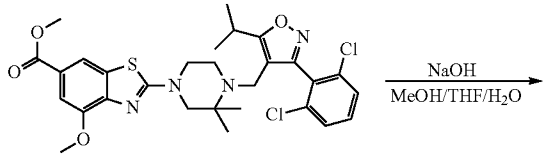

6c

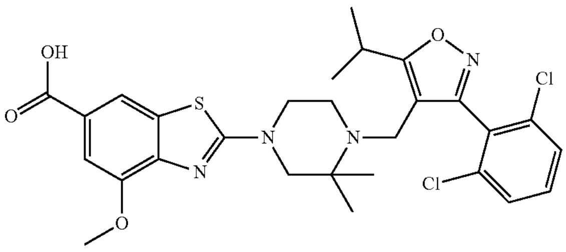

II-22

Experimental Details for Compound II-22 (Scheme 6)

tert-Butyl 4-[[3-(2,6-dichlorophenyl)-5-(propan-2-yl)-1,2-oxazol-4-yl]methyl]-3,3-dimethylpiperazine-1-carboxylate (Compound 6a)

To a solution of tert-butyl 3,3-dimethylpiperazine-1-carboxylate (150 mg, 0.70 mmol) in dichloromethane (5 mL) was added 3-(2,6-dichlorophenyl)-5-(propan-2-yl)-1,2-oxazole-4-carbaldehyde (180 mg, 0.63 mmol) and sodium acetate (87 mg, 1.06 mmol). The mixture was stirred for 1 h at room temperature. Then STAB (404 mg, 1.91 mmol) was added. The resulting solution was stirred overnight at room temperature. The reaction was then quenched by adding water (15 mL). The resulting mixture was extracted with 5×5 mL of dichloromethane and the organic layers were combined. The organic phase was washed successively with water and brine. The residue was concentrated under vacuum after dried over anhydrous sodium sulfate. The residue was applied onto a silica gel column with ethyl acetate/petroleum ether (1:10). This resulted in 0.116 g (38%) of the title compound as a white solid. LC-MS (ESI, m/z): $[M+H]^+$=482.4.

1-[[3-(2,6-Dichlorophenyl)-5-(propan-2-yl)-1,2-oxazol-4-yl]methyl]-2,2-dimethylpiperazine (Compound 6b)

To a solution of Compound 6a (116 mg, 0.24 mmol) in dioxane was added a solution of hydrogen chloride in dioxane (3 mL, 4M). The resulting solution was stirred for 1 h at room temperature. The resulting mixture was concentrated under vacuum. This resulted in 0.09 g (98%) of the title compound as a white solid. LC-MS (ESI, m/z): $[M+H]^+$=382.1.

Methyl 2-(4-[[3-(2,6-dichlorophenyl)-5-(propan-2-yl)-1,2-oxazol-4-yl]methyl]-3,3-dimethylpiperazin-1-yl)-4-methoxy-1,3-benzothiazole-6-carboxylate (Compound 6c)

To a solution of methyl 2-chloro-4-methoxy-1,3-benzothiazole-6-carboxylate (88 mg, 0.34 mmol) in DMSO (3 mL) was added Compound 6b (90 mg, 0.24 mmol) and potassium carbonate (107 mg, 0.77 mmol). The resulting solution was stirred for 3 h at 120° C. The reaction was then quenched by the addition of water (5 mL). The resulting solution was extracted with 5×5 mL of ethyl acetate and the organic layers were combined. The organic phase was washed successively with water and brine. The residue was concentrated under vacuum after dried over anhydrous sodium sulfate. The residue was applied onto a silica gel column with ethyl acetate/petroleum ether (1:3). This resulted in 0.11 g (77%) of the title compound as a white solid. LC-MS (ESI, m/z): $[M+H]^+$=603.2.

2-(4-[[3-(2,6-Dichlorophenyl)-5-(propan-2-yl)-1,2-oxazol-4-yl]methyl]-3,3-dimethylpiperazin-1-yl)-4-methoxy-1,3-benzothiazole-6-carboxylic acid (Compound II-22)

To a solution of Compound 6c (110 mg, 0.18 mmol) in a mixed solvent of methanol/tetrahydrofuran/water (3 mL, 1:1:1) was added sodium hydroxide (37 mg, 0.93 mmol). The resulting solution was stirred for 2 h at 50° C. The pH value of the solution was adjusted to 5 with hydrogen chloride (2 N). The mixture was concentrated under vacuum. The residue was applied onto a silica gel column with dichloromethane/methanol (15:1). This resulted in 0.05 g (47%) of the title compound as a white solid. LC-MS (ESI, m/z): $[M+H]^+$=589.2. $^1H$ NMR (400 MHz, DMSO-$d_6$, ppm): δ 7.96 (d, J=1.6 Hz, 1H), 7.64-7.62 (m, 2H), 7.57-7.53 (m, 1H), 7.38 (d, J=1.2 Hz, 1H), 3.88 (s, 3H), 3.48 (s, 2H), 3.39-3.27 (m, 3H), 3.00 (s, 2H), 2.44-2.42 (m, 2H), 1.33-1.30 (d, J=6.8 Hz, 6H), 0.75 (s, 6H).

Scheme 7 (Compound II-45)

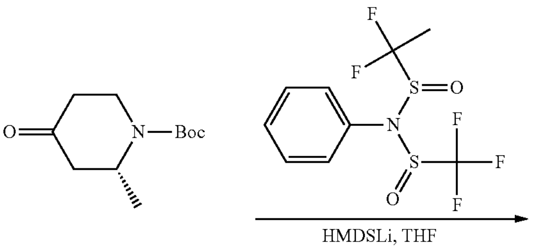

-continued

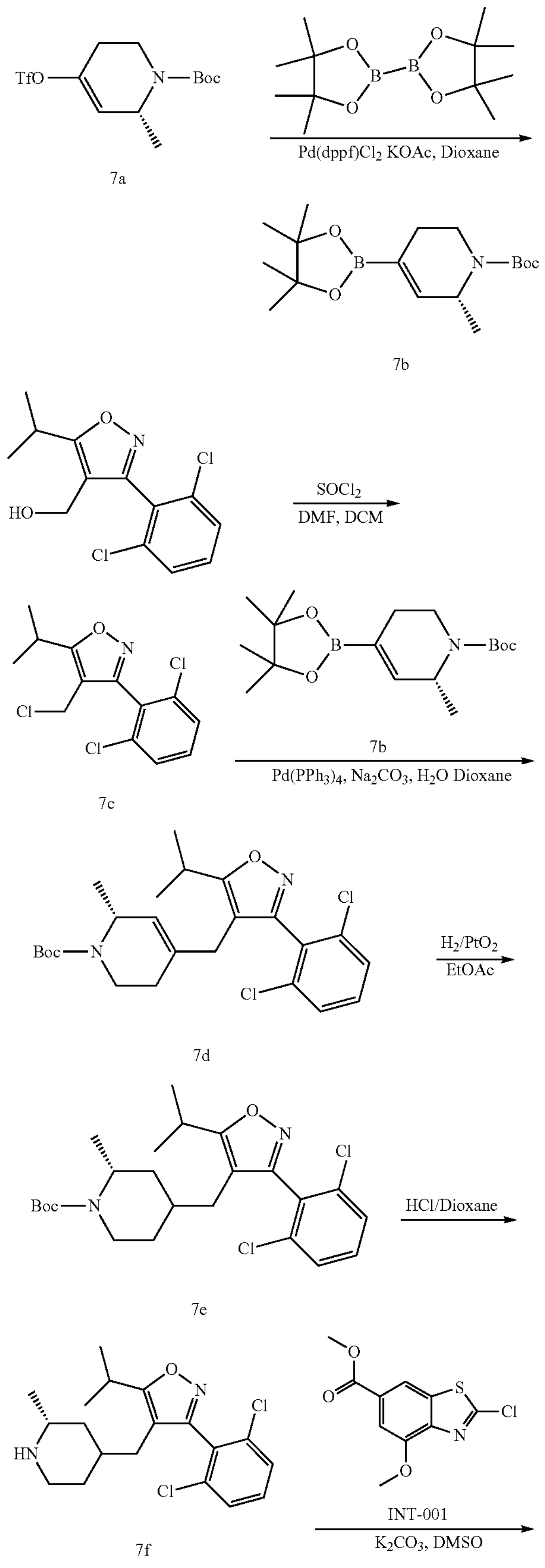

-continued

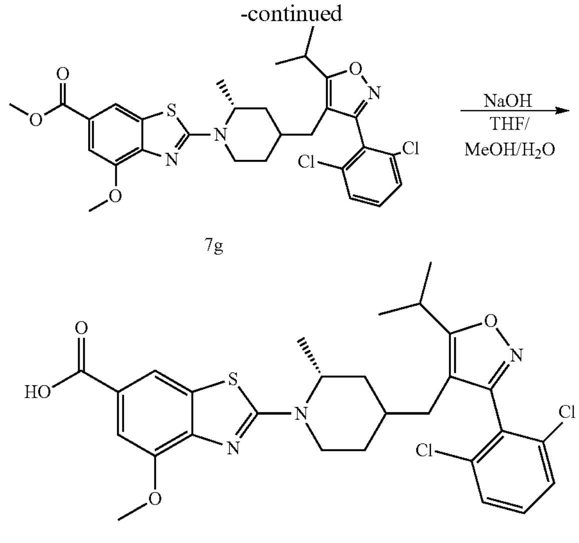

II-45

Experimental Details for Compound II-45 (Scheme 7)

(R)-tert-Butyl 2-methyl-4-(trifluoromethylsulfonyloxy)-5,6-dihydropyridine-1(2H)-carboxylate (Compound 7a)

To a solution of N-[(1,1-difluoroethane) sulfinyl]-1,1,1-trifluoro-N-phenylmethanesulfinamide (213 mg, 1.0 mmol) in THF (3 mL) was added HMDSLi (1.1 mL, 1.1 mmol) dropwise at −78° C. under $N_2$ atmosphere. The mixed was stirred for 30 min at −78° C., then a solution of tert-butyl (2R)-2-methyl-4-oxopiperidine-1-carboxylate (393 mg, 1.1 mmol) in THF (2 mL) was added dropwise. The resulting mixture was stirred for 2 h at −78° C. The reaction was then quenched by the addition of 5 mL of water. The resulting solution was diluted with ethyl acetate. The resulted mixture was washed with water and brine. The mixture was dried over anhydrous sodium sulfate and concentrated under vacuum. This resulted in 300 mg of the title compound as a colorless oil (crude product).

(R)-tert-Butyl 2-methyl-4-(4,4,5,5-tetramethyl-1,3,2-dioxaborolan-2-yl)-5,6-dihydropyridine-1(2H)-carboxylate (Compound 7b)

To a solution of 4,4,5,5-tetramethyl-2-(tetramethyl-1,3,2-dioxaborolan-2-yl)-1,3,2-dioxaborolane (100 mg, 0.39 mmol) in dioxane (2 mL) was added Compound 7a (110 mg, 0.32 mmol), $Pd(dppf)Cl_2$ (66 mg, 0.09 mmol) and potassium acetate (81 mg, 0.83 mmol). The mixture was stirred overnight at 80° C. under $N_2$ atmosphere. The resulting mixture was diluted with ethyl acetate. The resulted mixture was washed with water and brine. The residue was dried over anhydrous sodium sulfate and concentrated under vacuum. The crude product was applied onto a silica gel column with ethyl acetate/petroleum ether (27:73). This resulted in 100 mg (79%) of the title compound as a white solid. LC-MS (ESI, m/z): $[M+H]^+$=324.2.

4-(Chloromethyl)-3-(2,6-dichlorophenyl)-5-(propan-2-yl)-1,2-oxazole (Compound 7c)

To a solution of [3-(2,6-dichlorophenyl)-5-(propan-2-yl)-1,2-oxazol-4-yl]methanol (500 mg, 1.75 mmol) in dichloromethane (5 mL) was added sulfurous dichloride (225 mg, 1.89 mmol) and DMF (0.5 mL). The resulting solution was stirred for 1 h at room temperature. The resulting mixture was concentrated under vacuum. The residue was applied onto a silica gel column with ethyl acetate/petroleum ether (1:9). This resulted in 460 mg (86%) of the title compound as a white solid. LC-MS (ESI, m/z): [M+H]+=304.3.

(R)-tert-Butyl 4-((3-(2,6-dichlorophenyl)-5-isopropylisoxazol-4-yl)methyl)-2-methyl-5,6-dihydropyridine-1(2H)-carboxylate (Compound 7d)

To a solution of Compound 7b (240 mg, 0.74 mmol) and Compound 7c (150 mg, 0.49 mmol) in dioxane (4 mL) was added tetrakis(triphenylphosphane) palladium (58 mg, 0.05 mmol), sodium carbonate (159 mg, 1.49 mmol) and water (1 mL). The resulting solution was stirred for 4 h at 80° C. under $N_2$ atmosphere. The mixture was concentrated under vacuum. The residue was applied onto a silica gel column with ethyl acetate/petroleum ether (23:77). This resulted in 80 mg (35%) of the title compound as a yellow oil. LC-MS (ESI, m/z): $[M+H]^+$=465.4.

(2R)-tert-Butyl 4-((3-(2,6-dichlorophenyl)-5-isopropylisoxazol-4-yl)methyl)-2-methylpiperidine-1-carboxylate (Compound 7e)

To a solution of Compound 7d (150 mg, 0.32 mmol) in ethyl acetate (3 mL) was added $PtO_2$ (22.7 mg, 0.10 mmol). The mixed was stirred overnight at room temperature under $H_2$ atmosphere. The solids were filtered out. The resulting mixture was concentrated under vacuum. This resulted in 120 mg (80%) of the title compound as a white solid. LC-MS (ESI, m/z): $[M+H]^+$=467.0.

3-(2,6-Dichlorophenyl)-5-isopropyl-4-(((2R)-2-methylpiperidin-4-yl)methyl) isoxazole (Compound 7f)

To a solution of Compound 7e (120 mg, 0.26 mmol) in dioxane (3 mL) was added a mixture of hydrogen chloride in dioxane (5 mL, 4M). The mixture was stirred for 1 h at room temperature then concentrated under vacuum. This resulted in 70 mg (74%) of the title compound as a yellow solid. LC-MS (ESI, m/z): $[M+H]^+$=367.0.

Methyl 2-((2R)-4-((3-(2,6-dichlorophenyl)-5-isopropylisoxazol-4-yl)methyl)-2-methylpiperidin-1-yl)-4-methoxybenzo[d]thiazole-6-carboxylate (Compound 7g)

To a solution of methyl 2-chloro-4-methoxy-1,3-benzothiazole-6-carboxylate (70 mg, 0.27 mmol) in DMSO (3 mL) was added Compound 7f (99 mg, 0.27 mmol) and potassium carbonate (112 mg, 0.80 mmol). The mixture was stirred for 2 h at 120° C. The reaction was then quenched by the addition of water. The resulting solution was diluted with EA. The resulting mixture was washed with water and brine. The mixture was dried over anhydrous sodium sulfate and concentrated under vacuum. The residue was applied onto a silica gel column with ethyl acetate/petroleum ether (25:75). This resulted in 70 mg (44%) of the title compound as a yellow solid. LC-MS (ESI, m/z): [M+H]+=588.2.

2-((2R)-4-((3-(2,6-Dichlorophenyl)-5-isopropylisoxazol-4-yl)methyl)-2-methylpiperidin-1-yl)-4-methoxybenzo[d]thiazole-6-carboxylic acid (Compound II-45)

To a solution of Compound 7g (70 mg, 0.12 mmol) in a mixture of THF (1 mL), water (1 mL) and methanol (1 mL) was added sodium hydroxide (24 mg, 0.60 mmol). The resulting solution was stirred for 1 h at 50° C. The pH value of the solution was adjusted to 6 with hydrogen chloride (2 M). The solids were filtered out. The reaction mixture was concentrated under vacuum. The crude product was purified by Prep-HPLC with the following conditions: Column, SunFire Prep C18 OBD Column, 19*150 mm, 5 um; mobile phase: Water (0.1% TFA) and ACN (60% ACN up to 67% in 10 min); Detector, UV 254/220 nm. This resulted in 3.9 mg (6%) of the title compound as a white solid. LC-MS (ESI, m/z): $[M+H]^+$=573.7. $^1$HNMR (400 MHz, DMSO-$d_6$, ppm): δ 7.94 (s, 1H), 7.71-7.69 (m, 2H), 7.63-7.59 (m, 1H), 7.39 (s, 1H), 4.35 (s, 1H), 3.87 (s, 3H), 3.31-3.23 (m, 2H), 3.10-3.04 (m, 1H), 2.34-2.26 (m, 1H), 2.19-2.10 (m, 1H), 1.63-1.45 (m, 3H), 1.33-1.24 (m, 7H), 1.16-1.08 (m, 1H), 1.05-1.03 (d, J 6.8 Hz, 3H).

Scheme 8 (Compound II-47)

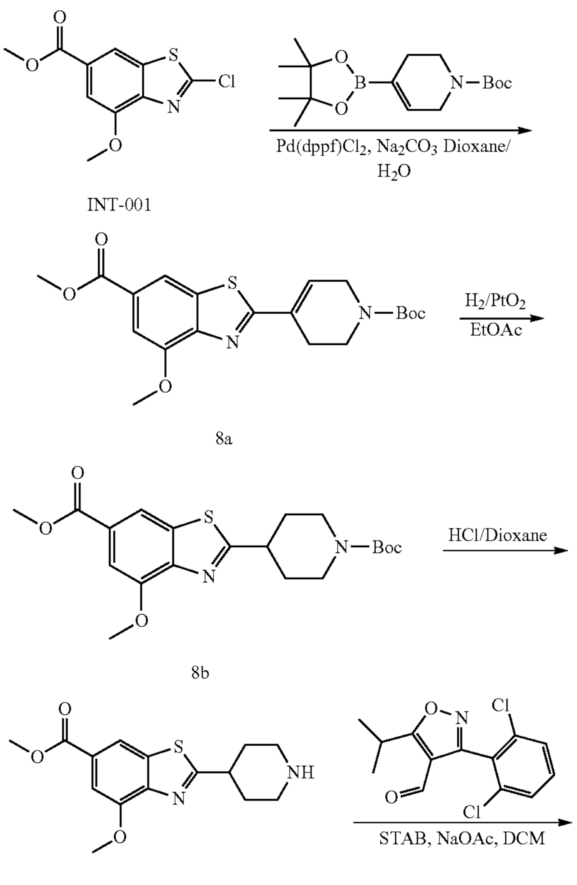

INT-001

8a

8b

8c

-continued

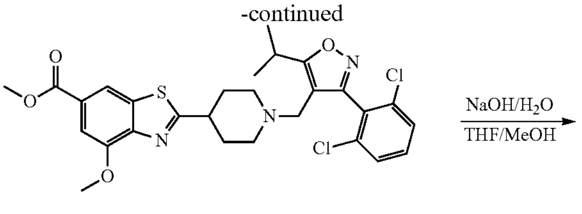

8d

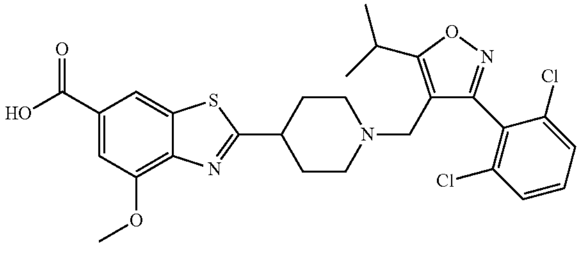

II-47

Experimental Details for Compound II-47 (Scheme 8)

Methyl 2-(1-(tert-butoxycarbonyl)-1,2,3,6-tetrahydropyridin-4-yl)-4-methoxybenzo[d]thiazole-6-carboxylate (Compound 8a)

To a solution of methyl 2-chloro-4-methoxy-1,3-benzothiazole-6-carboxylate (300 mg, 1.16 mmol) and tert-butyl 4-(tetramethyl-1,3,2-dioxaborolan-2-yl)-1,2,3,6-tetrahydropyridine-1-carboxylate (543 mg, 1.76 mmol) in a mixed solvent of dioxane (4 mL) and water (1 mL) was added Pd(dppf)$Cl_2$ (87.7 mg, 0.12 mmol) and sodium carbonate (372 mg, 3.51 mmol). The resulting solution was stirred for 3 h at 80° C. under N2 atmosphere. The filtrate was concentrated under vacuum after filtration. The residue was applied onto a silica gel column with ethyl acetate/petroleum ether (21:79). This resulted in 340 mg (72%) of the title compound as a white solid. LC-MS (ESI, m/z): $[M+H]^+$=405.2

Methyl 2-(1-(tert-butoxycarbonyl) piperidin-4-yl)-4-methoxybenzo[d]thiazole-6-carboxylate (Compound 8b)

To a solution of Compound 8a (340 mg, 0.84 mmol) in ethyl acetate (6 mL) was added $PtO_2$ (76 mg, 0.33 mmol). The resulting solution was stirred overnight at 30° C. under $H_2$ atmosphere. The solids were filtered out. The filtrate was concentrated under vacuum. The residue was applied onto a silica gel column with ethyl acetate/petroleum ether (28:72). This resulted in 250 mg (73%) of the title compound as a white solid. LC-MS (ESI, m/z): [M+H]+=407.2.

Methyl 4-methoxy-2-(piperidin-4-yl)benzo[d]thiazole-6-carboxylate (Compound 8c)

Into a 50-mL round-bottom flask was placed Compound 8b (250 mg, 0.62 mmol, 1.00 equiv), hydrogen chloride/dioxane (10 mL). The resulting solution was stirred for 1 h at room temperature. The resulting mixture was concentrated under vacuum. This resulted in 180 mg (96%) of the title compound as a white solid. LC-MS (ES, m/z): [M+H]+=307.1.

Methyl 2-(1-((3-(2,6-dichlorophenyl)-5-isopropylisoxazol-4-yl)methyl) piperidin-4-yl)-4-methoxybenzo[d]thiazole-6-carboxylate (Compound 8d)

To a solution of Compound 8b (135 mg, 0.44 mmol), and 3-(2,6-dichlorophenyl)-5-(propan-2-yl)-1,2-oxazole-4-carbaldehyde (125 mg, 0.44 mmol) in dichloromethane (3 mL) was added sodium acetate (37 mg, 0.45 mmol). The mixture was stirred for 30 min then $NaBH(OAc)_3$ (280 mg, 1.32 mmol) was added. The resulting solution was stirred overnight at room temperature. The solids were filtered out. The residue was applied onto a silica gel column with ethyl acetate/petroleum ether (32:68). This resulted in 130 mg (51%) of the title compound as colorless oil. LC-MS (ESI, m/z): $[M+H]^+$=574.3.

2-(1-((3-(2,6-Dichlorophenyl)-5-isopropylisoxazol-4-yl)methyl) piperidin-4-yl)-4-methoxybenzo[d]thiazole-6-carboxylic acid (Compound II-47)

To a solution of Compound 8d (130 mg, 0.23 mmol) in a mixed solvent of THF (1 mL) and methanol (1 mL) was added a solution of sodium hydroxide (45 mg, 1.13 mmol) in water (0.5 mL). The resulting solution was stirred for 1 h at 50° C. The pH value of the solution was adjusted to 6 with hydrogen chloride (2 N). The resulting mixture was concentrated under vacuum. The residue was applied onto a C18 column with $H_2O/CH_3CN$ (35:65). This resulted in 35.7 mg (28%) of the title compound as a white solid. LC-MS (ESI, m/z): $[M+H]^+$=560.0. HNMR (300 MHz, DMSO-$d_6$, ppm): δ 8.25 (s, 1H), 7.59 (s, 1H), 7.42-7.38 (m, 3H), 4.12 (s, 3H), 3.29 (brs, 3H), 3.15 (brs, 1H), 2.89 (brs, 2H), 2.09-1.85 (m, 4H), 1.75-1.56 (m, 2H), 1.43 (d, J=6.6 Hz, 6H).

Scheme 9 (Compound VII-04)

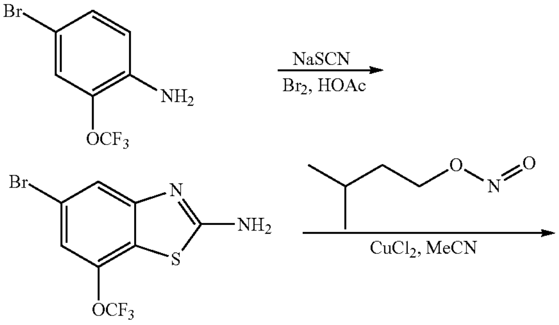

9a

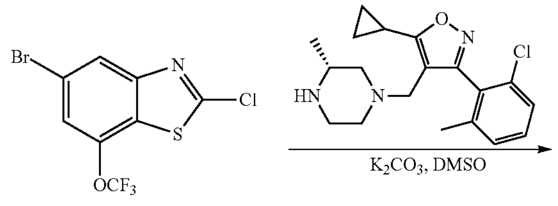

9b

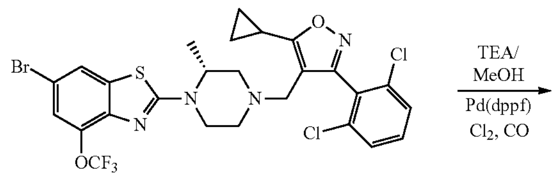

9c

-continued

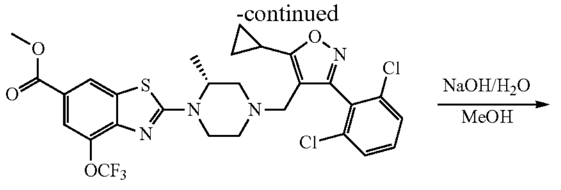

9d

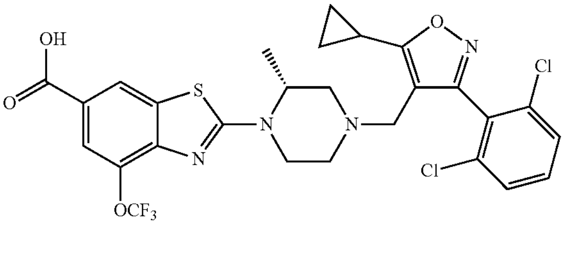

VII-04

Experimental Details for Compound VII-04 (Scheme 9)

5-Bromo-7-(trifluoromethoxy)benzo[d]thiazol-2-amine (Compound 9a)

To a solution of 4-bromo-2-(trifluoromethoxy) aniline (5.00 g, 19.53 mmol) in acetic acid (60 mL) was added NaSCN (6.33 g, 78.12 mmol) batchwise at room temperature. The mixture was stirred for 30 min then a solution of $Br_2$ (6.24 g, 39.0 mmol) in acetic acid (10 mL). The resulting mixture was stirred for 8 h at room temperature. The resulting mixture was concentrated under vacuum. The residue was suspended in water. The pH value of the mixture was adjusted to 9 with solid $Na_2CO_3$. The solids were collected by filtration and washed with water, dried under vacuum. This resulted in 5.70 g (93%) of the title compound as an orange solid (crude product). LC-MS (ESI, m/z): $[M+H]^+$=315.

5-Bromo-2-chloro-7-(trifluoromethoxy)benzo[d]thiazole (Compound 9b)

To a suspension of Compound 9a (4.40 g, 14.05 mmol) in MeCN (60 mL) was added $CuCl_2$ (3.77 g, 28.02 mmol). The mixture was stirred for 30 min before 3-methylbutyl nitrite (2.47 g, 21.10 mmol) was added dropwise at room temperature. The resulting mixture was stirred for 8 h at room temperature. The solid was filtrated out, the resulted filtrate was diluted with ethyl acetate. The mixture was washed with water and brine. The resulting mixture was concentrated under vacuum after dried over anhydrous sodium sulfate. The residue was applied onto a silica gel column with ethyl acetate/petroleum ether (1:3). This resulted in 840 mg (18%) of the title compound as a light yellow solid.

(R)-4-((4-(6-Bromo-4-(trifluoromethoxy)benzo[d]thiazol-2-yl)-3-methylpiperazin-1-yl)methyl)-5-cyclopropyl-3-(2,6-dichlorophenyl) isoxazole (Compound 9c)

To a solution of Compound 9b (150 mg, 0.45 mmol) in DMSO (5 mL) was added $K_2CO_3$ (62.1 mg, 0.45 mmol) and (3R)-1-[[5-cyclopropyl-3-(2,6-dichlorophenyl)-1,2-oxazol- 4-yl]methyl]-3-methylpiperazine (110 mg, 0.30 mmol). The mixture was stirred for 12 h at 120° C. The mixture was diluted with water. The mixture was extracted with ethyl acetate several times. The organic layers were combined and washed with water and brine. The residue was dried over anhydrous sodium sulfate and concentrated under vacuum. The residue was applied onto a silica gel column with ethyl acetate/petroleum ether (1:3). This resulted in 160 mg (79%) of the title compound as an off-white solid. LC-MS (ESI, m/z): $[M+H]^+$=663.3.

(R)-Methyl 2-(4-((5-cyclopropyl-3-(2,6-dichlorophenyl) isoxazol-4-yl)methyl)-2-methylpiperazin-1-yl)-4-(trifluoromethoxy)benzo[d]thiazole-6-carboxylate (Compound 9d)

To a solution of Compound 9c (160 mg, 0.24 mmol) and triethylamine (1.5 mL) in methanol (5 mL) was added Pd(dppf)$Cl_2$ (20 mg, 0.027 mmol). The mixture was stirred for 48 h at 80° C. under CO (20 atm). The solid was filtered out after cooling to room temperature. The filtrate was concentrated and applied onto a silica gel column with ethyl acetate/petroleum ether (1:3). This resulted in 120 mg (77%) of the title compound as an off-white solid. LC-MS (ESI, m/z): $[M+H]^+$=641.0.

2-[(2R)-4-[[5-Cyclopropyl-3-(2,6-dichlorophenyl)-1,2-oxazol-4-yl]methyl]-2-methylpiperazin-1-yl]-4-(trifluoromethoxy)-1,3-benzothiazole-6-carboxylic acid (Compound VII-04)

To a solution of Compound 9d (120 mg, 0.19 mmol) in methanol (4 mL) was added a solution of sodium hydroxide (50 mg) in water (2 mL). The mixture was stirred for 4 h at 50° C. The pH of the mixture was adjusted to 2 with HCl (2M). The residue was extracted with ethyl acetate several times. The organic layers were combined and concentrated under vacuum after dried over anhydrous sodium sulfate. The crude product was purified by Prep-HPLC with the following conditions (2 #-AnalyseHPLC-SHIMADZU (HPLC-10)): Column, XSelect CSH Prep C18 OBD Column, 5 um, 19*150 mm; mobile phase, Water (0.05% HCl) and ACN (60% ACN up to 85% in 7 min); Detector, UV 254/220 nm. This resulted in 3.1 mg (3%) of the title compound as a white solid. LC-MS (ESI, m/z): $[M+H]^+$=627.0. $^1$HNMR (400 MHz, DMSO-$d_6$, ppm): δ 8.23 (s, 1H), 7.91 (s, 1H), 7.44-7.36 (m, 2H), 7.34-7.32 (m, 1H), 4.33-3.75 (brs, 2H), 3.50-3.23 (m, 3H), 2.97-2.88 (m, 1H), 2.69-2.58 (m, 1H), 2.39-2.31 (m, 1H), 2.25-2.18 (m, 1H), 2.03-1.95 (m, 1H), 1.32-1.25 (m, 2H), 1.18-1.02 (m, 5H).

Scheme 10 (Compound II-46)

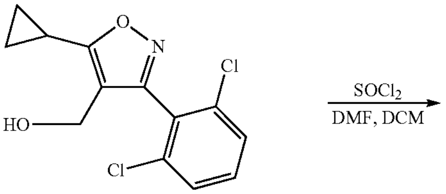

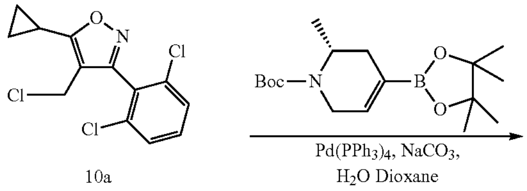

10a

-continued

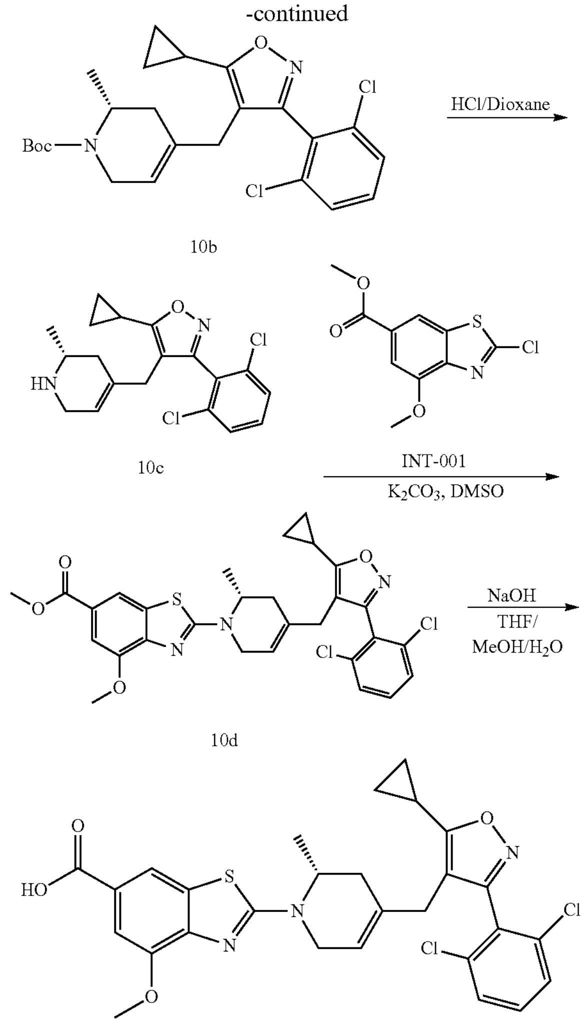

10b

10c

10d

II-46

Experimental Details for Compound II-46 (Scheme 10)

4-(Chloromethyl)-5-cyclopropyl-3-(2,6-dichlorophenyl)-1,2-oxazole (Compound 10a)

To a solution of [5-cyclopropyl-3-(2,6-dichlorophenyl)-1,2-oxazol-4-yl]methanol (1 g, 3.52 mmol) in DCM (7 mL) was added $SOCl_2$ (460 mg, 3.87 mmol) and DMF (2 drops). The resulting solution was stirred for 1 h at room temperature. The reaction was quenched by the addition of water. The resulting mixture was diluted with DCM and washed with water and brine. The mixture was dried over anhydrous sodium sulfate. The mixture was concentrated under vacuum. The residue was applied onto a silica gel column with ethyl acetate/petroleum ether (1:5). This resulted in 1 g (94%) of the title compound as an orange oil. LCMS (ESI, m/z): $[M+H]^+$=302.1.

(R)-tert-Butyl 4-((3-(2,6-dichlorophenyl)-5-cyclopropylisoxazol-4-yl)methyl)-5,6-dihydro-6-methylpyridine-1(2H)-carboxylate (Compound 10b)

To a solution of tert-butyl(2R)-2-methyl-4-(tetramethyl-1,3,2-dioxaborolan-2-yl)-1,2,3,6-tetrahydropyridine-1-carboxylate ((220 mg, 0.68 mmol) in a mixture of dioxane (3 mL) and $H_2O$ (1 mL) was added Compound 10a (280 mg, 0.93 mmol), $Pd(PPh_3)_4$(20 mg, 0.02 mmol) and $Na_2CO_3$ (231 mg, 2.16 mmol). The resulting solution was stirred for 3 h at 80° C. under $N_2$ atmosphere. The mixture was diluted with ethyl acetate and washed with water and brine. The mixture was concentrated under vacuum after dried over anhydrous sodium sulfate. The residue was applied onto a silica gel column with ethyl acetate/petroleum ether (1:4). This resulted in 80 mg (crude product) of the title compound as an orange oil. LCMS (ESI, m/z): $[M+H]^+$=463.3.

(2R)-4-[[5-Cyclopropyl-3-(2,6-dichlorophenyl)-1,2-oxazol-4-yl]methyl]-2-methyl-1,2,3,6-tetrahydropyridine (Compound 10c)

To a solution of Compound 10b (50 mg, 0.11 mmol) in dioxane (4 mL) was added a solution of hydrogen chloride in dioxane (6 mL, 4M). The resulting solution was stirred for 1 h at room temperature. The mixture was concentrated under vacuum. This resulted in 35 mg (89%) of the title compound as a light yellow oil. LCMS (ESI, m/z): $[M+H]^+$=363.2.

Methyl 2-[(2R)-4-[[5-cyclopropyl-3-(2,6-dichlorophenyl)-1,2-oxazol-4-yl]methyl]-2-methyl-1,2,3,6-tetrahydropyridin-1-yl]-4-methoxy-1,3-benzothiazole-6-carboxylate (Compound 10d)

To a solution of methyl 2-chloro-4-methoxy-1,3-benzothiazole-6-carboxylate (100 mg, 0.33 mmol) in DMSO (3 mL) was added $K_2CO_3$ (138 mg, 0.99 mmol) and Compound 10c (120 mg, 0.33 mmol). The resulting solution was stirred for 3 h at 120° C. The reaction was quenched by the addition of water. The resulting mixture was extracted with ethyl acetate several times. The organic layers were combined and washed with water and brine. The residue was dried over anhydrous sodium sulfate. The mixture was concentrated under vacuum. The residue was applied onto a silica gel column with ethyl acetate/petroleum ether (1:1). This resulted in 50 mg (26%) of the title compound as a yellow solid. LCMS (ESI, m/z): $[M+H]^+$=584.2.

2-[(2R)-4-[[5-Cyclopropyl-3-(2,6-dichlorophenyl)-1,2-oxazol-4-yl]methyl]-2-methyl-1,2,3,6-tetrahydropyridin-1-yl]-4-methoxy-1,3-benzothiazole-6-carboxylic acid (Compound II-46)

To a solution of Compound 10d (30 mg, 0.05 mmol) in a mixture of methanol (1 mL) and tetrahydrofuran (1 mL) was added a solution of sodium hydroxide (10 mg, 0.25 mmol) in water (1 mL). The resulting solution was stirred for 2 h at 50° C. The pH value of the solution was adjusted to 6-7 with hydrogen chloride (2 N). The resulting mixture was concentrated under vacuum. The residue was applied onto a reversed column with ACN:$H_2O$ (4:6). This resulted in 2 mg (7%) of the title compound as a white solid. LCMS (ESI, m/z): $[M+H]^+$=570.3. $^1H$ NMR (400 MHz, DMSO-$d_6$, ppm): δ 8.00-7.98 (m, 1H), 7.64-7.52 (m, 3H), 7.38 (s, 1H), 5.15 (s, 1H), 5.03 (s, 1H), 4.30 (s, 1H), 3.97 (s, 3H), 3.22-2.97 (m, 3H), 2.29-2.25 (m, 1H), 2.18-2.12 (m, 1H), 1.90-1.78 (m, 1H), 1.13-1.06 (m, 7H).

Scheme 11 (Compound VII-01)

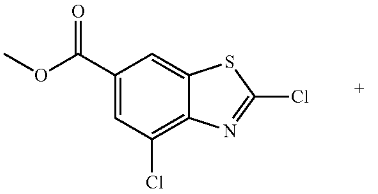
+

INT-008

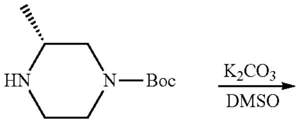

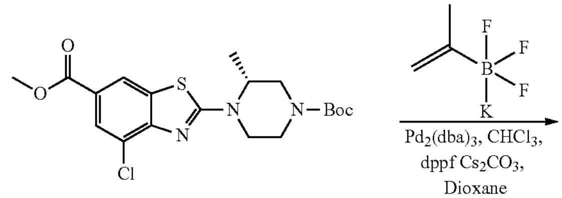

11a

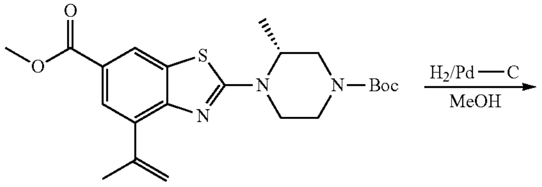

11b

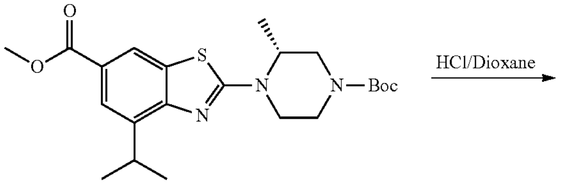

11c

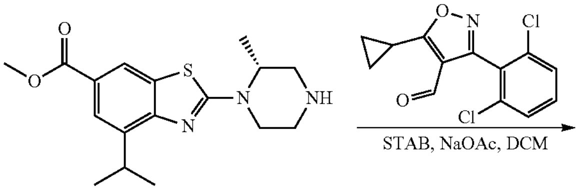

11d

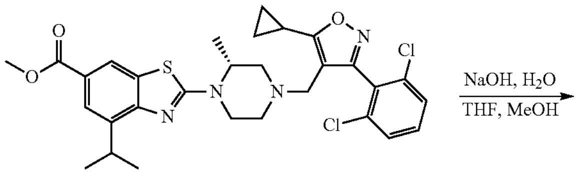

11e

-continued

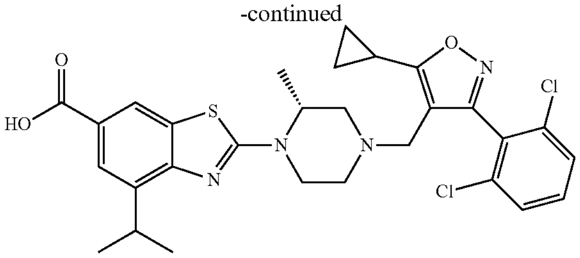

VII-01

Experimental Details for Compound VII-01 (Scheme 11)

(R)-Methyl 2-(4-(tert-butoxycarbonyl)-2-methylpiperazin-1-yl)-4-chlorobenzo[d]thiazole-6-carboxylate (Compound 11a)

To a solution of methyl 2,4-dichloro-1,3-benzothiazole-6-carboxylate (50 mg, 0.19 mmol) in DMSO (2 mL) was added tert-butyl (3R)-3-methylpiperazine-1-carboxylate (38 mg, 0.19 mmol) and potassium carbonate (79 mg, 0.57 mmol). The mixture was stirred for 2 h at 120° C. The reaction solution was diluted with ethyl acetate. The resulted mixture was washed with water and brine. The mixture was dried over anhydrous sodium sulfate and concentrated under vacuum. The residue was applied onto a silica gel column with ethyl acetate/petroleum ether (27:73). This resulted in 30 mg (37%) of the title compound as a white solid. LCMS (ESI, m/z): $[M+H]^+$=426.3.

(R)-Methyl 2-(4-(tert-butoxycarbonyl)-2-methylpiperazin-1-yl)-4-(prop-1-en-2-yl)benzo[d]thiazole-6-carboxylate (Compound 11b)

To a solution of Compound 11a (30 mg, 0.07 mmol) in dioxane (1 mL) was added potassium isopropenyltrifluoroborate (31 mg, 0.21 mmol), $Pd_2(dba)_3.CHCl_3$ (4 mg, 0.005 mmol), dppf (4 mg, 0.01 mmol) and cesium carbonate (69 mg, 0.21 mmol). The mixture was stirred for 3 h at 150° C. under $N_2$ atmosphere. The mixture was diluted with ethyl acetate and further washed with water and brine. The mixture was dried over anhydrous sodium sulfate and concentrated under vacuum. The residue was applied onto a silica gel column with ethyl acetate/petroleum ether (1:4). This resulted in 30 mg (crude) of the title compound as a solid. LCMS (ESI, m/z): $[M+H]^+$=432.0

(R)-Methyl 2-(4-(tert-butoxycarbonyl)-2-methylpiperazin-1-yl)-4-isopropylbenzo[d]thiazole-6-carboxylate (Compound 11c)

To a solution of Compound 11b (30 mg, 0.07 mmol) in methanol (2 mL) was added Pd—C (15 mg, 10%, w %). The mixture solution was stirred for 2 h at room temperature under $H_2$ atmosphere. The filtrate was concentrated under vacuum after filtration. This resulted in 28 mg (93%) of the title compound as a white solid. LCMS (ESI, m/z): $[M+H]^+$=434.2.

(R)-Methyl 4-isopropyl-2-(2-methylpiperazin-1-yl) benzo[d]thiazole-6-carboxylate (Compound 11d)

To a solution of Compound 11c (30 mg, 0.07 mmol) in dioxane (2 mL) was added a solution of hydrogen chloride in dioxane (2 mL, 4M). The mixture was stirred for 1 h at room temperature. The mixture was concentrated under vacuum. This resulted in 20 mg (87%) of the title compound. LCMS (ESI, m/z): $[M+H]^+$=334.2.

(R)-Methyl 2-(4-((5-cyclopropyl-3-(2,6-dichloro-phenyl) isoxazol-4-yl)methyl)-2-methylpiperazin-1-yl)-4-isopropylbenzo[d]thiazole-6-carboxylate (Compound 11e)

To a solution of Compound 1 d (20 mg, 0.06 mmol) in dichloromethane (1 mL) was added 5-cyclopropyl-3-(2,6-dichlorophenyl)-4,5-dihydro-1,2-oxazole-4-carbaldehyde (20 mg, 0.07 mmol) and sodium acetate (6 mg, 0.07 mmol). The mixed was stirred for 30 min at room temperature then $NaBH(OAc)_3$ (40 mg, 0.24 mmol) was added. The reaction was stirred overnight at room temperature. The resulting mixture was diluted with DCM and washed with water and brine. The residue was dried over anhydrous sodium sulfate and concentrated under vacuum. The residue was applied onto a silica gel column with ethyl acetate/petroleum ether (1:3). This resulted in 35 mg (97%) of the title compound as a white solid. LCMS (ESI, m/z): $[M+H]^+$=599.3.

(R)-2-(4-((5-Cyclopropyl-3-(2,6-dichlorophenyl) isoxazol-4-yl)methyl)-2-methylpiperazin-1-yl)-4-isopropylbenzo[d]thiazole-6-carboxylic acid (Compound VII-01)

To a solution of Compound 11e (35 mg, 0.06 mmol) in a mixed solution of THF (1 mL), methanol (1 mL) and water (1 mL) was added sodium hydroxide (12 mg, 0.30 mmol). The resulting mixture was stirred for 1 h at 50° C. The pH value of the solution was adjusted to 6 with hydrogen chloride (2 N). The mixture was concentrated under vacuum. The residue was applied onto a C18 gel column with $ACN/H_2O$ (62:38). This resulted in 6.8 mg (20%) of the title compound as a white solid. LCMS (ESI, m/z): $[M+H]^+$=585.1. $^1$HNMR (400 MHz, DMSO-$d_6$, ppm): δ 8.18-8.17 (m, 1H), 7.83-7.72 (m, 1H), 7.66-7.64 (m, 2H), 7.57-7.55 (m, 1H), 4.18-4.17 (m, 1H), 3.79-3.78 (m, 1H), 3.56-3.51 (m, 1H), 3.29-3.17 (m, 3H), 2.82-2.79 (m, 1H), 2.68-2.60 (m, 1H), 2.38-2.34 (m, 1H), 2.28-2.24 (m, 1H), 1.97-1.92 (m, 1H), 1.27-1.25 (m, 6H), 1.18-1.09 (m, 4H), 0.98-0.95 (m, 3H).

Following the procedure described above for Scheme 4-9 and substituting the appropriate reagents, starting materials and purification methods known to those skilled in the art, the following compounds of the present invention were prepared.

TABLE 2

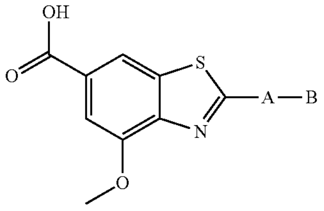

| Compound | A* | B | Scheme | LC-MS $(M + H)^+$ | $^1$HNMR (ppm) |
|---|---|---|---|---|---|
| II-01 | 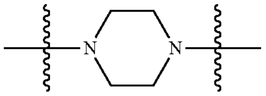 | 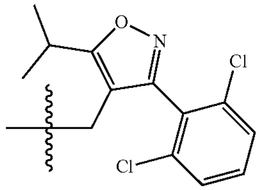 [SMILES: *Cc1c(-c2c(Cl)cccc2Cl)noc1C(C)C] | 4 | 561.2 | $CD_3OD-d_4$: δ 8.05 (s, 1H), 7.68-7.54 (m, 4H), 4.25 (s, 2H), 4.02 (s, 3H), 3.62-3.60 (m, 1H), 3.34-3.32 (m, 8H), 1.49 (d, J = 6.9 Hz, 6H). |
| II-02 | 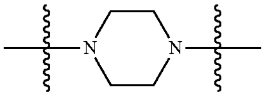 [SMILES: *N1CCN(*)CC1] | 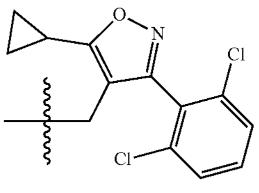 [SMILES: *Cc1c(-c2c(Cl)cccc2Cl)noc1C1CC1] | 4 | 559.2 | DMSO-$d_6$: δ 7.99 (s, 1H), 7.65-7.62 (m, 2H), 7.58-7.53 (m, 1H), 7.39 (d, J = 1.2 Hz, 1H), 3.89 (s, 3H), 3.40 (brs, 4H), 3.34 (s, 2H), 2.38-2.34 (m, 5H), 1.18-1.09 (m, 4H). |
| II-04 | 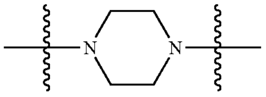 | 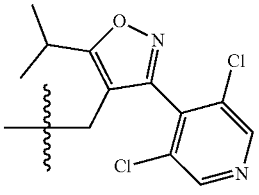 [SMILES: *Cc1c(-c2c(Cl)cncc2Cl)noc1C(C)C] | 4 | 562.1 | DMSO-$d_6$: δ 12.75 (s, 1H), 8.83 (m, 2H), 7.99 (m, 1H), 7.38 (s, 1H), 3.88 (s, 3H), 3.52-3.34 (m, 7H), 2.36 (s, 4H), 1.35-1.33 (d, J = 7.2 Hz, 6H). |

TABLE 2-continued

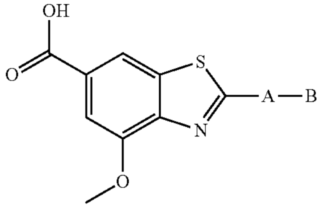

| Compound | A* | B | Scheme | LC-MS (M + H)$^+$ | $^1$HNMR (ppm) |
|---|---|---|---|---|---|
| II-05 | 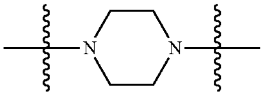 [SMILES: *N1CCN(*)CC1] | 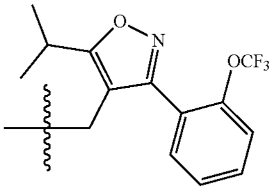 [SMILES: *Cc1c(-c2ccccc2OC(F)(F)F)noc1C(C)C] | 4 | 577.3 | DMSO-$d_6$: δ 12.75 (s, 1H), 7.99 (s, 1H), 7.71-7.64 (m, 2H), 7.55-7.53 (m, 2H), 7.38 (s, 1H), 3.88 (s, 3H), 3.56-3.32(m, 7H), 2.35 (brs, 4H), 1.34-1.23 (d, J = 6.8 Hz, 6H). |
| II-06 | 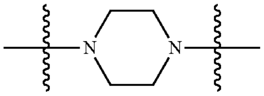 [SMILES: *N1CCN(*)CC1] | 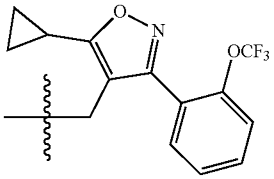 [SMILES: *Cc1c(-c2ccccc2OC(F)(F)F)noc1C1CC1] | 4 | 574.9 | DMSO-$d_6$: δ 7.97 (s, 1H), 7.73-7.71 (m, 1H), 7.67-7.65 (m, 1H), 7.63-7.54 (m, 2H), 7.38 (s, 1H), 3.87 (s, 3H), 3.40-3.32 (m, 6H), 2.37-2.33 (m, 5H), 1.14-1.07 (m, 4H). |
| II-08 | 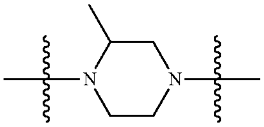 [SMILES: *N1CCN(*)C(C)C1] | 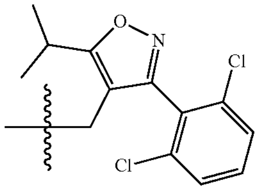 [SMILES: *Cc1c(-c2c(Cl)cccc2Cl)noc1C(C)C] | 4 | 575.1 | DMSO-$d_6$,: δ12.68 (brs, 1H), 7.97 (d, J = 1.5 Hz, 1H), 7.66-7.63 (m, 2H), 7.57-7.51 (m, 1H), 7.37 (d, J = 1.5 Hz, 1H), 4.12 (brs, 1H), 3.87 (s, 3H), 3.74-3.70 (m, 1H), 3.38-3.34 (m, 1H), 3.21-3.16 (m, 3H), 2.78-2.73 (m, 1H), 2.57-2.55 (m, 1H), 2.23-2.18 (m, 1H), 1.87-1.86 (m, 1H), 1.36-1.32 (m, 6H), 0.93-0.91 (d, J = 6.6 Hz, 3H). |
| II-09 | 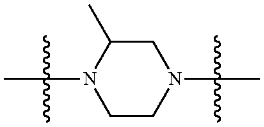 | 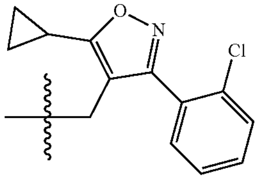 [SMILES: *Cc1c(-c2ccccc2Cl)noc1C1CC1] | 4 | 573.3 | $CD_3OD$-$d_4$: δ7.98 (s, 1H), 7.57-7.46 (m, 4H), 4.24 (brs, 1H), 3.99 (s, 3H), 3.88-3.84 (m, 1H), 3.34 (s, 2H), 2.93-2.90(m, 1H), 3.66 (d, J = 10.8 Hz, 1H), 2.35-2.29 (m, 2H), 2.04-1.94 (m, 2H), 1.19 (t, J = 2 Hz, 4H), 1.08 (d, J = 7.8 Hz, 3H). |
| II-10 | 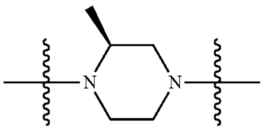 [SMILES: *N1CCN(*)[C@@H](C)C1] | 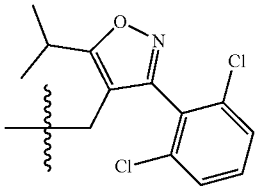 [SMILES: *Cc1c(-c2c(Cl)cccc2Cl)noc1C(C)C] | 4 | 575.2 | DMSO-$d_6$: δ 12.73 (s, 1H), 7.98 (s, 1H), 7.66-7.63 (m, 2H), 7.57-7.52 (m, 1H), 7.37 (s, 1H), 4.20-4.10 (m, 1H), 3.88 (s, 3H), 3.80-3.68 (m, 1H), 3.42-3.35 (m, 1H), 3.25-3.1 (m, 3H), 2.81-2.72 (m, 1H), 2.60-2.55 (m, 1H), 2.25-2.15 (m, 1H), 1.92-1.80 (m, 1H), 1.40-1.30 (m, 6H), 0.93 (d, J = 6.6 Hz, 3H). |
| II-11 | 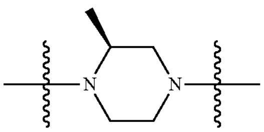 [SMILES: *N1CCN(*)[C@@H](C)C1] | 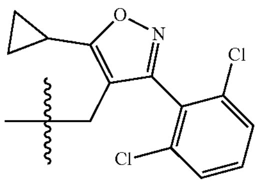 [SMILES: *Cc1c(-c2c(Cl)cccc2Cl)noc1C1CC1] | 4 | 573.2 | DMSO-$d_6$: δ 12.75 (s, 1H), 8.00 (s, 1H), 7.66-7.50 (m, 3H), 7.38 (s, 1H), 4.21-4.09 (m, 1H), 3.89 (s, 3H), 3.82-3.74 (s, 1H), 3.40-3.33 (m, 2H), 3.23-3.10 (m, 1H), 2.85-2.75 (m, 1H), 2.60-2.54 (m, 1H), 2.40-2.30 (m, 1H), 2.28-2.20 (m, 1H), 1.98-1.86 (m, 1H), 1.22-1.10 (m, 4H), 0.95 (d, J = 6.6 Hz, 3H). |

TABLE 2-continued
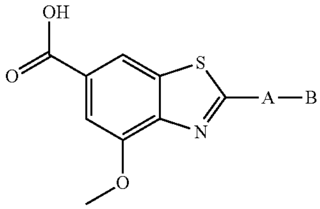
| Compound | A* | B | Scheme | LC-MS (M + H)$^+$ | $^1$HNMR (ppm) |
|---|---|---|---|---|---|
| II-12 | 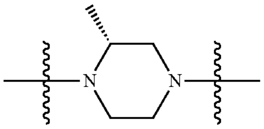 [SMILES: *N1CCN(*)[C@H](C)C1] | 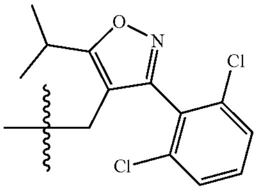 [SMILES: *Cc1c(-c2c(Cl)cccc2Cl)noc1C(C)C] | 4 | 575.2 | DMSO-$d_6$: δ 7.96-7.95 (m, 1H), 7.65-7.63 (m, 2H), 7.56-7.51 (m, 1H), 7.38-7.37 (m, 1H), 4.14-4.13 (m, 1H), 3.88 (s, 3H), 3.75-3.72 (m, 1H), 3.43-3.40 (m, 1H), 3.31-3.12 (m, 3H), 2.78-2.74 (m, 1H), 2.51-2.50 (m, 1H), 2.27-2.19 (m, 1H), 1.91-1.83 (m, 1H), 1.36-1.34 (m, 6H), 0.91 (d, J = 6.5 Hz, 3H). |
| II-13 | 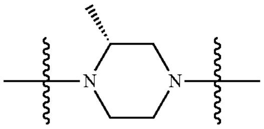 [SMILES: *N1CCN(*)[C@H](C)C1] | 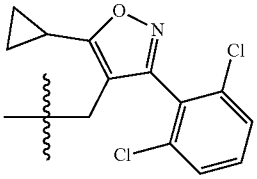 [SMILES: *Cc1c(-c2c(Cl)cccc2Cl)noc1C1CC1] | 4 | 573.2 | DMSO-$d_6$: δ 12.75 (s, 1H), 7.99 (d, J = 1.2 Hz, 1H), 7.65 (d, J = 8.0 Hz, 2H), 7.57-7.53 (m, 1H), 7.37 (d, J = 1.2 Hz, 1H), 4.31-4.12 (m, 1H), 3.88 (s, 3H), 3.81-3.61 (m, 1H), 3.29-3.28 (m, 2H), 3.18-3.11 (m, 1H), 2.82-2.80 (m, 1H), 2.59-2.50 (m, 1H), 2.36-2.34 (m, 1H), 2.25-2.23 (m, 1H), 1.93-1.92 (m, 1H), 1.15-1.11 (m, 4H), 0.99-0.90 (m, 3H). |
| II-14 | 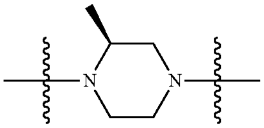 [SMILES: *N1CCN(*)[C@@H](C)C1] | 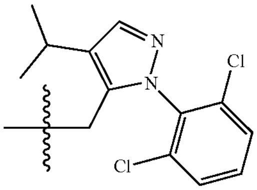 [SMILES: *Cc1c(C(C)C)cnn1-c1c(Cl)cccc1Cl] | 4 | 574.3 | DMSO-$d_6$: δ 12.62 (s, 1H), 7.98 (s, 1H), 7.69-7.67 (m, 3H), 7.57-7.52 (m, 1H), 7.37(s, 1H), 4.16 (s, 1H), 3.87 (s, 3H).3.75-3.71 (m, 1H), 3.35-3.32 (m, 2H), 3.24-3.17(m, 1H), 3.00-2.96 (m, 1H), 2.76-2.73 (m, 1H), 2.44 (s, 1H), 2.26-2.22 (m, 1H), 1.93-1.87 (m, 1H), 1.27-1.21 (m, 6H), 1.21-0.71 (m, 3H). |
| II-15 | 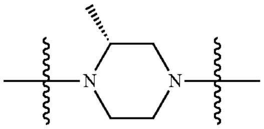 [SMILES: *N1CCN(*)[C@H](C)C1] | 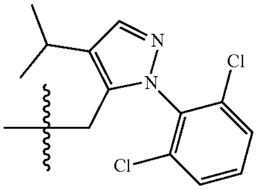 [SMILES: *Cc1c(C(C)C)cnn1-c1c(Cl)cccc1Cl] | 4 | 574.2 | DMSO-$d_6$: δ 7.96 (d, J = 1.6 Hz, 1H), 7.70-7.68 (m, 3H), 7.58-7.54 (m, 1H), 7.38 (d, J = 1.6 Hz, 1H), 4.15 (s, 1H), 3.88 (s, 3H), 3.74-3.69 (m, 1H), 3.39-3.32 (m, 2H), 3.24-3.17 (m, 1H), 3.02-2.95 (m, 1H), 2.76-2.68 (m, 1H), 2.48-2.45 (m, 1H), 2.34-2.23 (m, 1H), 1.94-1.87 (m, 1H), 1.28-1.22 (m, 6H), 0.92 (d, J = 6.8 Hz, 3H). |
| II-16 | 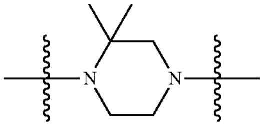 [SMILES: *N1CCN(*)C(C)(C)C1] | 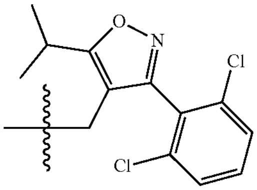 [SMILES: *Cc1c(-c2c(Cl)cccc2Cl)noc1C(C)C] | 4 | 589.3 | DMSO-$d_6$: δ 12.8 (s, 1H), 8.01 (s, 1H), 7.64 (d, J = 8.0 Hz, 2H), 7.55-.51 (m, 1H), 7.39 (s, 1H), 3.91 (s, 3H), 3.41-3.35 (m, 1H), 3.22(s, 2H), 2.90 (s, 1H), 2.74 (s, 1H), 2.39 (s, 2H), 2.19 (s, 2H), 1.36-1.33 (m, 12H). |

TABLE 2-continued

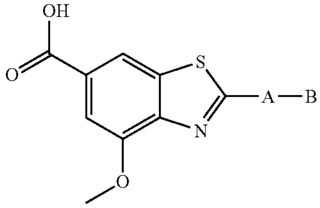

| Compound | A* | B | Scheme | LC-MS (M + H)+ | $^1$HNMR (ppm) |
|---|---|---|---|---|---|
| II-17 | 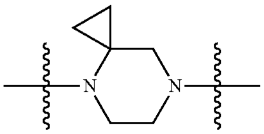 [SMILES: *N1CCN(*)C2(CC2)C1] | 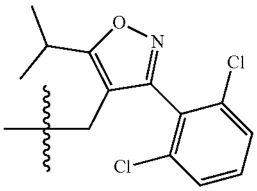 [SMILES: *Cc1c(-c2c(Cl)cccc2Cl)noc1C(C)C] | 4 | 587.3 | $CD_3OD-d_4$: δ 8.02-7.99 (m, 1H), 7.61-7.46 (m, 4H), 4.00 (s, 3H), 3.40-3.33 (m, 3H), 2.52-2.10 (m, 4H), 3.24 (s, 2H), 1.41 (d, J = 6.9 Hz, 6H), 1.15-1.00 (m, 2H), 0.75-0.65 (m, 2H). |
| II-18 | 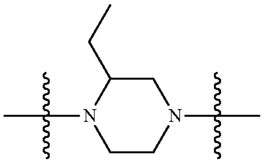 [SMILES: *N1CCN(*)C(CC)C1] | 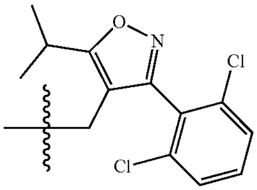 [SMILES: *Cc1c(-c2c(Cl)cccc2Cl)noc1C(C)C] | 4 | 589.2 | DMSO-$d_6$: δ 12.72 (s, 1H), 7.96 (s, 1H), 7.66-7.50 (m, 3H), 7.37 (s, 1H), 3.88 (s, 3H), 3.86-3.75 (m, 2H), 3.41-3.30 (m, 1H), 3.28-3.00 (m, 3H), 2.77-2.62 (m, 2H), 2.16-2.11 (m, 1H), 1.89-1.78 (m, 1H), 1.42-1.30 (m, 8H), 0.62 (t, J = 7.5 Hz, 3H). |
| II-19 | 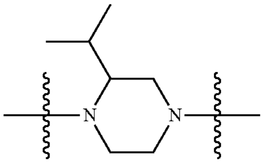 [SMILES: *N1CCN(*)C(C(C)C)C1] | 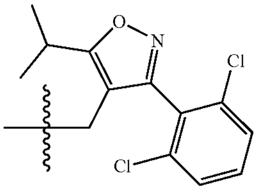 [SMILES: *Cc1c(-c2c(Cl)cccc2Cl)noc1C(C)C] | 4 | 603.2 | DMSO-$d_6$: δ 12.75 (s, 1H), 7.96 (s, 1H), 7.69-7.50 (m, 3H), 7.36 (s, 1H), 4.10-3.93 (m, 1H), 3.87 (s, 3H), 3.60-3.33 (m, 2H), 3.30-3.03 (m, 3H), 2.88-2.68 (m, 2H), 2.10-2.00 (m, 1H), 1.92-1.75 (m, 2H), 1.33 (t, J = 6.6 Hz, 6H), 0.70 (d, J = 6.9 Hz, 3H), 0.61 (d, J = 6.6 Hz, 3H). |
| II-20 | 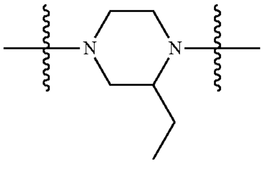 | 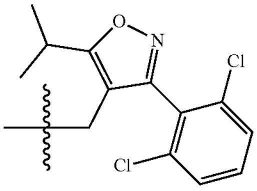 [SMILES: *Cc1c(-c2c(Cl)cccc2Cl)noc1C(C)C] | 4 | 589.1 | DMSO-$d_6$: δ 7.95 (d. J = 1.2 Hz, 1H), 7.65-7.63 (m, 2H), 7.55-7.53 (m, 1H), 7.40 (s, 1H), 3.88 (s, 3H), 3.66-3.62 (m, 1H), 3.51-3.34 (m, 4H), 3.15-3.07 (m, 1H), 2.72-2.68 (m, 1H), 2.27-2.26 (m, 1H), 2.19-2.16 (m, 1H), 1.42-1.40 (m, 1H), 1.35-1.32 (m, 6H), 1.23-1.20 (m, 1H), 0.66 (t, J = 7.2 Hz, 3H). |
| II-21 | 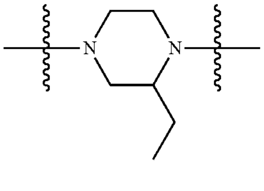 | 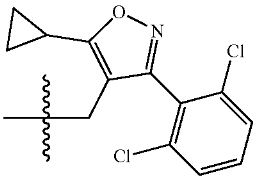 [SMILES: *Cc1c(-c2c(Cl)cccc2Cl)noc1C1CC1] | 4 | 587.3 | DMSO-$d_6$: δ 7.97 (s, 1H), 7.64-7.62 (m, 2H), 7.57-7.53 (m, 1H), 7.40 (s, 1H), 3.88 (s, 3H), 3.68-3.65 (m, 1H), 3.54-3.50 (m, 3H), 3.23-3.09 (m, 2H), 2.77-2.73 (m, 1H), 2.37-2.22 (m, 3H), 1.47-1.43 (m, 1H), 1.25-1.21 (m, 1H), 1.15-1.08 (m, 4H), 0.65 (t, J = 7.6 Hz, 3H). |
| II-23 | 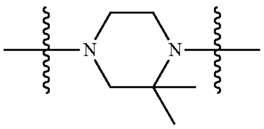 | 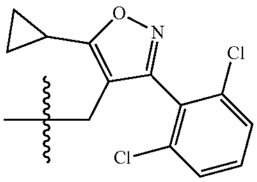 [SMILES: *Cc1c(-c2c(Cl)cccc2Cl)noc1C1CC1] | 6 | 587.2 | DMSO-$d_6$: δ 12.70 (s, 1H), 7.97 (d, J = 1.2 Hz, 1H), 7.64-7.62 (m, 2H), 7.58-7.53 (m, 1H), 7.37 (d, J = 1.6 Hz, 1H), 3.88 (s, 3H), 3.48 (s, 2H), 3.31 (d, J = 4.8 Hz, 2H), 3.02 (s, 2H), 2.50-2.47 (m, 2H), 2.33-2.27(m, 1H), 1.15-1.11 (m, 4H), 0.75 (s, 6H). |

TABLE 2-continued

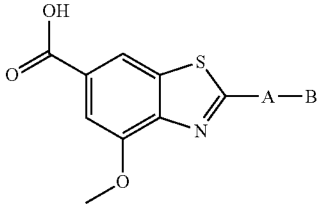

| Com-pound | A* | B | Scheme | LC-MS (M + H)+ | $^1$HNMR (ppm) |
|---|---|---|---|---|---|
| II-24 | 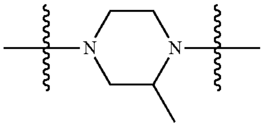 | 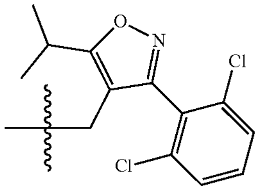 [SMILES: *Cc1c(-c2c(Cl)cccc2Cl)noc1C(C)C] | 6 | 575.2 | DMSO-$d_6$: δ12.73 (s, 1H), 7.98 (d, J = 1.2 Hz, 1H), 7.64-7.62 (m, 2H), 7.57-7.53(m, 1H), 7.38 (d, J = 1.2 Hz, 1H), 3.88 (s, 3H), 3.70-3.55(m, 3H), 3.38-3.33(m, 1H), 3.21-3.16 (m, 1H), 3.00 (d, J = 14 Hz, 1H), 2.71-2.66 (m, 2H), 2.40-2.34 (m, 1H), 2.13-2.10(m, 1H), 1.34-1.31(m, 6H), 0.75(m, 3H). |
| II-25 | 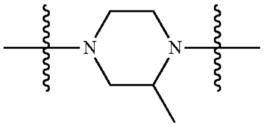 | 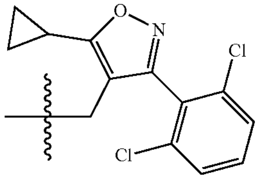 [SMILES: *Cc1c(-c2c(Cl)cccc2Cl)noc1C1CC1] | 6 | 573.3 | DMSO-$d_6$: δ 12.75 (s, 1H), 7.99 (s, 1H), 7.64-7.62 (m, 2H), 7.57-7.53 (m, 1H), 7.38 (d, J = 0.8 Hz, 1H), 3.88 (s, 3H), 3.72-3.56 (m, 3H), 3.21-3.16 (m, 1H), 3.08 (d, J = 13.6 Hz, 1H), 2.73-2.68 (m, 2H), 2.50 (s, 1H), 2.42-2.13 (m, 2H), 1.23-1.08 (m, 4H), 0.76 (d, J = 6.4 Hz, 3H). |
| II-26 | 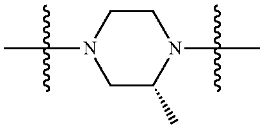 [SMILES: *N1CCN(*)[C@H](C)C1] | 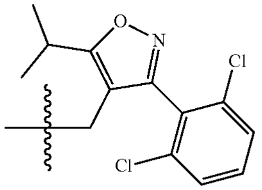 [SMILES: *Cc1c(-c2c(Cl)cccc2Cl)noc1C(C)C] | 6 | 575.2 | DMSO-$d_6$: δ 12.75 (s, 1H), 7.99 (s, 1H), 7.65-7.54 (m, 3H), 7.44-7.38 (m, 1H), 3.89 (s, 3H), 3.70-3.56 (m, 3H), 3.21-3.16 (m, 1H), 2.30-2.27 (m, 1H), 2.71-2.60 (m, 2H), 2.38 (s, 2H), 2.21-2.11 (m, 1H), 1.47-1.32 (m, 6H), 1.75 (s, 3H). |
| II-27 | 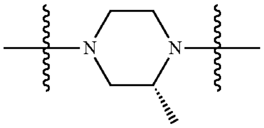 [SMILES: *N1CCN(*)[C@H](C)C1] | 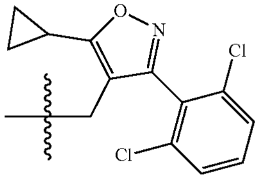 [SMILES: *Cc1c(-c2c(Cl)cccc2Cl)noc1C1CC1] | 4 | 573.0 | $CD_3OD$-$d_4$: δ 7.95 (d, J = 1.2 Hz, 1H), 7.55-7.46 (m, 4H), 3.97 (s, 3H), 3.84 (d, J = 14 Hz, 1H), 3.74-3.69 (m, 2H), 3.29-3.25 (m, 1H), 3.11 (d, J = 14 Hz, 1H), 3.86-3.76 (m, 2H), 2.45-2.42 (m, 1H), 2.28-2.17 (m, 2H), 1.17 (d, J = 6.8 Hz, 4H), 0.85 (d, J = 6.4 Hz, 3H). |
| II-28 | 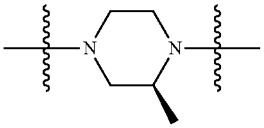 [SMILES: *N1CCN(*)[C@@H](C)C1] | 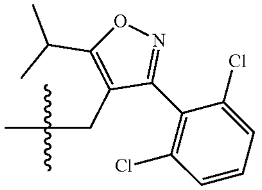 [SMILES: *Cc1c(-c2c(Cl)cccc2Cl)noc1C(C)C] | 4 | 575.1 | DMSO-$d_6$: δ 7.96 (s, 1H), 7.65-7.64 (m, 2H), 7.57-7.55 (m, 1H), 7.39 (m, 1H), 3.87 (s, 3H), 3.68 (m, 4H), 3.16 (s, 1H), 2.99-2.96 (m, 1H), 2.68-2.66 (m, 2H), 2.24 (m, 1H), 2.12 (m, 1H), 1.35-1.31 (m, 6H), 0.75 (s, 3H). |
| II-29 | 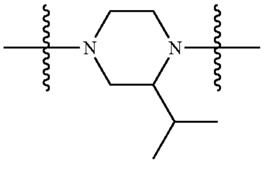 [SMILES: *N1CCN(*)C(C(C)C)C1] | 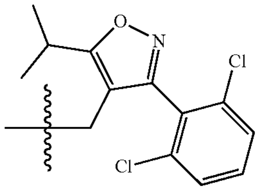 [SMILES: *Cc1c(-c2c(Cl)cccc2Cl)noc1C(C)C] | 4 | 603.2 | DMSO-$d_6$: δ 7.98 (s, 1H), 7.49 (s, 1H), 7.40-7.38 (m, 2H), 7.33-7.30 (m, 1H), 3.92-3.82 (m, 4H), 3.71-3.67 (m, 1H), 3.32-3.23 (m, 2H), 3.09-2.84 (m, 3H), 2.62 (s, 2H), 2.11 (s, 2H), 1.42-1.36 (m, 5H), 0.90 (s, 3H), 0.52 (s, 3H). |

TABLE 2-continued
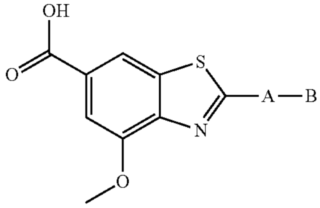
| Compound | A* | B | Scheme | LC-MS $(M + H)^+$ | $^1$HNMR (ppm) |
|---|---|---|---|---|---|
| II-30 | 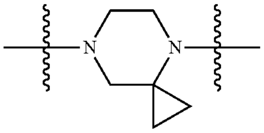 [SMILES: *N1CCN(*)C2(CC2)C1] | 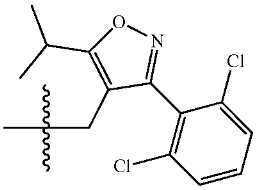 [SMILES: *Cc1c(-c2c(Cl)cccc2Cl)noc1C(C)C] | 6 | 587.0 | DMSO-$d_6$: δ7.95-7.94 (m, 1H), 7.62-7.55 (m, 3H), 7.40-7.38 (m, 1H), 3.87 (s, 3H), 3.67(s, 2H), 3.60-3.50 (m, 2H), 3.40-3.32 (m, 3H), 2.79-2.71 (m, 2H), 1.35 (d, J = 6.9 Hz, 6H), 0.47-0.45 (m, 2H), 0.15-0.18 (m, 2H). |
| II-31 | 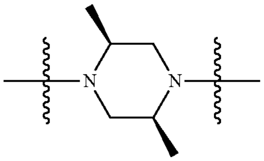 [SMILES: *N1C[C@H](C)N(*)C[C@@H]1C] | 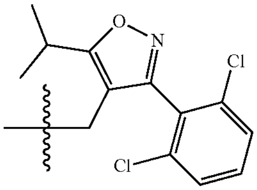 [SMILES: *Cc1c(-c2c(Cl)cccc2Cl)noc1C(C)C] | 4 | 591.3 | $CD_3OD$-$d_4$: δ 8.03 (s, 1H), 7.61-7.59 (m, 3H), 7.58 (m, 1H), 4.39-4.20 (m, 3H), 4.11-4.09 (m, 4H), 3.33-3.32 (m, 1H), 3.12-3.09 (m, 4H), 2.03-1.96 (m, 6H), 1.26-1.24 (m, 3H), 1.15 (s, 3H). |
| II-32 | 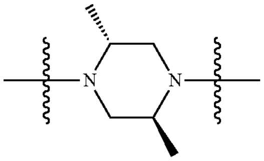 [SMILES: *N1C[C@H](C)N(*)C[C@H]1C] | 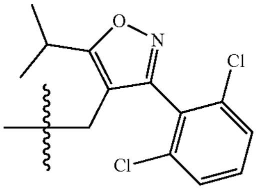 [SMILES: *Cc1c(-c2c(Cl)cccc2Cl)noc1C(C)C] | 4 | 589.2 | DMSO-$d_6$: δ 7.93 (d, J = 1.2 Hz, 1H), 7.64 (d, J = 8.4 Hz, 2H), 7.57-7.55 (m, 1H), 7.37 (d, J = 1.2 Hz, 1H), 4.15 (s, 1H), 3.87 (s, 3H), 3.22-3.57 (m, 5H), 2.91-2.89 (m, 1H), 2.80-2.51 (m, 1H), 2.23-2.19 (m, 1H), 1.37-1.34 (m, 6H), 0.98-0.89 (m, 3H), 0.85-0.75 (m, 3H). |
| II-33 | 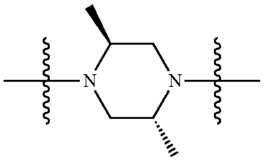 [SMILES: *N1C[C@H](C)N(*)C[C@H]1C] | 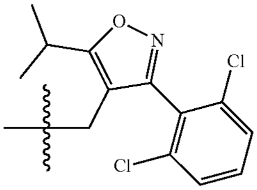 [SMILES: *Cc1c(-c2c(Cl)cccc2Cl)noc1C(C)C] | 4 | 591.2 | DMSO-$d_6$: δ 7.92 (d, J = 1.2 Hz, 1H), 7.88-7.62 (m, 2H), 7.58-7.51 (m, 1H), 7.37 (s, 1H), 4.16 (s, 1H), 3.66 (s, 3H), 3.56-3.38 (m, 3H), 3.28-3.21 (m, 2H), 2.90-2.88 (m, 1H), 2.78-2.74 (m, 1H), 2.23-2.19 (m, 1H), 1.36-1.34 (m, 6H), 0.93 (m, 3H), 0.78 (m, 3H). |
| II-34 | 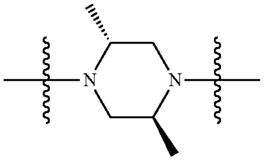 [SMILES: *N1C[C@H](C)N(*)C[C@H]1C] | 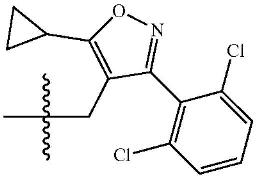 [SMILES: *Cc1c(-c2c(Cl)cccc2Cl)noc1C1CC1] | 6 | 587.2 | $CDCl_3$: δ 8.00 (s, 1H), 7.61-7.51 (m, 1H), 7.50-7.39 (m, 2H), 7.33-6.91 (m, 1H), 4.29 (s, 1H), 4.01 (s, 3H), 3.65-3.61 (m, 1H), 3.54-3.49 (m, 2H), 3.31-3.26 (m, 1H), 3.04-2.90 (m, 1H), 2.89-2.85(m, 1H), 2.26-2.19 (m, 1H), 2.18-2.12 (m, 1H), 1.40-1.21 (m, 2H), 1.20-1.10 (m, 2H), 1.09-1.03 (m, 3H), 0.97-0.90 (m, 3H). |
| II-35 | 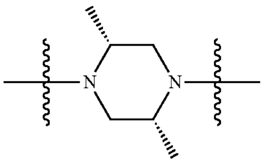 [SMILES: *N1C[C@@H](C)N(*)C[C@H]1C] | 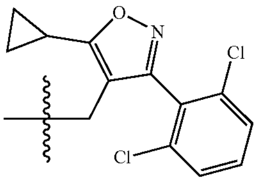 [SMILES: *Cc1c(-c2c(Cl)cccc2Cl)noc1C1CC1] | 6 | 587.1 | DMSO-$d_6$: δ 7.95 (s, 1H), 7.67-7.64 (m, 2H), 7.59-7.55 (m, 1H), 7.41-7.35 (m, 1H), 4.21-4.12 (m, 1H), 3.93-3.86 (m, 4H), 3.70-3.67 (m, 1H), 2.86-2.73 (m, 2H), 2.71-2.62 (m, 1H), 2.42-2.32 (m, 1H), 2.25-2.16 (m, 2H), 1.18-1.08 (m, 7H), 0.91-0.90 (d, J = 6.0 Hz, 3H). |

TABLE 2-continued
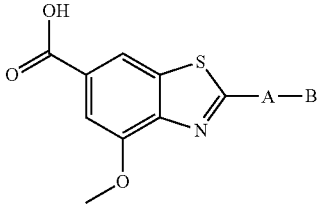
| Compound | A* | B | Scheme | LC-MS (M + H)+ | $^1$HNMR (ppm) |
|---|---|---|---|---|---|
| II-36 | 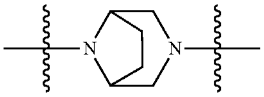 [SMILES: *N1CC2CCC(C1)N2*] | 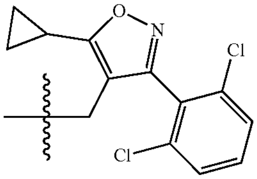 [SMILES: *Cc1c(-c2c(Cl)cccc2Cl)noc1C1CC1] | 4 | 585.0 | $CDCl_3$: δ 7.96 (s, 1H), 7.48-7.41 (m, 1H), 7.39-7.31 (m, 2H), 7.29-7.26 (m, 1H), 4.49-4.31 (m, 2H), 3.89-3.24 (m, 3H), 3.24 (s, 2H), 2.64-2.61 (m, 2H), 2.38-2.35 (m, 2H), 2.16-2.07 (m, 1H), 1.81-1.71 (m, 2H), 1.70-1.68 (m, 2H), 1.23-1.22 (m, 2H), 1.16-1.07 (m, 2H). |
| II-37 | 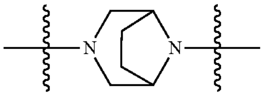 [SMILES: *N1CC2CCC(C1)N2*] | 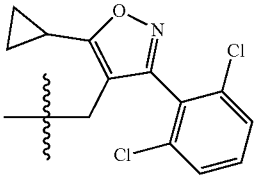 [SMILES: *Cc1c(-c2c(Cl)cccc2Cl)noc1C1CC1] | 6 | 585.1 | $CDCl_3$: δ 8.01 (s, 1H), 7.60-7.51 (m, 1H), 7.40-7.38 (m, 2H), 7.29-7.26 (m, 1H), 4.02 (s, 3H), 3.69-3.66 (m, 2H), 3.49-3.34 (m, 2H), 3.25-3.15 (m, 4H), 2.28-2.19 (m, 1H), 1.86-1.75 (m, 2H), 1.67-1.53 (m, 2H), 1.47-1.21 (m, 2H), 1.19-1.06 (m, 2H). |
| II-38 | 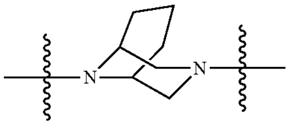 [SMILES: *N1CC2CCCC(C1)N2*] | 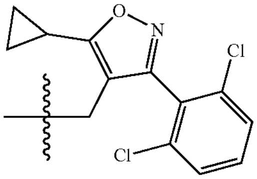 [SMILES: *Cc1c(-c2c(Cl)cccc2Cl)noc1C1CC1] | 4 | 599.2 | DMSO-$d_6$: δ 12.73 (s, 1H), 7.99 (d, J = 1.2 Hz, 1H), 7.65-7.63 (m, 2H), 7.56-7.52 (m, 1H), 7.38 (d, J = 1.2 Hz, 1H), 3.89 (s, 3H), 3.75-3.50 (m, 4H), 3.34-3.33 (m, 2H), 2.74-2.73 (m, 2H), 2.46-2.42 (m, 1H),1.71-1.6 (m, 3H), 1.49-1.47 (m, 2H), 1.36-1.35 (m, 1H), 1.15-1.10 (m, 4H). |
| II-39 | 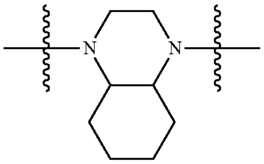 [SMILES: *N1CCN(*)C2CCCCC21] | 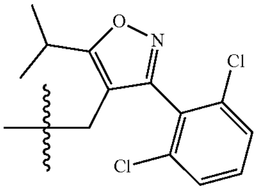 [SMILES: *Cc1c(-c2c(Cl)cccc2Cl)noc1C(C)C] | 4 | 615.2 | DMSO-$d_6$: δ 8.01 (s, 1H), 7.56-7.51 (m, 1H), 7.40-7.32 (m, 3H), 4.15-3.74 (m, 5H), 3.52-3.46 (m, 1H), 3.25-3.20 (m, 1H), 2.94-2.92 (m, 1H), 2.68-2.64 (m, 1H), 2.38-2.30 (m, 1H), 2.12-2.07 (m, 1H), 1.90-1.85 (m, 1H), 1.78-1.63 (m, 1H), 1.40-1.26 (m, 10H), 1.06-0.75 (m, 2H), 0.45-0.36 (m, 1H). |
| II-40 | 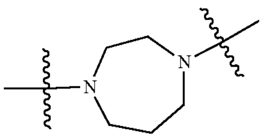 [SMILES: *N1CCCN(*)CC1] | 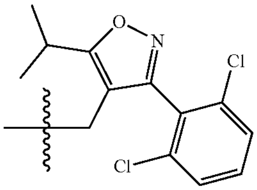 [SMILES: *Cc1c(-c2c(Cl)cccc2Cl)noc1C(C)C] | 4 | 575.3 | DMSO-$d_6$: δ 8.05 (s, 1H), 7.55 (s, 1H), 7.40-7.38 (m, 2H), 7.32-7.30 (m, 1H), 4.05 (s, 3H), 3.68 (s, 3H), 3.37 (s, 2H), 3.32-3.25 (m, 1H), 2.68-2.66 (m, 2H), 2.53-2.50 (m, 2H), 1.83-1.80 (m, 2H), 1.48 (s, 1H), 1.41-1.40 (d, J = 5.3 Hz, 6H). |
| II-41 | 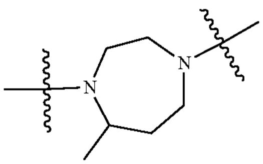 [SMILES: *N1CCC(C)N(*)CC1] | 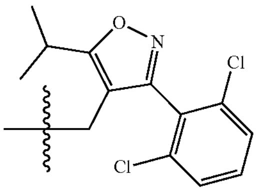 [SMILES: *Cc1c(-c2c(Cl)cccc2Cl)noc1C(C)C] | 4 | 589.2 | $CDCl_3$: δ 8.05-8.00 (m, 1H), 7.61-7.32 (m, 4H), 4.52-3.87 (m, 6H), 3.64-3.17 (m, 3H), 2.89-2.50 (m, 2H), 2.34-1.95 (m, 2H), 1.45-1.17(m, 11H). |

TABLE 2-continued
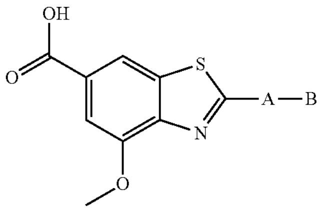
| Compound | A* | B | Scheme | LC-MS (M + H)+ | 1HNMR (ppm) |
|---|---|---|---|---|---|
| II-42 | 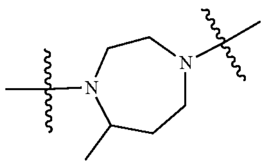 [SMILES: *N1CCC(C)N(*)CC1] | 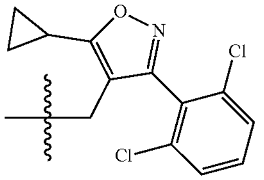 [SMILES: *Cc1c(-c2c(Cl)cccc2Cl)noc1C1CC1] | 4 | 587.2 | $CDCl_3$: δ 8.05 (m, 1H), 7.61-7.57 (m, 1H), 7.51-7.32 (m, 3H), 4.06-3.87 (m, 6H), 3.64-3.40 (m, 1H), 3.39-16 (m, 2H), 2.89-2.53 (m, 3H), 2.50-1.95 (m, 2H), 1.45-1.38 (m, 8H), 1.28-1.17 (m, 3H). |
| II-43 | 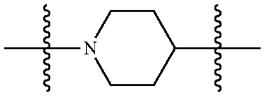 | 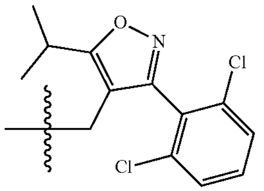 [SMILES: *Cc1c(-c2c(Cl)cccc2Cl)noc1C(C)C] | 7 | 560.1 | $CDCl_3$: δ 8.01 (s, 1H), 7.61 (s, 1H), 7.46-7.34 (m, 3H), 4.19-4.14 (m, 2H), 4.02 (s, 3H), 3.18-3.11 (m, 1H), 3.09-2.96 (m, 2H), 2.25 (d, J = 9.1 Hz, 2H), 1.66 (m, 2H), 1.39 (d, J = 6.2 Hz, 7H), 1.25-1.13 (m, 2H). |
| II-44 | 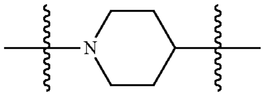 | 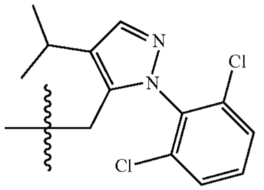 [SMILES: *Cc1c(C(C)C)cnn1-c1c(Cl)cccc1Cl] | 7 | 559.2 | $CD_3OD-d_4$: δ 7.95 (d, J = 1.2 Hz, 1H), 7.68-7.50 (m, 5H), 4.13 (d, J = 13.2 Hz, 2H), 3.97 (s, 3H), 3.03-2.86 (m, 3H), 2.51 (d, J = 7.6 Hz, 2H), 1.68-1.54 (m, 3H), 1.30-1.22 (m, 8H). |
| II-48 | 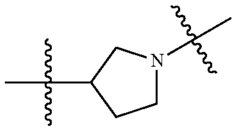 [SMILES: *C1CCN(*)C1] | 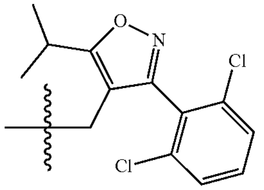 [SMILES: *Cc1c(-c2c(Cl)cccc2Cl)noc1C(C)C] | 8 | 546.3 | $DMSO-d_6$: δ 13.13 (s, 1H), 8.21 (s, 1H), 7.62-7.49 (m, 4H), 3.98 (s, 3H), 3.75 (s, 1H), 3.44-3.40 (m, 2H), 2.73 (s, 3H), 2.29 (s, 2H), 1.98 (s, 1H), 1.33-1.29 (m, 7H). |
| II-49 | 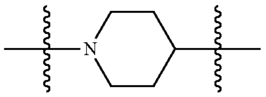 | 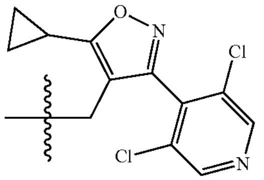 | 7 | 559.2 | $CD_3OD-d_4$: δ 8.75 (s, 2H), 8.02 (d, J = 1.2 Hz, 1H), 7.61 (d, J = 1.2 Hz, 1H), 4.18-4.15 (d, J = 12.0 Hz, 2H), 4.03 (s, 3H), 3.33-3.32 (m, 2H), 2.44-2.42 (d, J = 8.0 Hz, 2H), 2.26-2.20 (m, 1H), 1.82-1.79 (d, J = 12.0 Hz, 2H), 1.63-1.58 (m, 1H), 1.39-1.28 (m, 2H), 1.29-1.26 (d, J = 12.0 Hz, 4H). |
| II-50 | 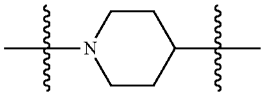 | 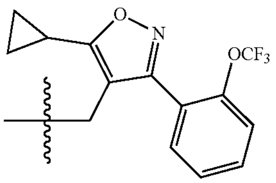 [SMILES: *Cc1c(-c2ccccc2OC(F)(F)F)noc1C1CC1] | 7 | 574.2 | $CD_3OD-d_4$: δ 7.98 (s, 1H), 7.68-7.64 (m, 1H), 7.58-7.51 (m, 4H), 4.12-4.08 (d, J = 12.0 Hz, 2H), 4.00 (s, 3H), 3.08-3.03 (m, 2H), 2.50-2.49 (d, J = 4.0 Hz, 2H), 2.20-2.16 (m, 1H), 1.69-1.66 (d, J = 12.0 Hz, 2H), 1.58-1.54 (m, 1H), 1.28-1.14 (m, 6H). |

TABLE 2-continued

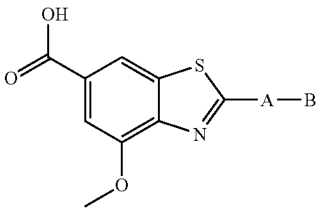

| Compound | A* | B | Scheme | LC-MS (M + H)$^+$ | $^1$HNMR (ppm) |
|---|---|---|---|---|---|
| II-51 | 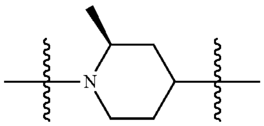 [SMILES: *C1CCN(*)[C@@H](C)C1] | 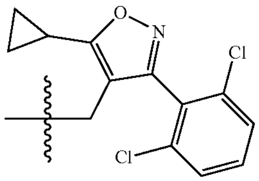 [SMILES: *Cc1c(-c2c(Cl)cccc2Cl)noc1C1CC1] | 7 | 572.1 | DMSO-$d_6$: δ 12.7 (s, 1H), 7.97 (s, 1H), 7.71-7.58 (m, 3H), 7.37 (s, 1H), 4.38 (s, 1H), 3.88 (s, 3H), 3.07-3.26 (m, 1H), 2.14-2.35 (m, 3H), 1.68-1.40 (m, 5H), 1.21-1.00 (m, 8H). |

*It is to be understood that ring A attaches to the thiazole ring at the open valence on the left-hand side of ring A and to the B-ring at the open valence on the right-hand side of ring A.

TABLE 3

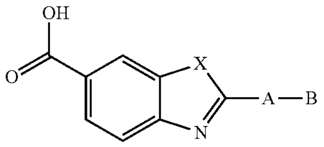

| Compound | A* | B | X | Scheme | LCMS (M + H)$^+$ | $^1$HNMR (ppm) |
|---|---|---|---|---|---|---|
| III-01 | 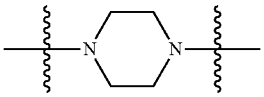 | 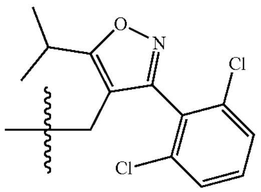 [SMILES: *Cc1c(-c2c(Cl)cccc2Cl)noc1C(C)C] | S | 4 | 531.2 | DMSO-$d_6$: δ 12.62 (s, 1H), 8.36 (s, 1H), 7.86 (d, J = 8.1 Hz, 1H), 7.65-7.53 (m, 3H), 7.46 (d, J = 8.4 Hz, 1H), 3.41 (s, 4H), 3.34 (s, 2H), 3.27 (s, 1H), 2.35 (s, 4H), 1.35 (d, J = 6.9 Hz, 6H). |
| III-02 | 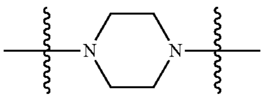 [SMILES: *N1CCN(*)CC1] | 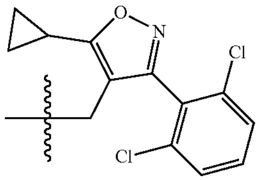 [SMILES: *Cc1c(-c2c(Cl)cccc2Cl)noc1C1CC1] | S | 4 | 531.3 | $CD_3OD-d_4$: δ 8.32 (s, 1H), 7.98-7.95 (m, 1H), 7.58-7.50 (m, 4H), 3.56-3.48 (m, 4H), 3.42 (s, 2H), 2.50-2.46 (m, 4H), 2.34-2.28 (m, 1H), 1.20-1.17 (m, 4H). |
| III-03 | 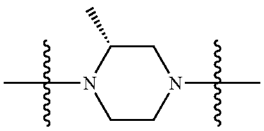 [SMILES: *N1CCN(*)[C@H](C)C1] | 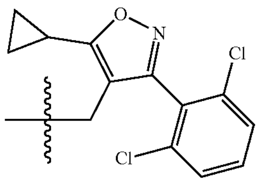 [SMILES: *Cc1c(-c2c(Cl)cccc2Cl)noc1C1CC1] | S | 6 | 543.1 | $CDCl_3$: δ 8.30 (s, 1H), 8.12-7.92 (m, 1H), 7.60-7.46 (m, 1H), 7.41-7.39 (m, 2H), 7.33-7.28 (m, 1H), 4.18 (s, 1H), 3.97-3.71 (m, 1H), 3.48-3.22 (m, 3H), 2.98-2.81 (m, 1H), 2.69-2.53 (m, 1H), 2.25-2.16(m, 1H), 2.21-2.12 (m, 1H), 2.01-1.92 (m, 1H), 1.30-1.21 (m, 2H), 1.18-1.02 (m, 5H). |

TABLE 3-continued

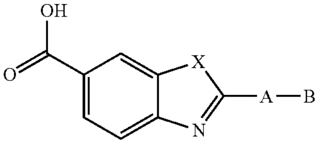

| Compound | A* | B | X | Scheme | LCMS (M + H)$^+$ | $^1$HNMR (ppm) |
|---|---|---|---|---|---|---|
| III-04 | 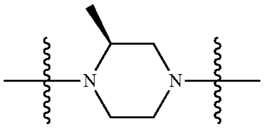 [SMILES: *N1CCN(*)[C@@H](C)C1] | 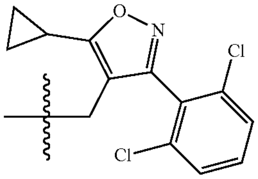 [SMILES: *Cc1c(-c2c(Cl)cccc2Cl)noc1C1CC1] | S | 6 | 543.1 | $CDCl_3$: δ 8.33 (s, 1H), 8.03 (d, J = 8.4 Hz, 1H), 7.51-7.41 (m, 1H), 7.39-7.34 (m, 2H), 7.31-7.26 (m, 1H), 3.82-3.78 (m, 1H), 3.71-3.67 (m, 2H), 3.35-329 (m, 1H), 2.99 (m, 1H), 2.86-2.79 (m, 2H), 2.46-2.42 (m, 1H), 2.20-2.05 (m, 2H), 1.18-1.10 (m, 4H), 0.86 (d, J = 6.3 Hz, 3H). |
| III-05 | 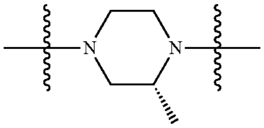 | 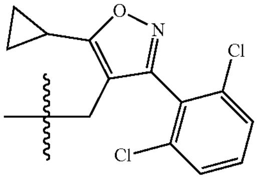 [SMILES: *Cc1c(-c2c(Cl)cccc2Cl)noc1C1CC1] | S | 6 | 543.1 | DMSO-$d_6$: δ 8.31 (s, 1H), 7.82 (d, J = 9.9 Hz, 1H), 7.64-7.57 (m, 2H), 7.55-7.54 (m, 1H), 7.40 (d, J = 8.5 Hz, 1H), 3.72-3.67 (m, 3H), 3.32-3.15 (m, 1H), 3.06 (m, 1H), 2.72-2.70 (m, 2H), 2.62-2.35 (m, 2H), 2.22-2.01 (m, 1H), 1.22-0.95 (m, 4H), 0.75 (d, J = 6 Hz, 3H). |
| III-06 | 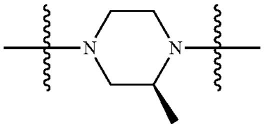 | 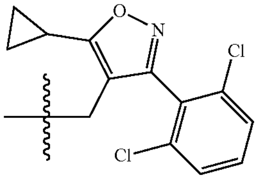 [SMILES: *Cc1c(-c2c(Cl)cccc2Cl)noc1C1CC1] | S | 6 | 543.1 | $CDCl_3$: δ 8.33 (s, 1H), 8.03 (d, J = 8.4 Hz, 1H), 7.51-7.41 (m , 1H), 7.39-7.34 (m, 2H), 7.31-7.26 (m, 1H), 3.82-3.78 (m, 1H), 3.71-3.67 (m, 2H), 3.35-3.29 (m, 1H), 3.02-2.97 (m, 1H), 2.86-2.79 (m, 2H), 2.46-2.42 (m, 1H), 2.20-2.05 (m, 2H), 1.31-1.29 (m, 2H), 1.16-1.03 (m, 2H), 0.86 (d, J = 6.3 Hz, 3H). |
| III-07 | 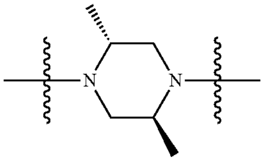 [SMILES: *N1C[C@H](C)N(*)C[C@H]1C] | 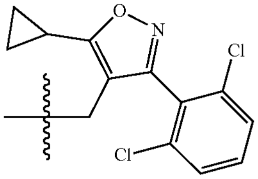 [SMILES: *Cc1c(-c2c(Cl)cccc2Cl)noc1C1CC1] | S | 6 | 557.1 | $CDCl_3$: δ 8.30 (s, 1H), 8.02 (d, J = 8.7 Hz, 1H), 7.48 (d, J = 8.4 Hz, 1H), 7.43-7.31 (m, 2H), 7.30-7.26 (m, 1H), 4.30-4.15(m, 1H), 3.63-3.48 (m, 3H), 3.47-3.28 (m, 1H), 3.06-3.05 (m, 1H), 2.90-2.85 (m, 1H), 2.24-2.20 (m, 1H), 2.19-2.13 (m, 1H), 1.30-1.26 (m, 2H), 1.16-1.05 (m, 5H), 0.92 (d, J = 6.6 Hz, 3H). |
| III-08 | 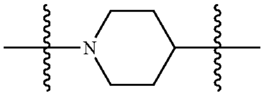 | 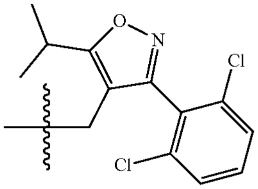 [SMILES: *Cc1c(-c2c(Cl)cccc2Cl)noc1C(C)C] | S | 7 | 530.1 | $CDCl_3$: δ 8.33 (s, 1H), 8.04 (d, J = 8.7 Hz, 1H), 7.54-7.52 (m, 1H), 7.46-7.43 (m, 2H), 7.38-7.33 (m, 1H), 4.16-4.12 (m, 2H), 3.18-2.98 (m, 3H), 2.27 (d, J = 7.2 Hz, 2H), 1.75-1.71 (m, 2H), 1.40-1.31 (m, 7H), 1.25-1.19 (m, 2H). |
| III-09 | 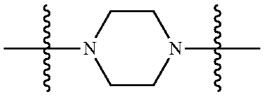 [SMILES: *N1CCN(*)CC1] | 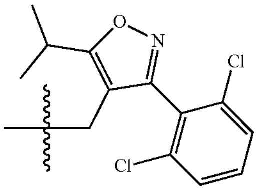 [SMILES: *Cc1c(-c2c(Cl)cccc2Cl)noc1C(C)C] | O | 4 | 515.3 | $CDCl_3$: δ 8.00-7.94 (m, 2H), 7.40-7.32 (m, 4H), 3.55 (brs, 4H), 3.29 (brs, 3H), 2.42 (brs, 4H), 1.43 (d, J = 6.9 Hz, 6H). |

*It is to be understood that ring A attaches to the thiazole/oxazole ring at the open valence on the left-hand side of ring A and to the B-ring at the open valence on the right-hand side of ring A.

TABLE 3I

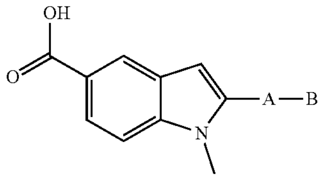

| Compound | A* | B | Scheme | LC-MS (M + H)$^+$ | $^1$HNMR (ppm) |
|---|---|---|---|---|---|
| III2-01 | 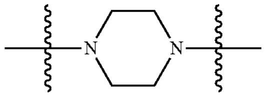 | 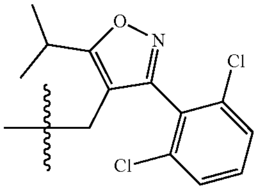 [SMILES: *Cc1c(-c2c(Cl)cccc2Cl)noc1C(C)C] | 6 | 527.3 | DMSO-$d_6$: δ 12.30 (s, 1H), 8.03 (s, 1H), 7.67-7.54 (m, 4H), 7.34 (d, J = 8.7 Hz, 1H), 5.91 (s, 1H), 3.55 (s, 3H), 3.43-3.29 (m, 3H), 2.80 (brs, 4H), 2.42 (brs, 4H), 1.35 (d, J = 6.9 Hz, 6H). |

*It is to be understood that ring A attaches to the pyrrole ring at the open valence on the left-hand side of ring A and to the B-ring at the open valence on the right-hand side of ring A.

TABLE 3II

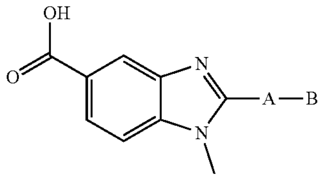

| Compound | A* | B | Scheme | LC-MS (M + H)$^+$ | $^1$HNMR (ppm) |
|---|---|---|---|---|---|
| III3-01 | 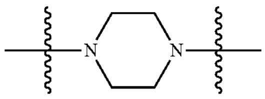 [SMILES: *N1CCN(*)CC1] | 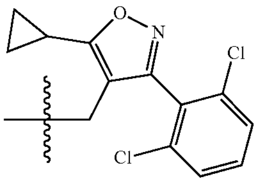 [SMILES: *Cc1c(-c2c(Cl)cccc2Cl)noc1C1CC1] | 4 | 526.3 | DMSO-$d_6$: δ 7.94-7.87 (m, 1H), 7.75-7.53 (m, 4H), 7.40-7.33 (m, 1H), 3.58 (s, 3H), 3.34 (s, 2H), 3.17-3.08 (m, 4H), 2.43-2.23 (m, 5H), 1.15-1.06 (m, 4H). |

*It is to be understood that ring A attaches to the imidazole ring at the open valence on the left-hand side of ring A and to the B-ring at the open valence on the right-hand side of ring A.

TABLE 4

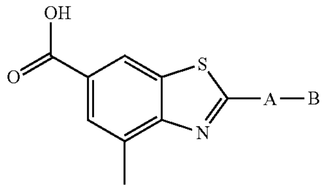

| Compound | A* | B | Scheme | LC-MS (M + H)$^+$ | $^1$HNMR (ppm) |
|---|---|---|---|---|---|
| IV-01 | 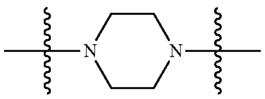 | 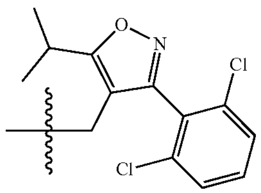 [SMILES: *Cc1c(-c2c(Cl)cccc2Cl)noc1C(C)C] | 4 | 545.3 | DMSO-$d_6$: δ 12.60 (s, 1H), 8.17 (s, 1H), 7.69-7.62 (m, 3H), 7.58-7.52 (m, 1H), 3.34-3.39 (m, 4H), 3.27 (s, 2H), 2.45 (s, 3H), 2.36 (s, 4H), 1.34 (d, J = 6.9 Hz, 6H). |

TABLE 4-continued
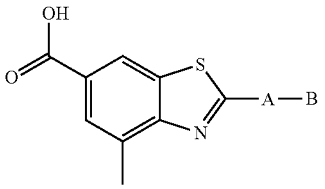
| Compound | A* | B | Scheme | LC-MS $(M + H)^+$ | $^1$HNMR (ppm) |
|---|---|---|---|---|---|
| IV-02 | 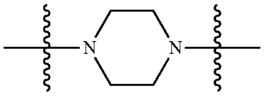 [SMILES: *N1CCN(*)CC1] | 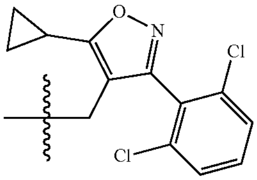 [SMILES: *Cc1c(-c2c(Cl)cccc2Cl)noc1C1CC1] | 4 | 543.1 | DMSO-$d_6$: δ 12.60 (brs, 1H), 8.17-8.16 (m, 1H), 7.69 (s, 1H), 7.65-7.62 (m, 2H), 7.57-7.53 (m, 1H), 3.43-3.41 (m, 4H), 3.41-3.40 (m, 2H), 2.49 (s, 3H), 2.45-2.33 (m, 5H), 1.16-1.11 (m, 4H). |
| IV-03 | 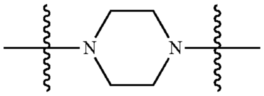 | 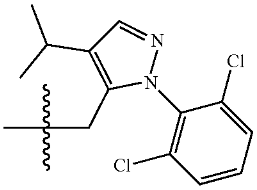 [SMILES: *Cc1c(C(C)C)cnn1-c1c(Cl)cccc1Cl] | 4 | 544.4 | DMSO-$d_6$: δ 8.18 (s, 1H), 7.69-7.67 (m, 4H), 7.59-7.54 (m, 1H), 3.42-3.39 (m, 6H), 3.01-2.95 (m, 1H), 2.45 (s, 3H), 2.34 (brs, 4H), 1.25-1.23 (m, 6H). |
| IV-04 | 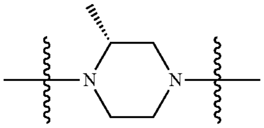 | 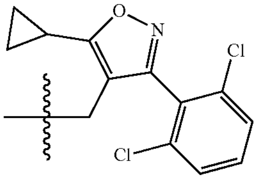 [SMILES: *Cc1c(-c2c(Cl)cccc2Cl)noc1C1CC1] | 6 | 557.1 | DMSO)-$d_6$: δ 12.59 (s, 1H), 8.16 (s, 1H), 7.68-7.62 (m, 3H), 7.56-7.49 (m, 1H), 4.14-4.06 (m, 1H), 3.83 (s, 1H), 3.32 (s, 1H), 3.23-3.13 (m, 2H), 2.82-2.78 (m, 1H), 2.59-2.56 (m, 1H), 2.44 (s, 3H), 2.38-2.30 (m, 1H), 2.26-2.21 (m, 1H), 1.97-1.88 (m, 1H), 1.17-1.08 (m, 4H), 0.97-0.95 (d, J = 6.6 Hz, 3H). |
| IV-05 | 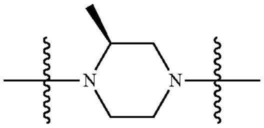 [SMILES: *N1CCN(*)[C@@H](C)C1] | 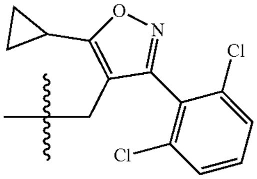 [SMILES: *Cc1c(-c2c(Cl)cccc2Cl)noc1C1CC1] | 6 | 557.3 | DMSO-$d_6$: δ 12.52 (s, 1H), 8.19 (s, 1H), 7.79-7.63 (m, 3H), 7.57-7.51 (m, 1H), 4.08-4.02 (m, 1H), 3.85-3.81 (m, 1H), 3.28-3.15 (m, 3H), 2.90-2.73 (m, 1H), 2.60-2.50 (m, 1H), 2.45-2.37 (m, 4H), 2.27-2.15 (m, 1H), 2.08-1.89 (m, 1H), 1.15-1.03 (m, 4H), 0.96 (d, J = 6.6 Hz, 3H). |
| IV-06 | 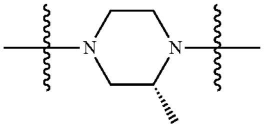 [SMILES: *N1CCN(*)[C@H](C)C1] | 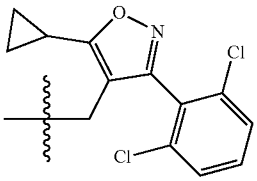 [SMILES: *Cc1c(-c2c(Cl)cccc2Cl)noc1C1CC1] | 6 | 559.1 | DMSO-$d_6$: δ 12.59 (s, 1H), 8.16 (s, 1H), 7.68-7.51 (m, 4H), 3.71-3.57 (m, 3H), 3.24-3.17 (m, 1H), 3.09-3.04 (m, 1H), 2.74-2.68 (m, 2H), 2.44 (s, 3H), 2.32-2.28 (m, 2H), 2.19-2.12 (m, 1H), 1.13-1.06 (m, 4H), 0.76-0.74 (d, J = 6.1 Hz, 3H). |
| IV-07 | 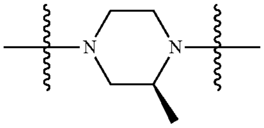 [SMILES: *N1CCN(*)[C@@H](C)C1] | 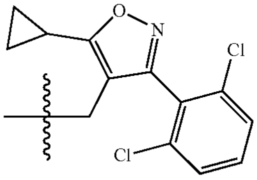 [SMILES: *Cc1c(-c2c(Cl)cccc2Cl)noc1C1CC1] | 6 | 557.3 | DMSO-$d_6$: δ 12.59 (brs, 1H), 8.16 (s, 1H), 7.68 (s, 1H), 7.64-7.61 (m, 2H), 7.57-7.52 (m, 1H), 3.82-3.57 (m, 3H), 3.24-3.16 (m, 1H), 3.09-3.04 (m, 1H), 2.75-2.65 (m, 2H), 2.44-2.35 (m, 4H), 2.33-2.26 (m, 1H), 2.2.-2.11 (m, 1H), 1.16-1.04 (m, 4H), 0.76-0.74 (d, J = 6.0 Hz, 3H). |

TABLE 4-continued

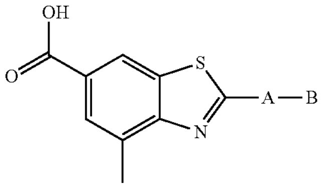

| Compound | A* | B | Scheme | LC-MS (M + H)$^+$ | $^1$HNMR (ppm) |
|---|---|---|---|---|---|
| IV-08 | 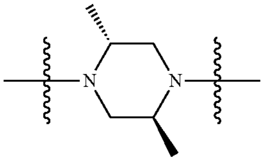 [SMILES: *N1C[C@H](C)N(*)C[C@H]1C] | 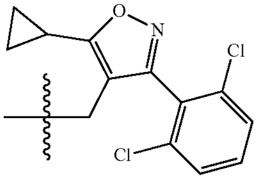 [SMILES: *Cc1c(-c2c(Cl)cccc2Cl)noc1C1CC1] | 6 | 570.8 | DMSO-$d_6$: δ 12.57 (s, 1H), 8.13 (s, 1H), 7.67-7.63 (m, 3H), 7.56-7.50 (m, 1H), 4.18 (s, 1H), 3.62-3.51 (m, 2H), 3.39-3.37 (m, 1H), 3.27-3.22 (m, 1H), 2.96-2.93 (m, 1H), 2.82-2.72 (m, 1H), 2.43 (s, 3H), 2.40-2.33 (m, 1H), 2.27-2.21 (m, 1H), 1.17-1.06 (m, 4H), 0.97-0.94 (d, J = 6.6 Hz, 3H), 0.86-0.84 (d, J = 6.5 Hz, 3H). |
| IV-09 | 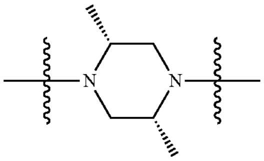 [SMILES: *N1C[C@@H](C)N(*)C[C@H]1C] | 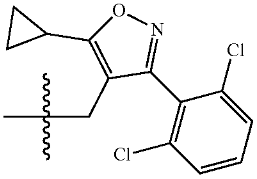 [SMILES: *Cc1c(-c2c(Cl)cccc2Cl)noc1C1CC1] | 6 | 571.1 | DMSO-$d_6$: δ 8.15 (s, 1H), 7.68-7.56 (m, 4H), 4.17 (s, 1H), 3.89-3.84 (m, 1H), 3.74-3.67 (m, 1H), 2.88-2.68 (m, 3H), 2.44 (s, 3H), 2.40-2.18 (m, 3H), 1.12-1.10 (m, 7H), 0.90-0.88 (d, J= 5.9 Hz, 3H). |
| IV-10 | 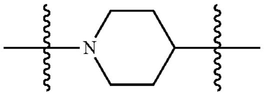 | 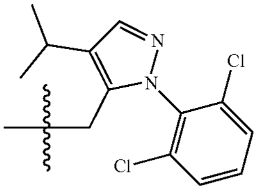 [SMILES: *Cc1c(C(C)C)cnn1-c1c(Cl)cccc1Cl] | 7 | 544.1 | DMSO-$d_6$: δ 8.15 (s, 1H), 7.69-7.67 (m, 3H), 7.61-7.57 (m, 1H), 4.03-4.00 (m, 2H), 3.33-3.25 (m, 1H), 3.01-2.96 (m, 2H), 2.44 (s, 3H), 2.33-2.25 (m, 2H), 1.62-1.59 (m, 2H), 1.36-1.32 (m, 1H), 1.32-1.30 (d, J = 6.8 Hz, 6H), 1.23-1.16 (m, 2H). |

*It is to be understood that ring A attaches to the thiazole ring at the open valence on the left-hand side of ring A and to the B-ring at the open valence on the right-hand side of ring A.

TABLE 5

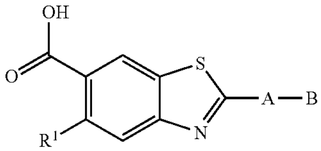

| Compound | $R^1$ | A* | B | Scheme | LC-MS (M + H)$^+$ | $^1$HNMR (ppm) |
|---|---|---|---|---|---|---|
| V-01 | Me | 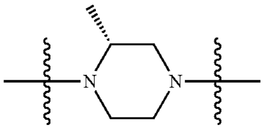 [SMILES: *N1CCN(*)[C@H](C)C1] | 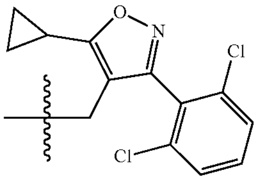 [SMILES: *Cc1c(-c2c(Cl)cccc2Cl)noc1C1CC1] | 6 | 557.2 | DMSO-$d_6$: δ 8.20 (s, 1H), 7.79-7.76 (m, 2H), 7.64-7.62 (m, 1 H), 7.25-7.22 (m, 1 H), 4.16 (s, 1H), 3.76-3.71 (m, 1H), 3.28-3.20 (m, 4H), 2.81-2.77 (m, 1H), 2.54-2.50 (m, 4H), 2.37-2.36 (m, 1H), 1.95-1.92 (m, 1H), 1.13-1.06 (m, 4H), 0.96-0.94 (m, 3H). |

TABLE 5-continued

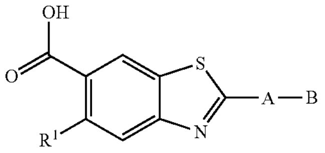

| Compound | $R^1$ | A* | B | Scheme | LC-MS $(M + H)^+$ | $^1$HNMR (ppm) |
|---|---|---|---|---|---|---|
| V-02 | F | 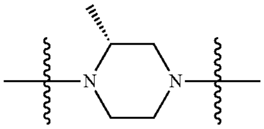 | 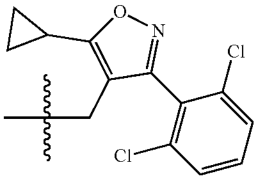 [SMILES: *Cc1c(-c2c(Cl)cccc2Cl)noc1C1CC1] | 6 | 561.2 | DMSO-$d_6$: δ 13.10 (s, 1H), 8.24 (m, 1H), 7.64 (m, 2H), 7.53-7.50 (m, 1H), 7.23-7.19 (m, 1H), 4.15 (s, 1H), 3.75 (m, 1H), 3.19-3.15 (m, 3H), 2.80-2.77 (m, 1H), 2.50-2.49 (m, 1H), 2.34-2.32 (m, 1H), 2.24-2.21 (m, 1H), 1.95-1.92 (m, 1H), 1.16-1.11 (m, 4H), 0.96-0.93 (m, 3H). |

*It is to be understood that ring A attaches to the thiazole ring at the open valence on the left-hand side of ring A and to the B-ring at the open valence on the right-hand side of ring A.

TABLE 6

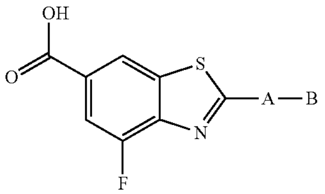

| Compound | A* | B | Scheme | LC-MS $(M + H)^+$ | $^1$HNMR (ppm) |
|---|---|---|---|---|---|
| VI-01 | 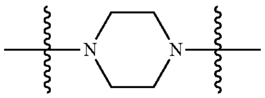 | 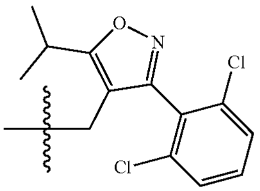 [SMILES: *Cc1c(-c2c(Cl)cccc2Cl)noc1C(C)C] | 4 | 549.1 | $CDCl_3$: δ 8.09 (s, 1H), δ 7.73 (d, J = 10.2 Hz, 1H), 7.41-7.39 (m, 2H), 7.34-7.26 (m, 1H), 3.50-3.47 (m, 4H), 3.33-3.23 (m, 3H), 2.39-2.43 (m, 4H), 1.42-1.38 (m, 6H). |
| VI-02 | 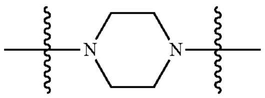 | 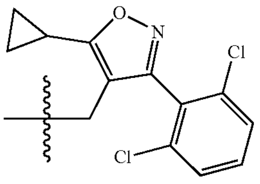 [SMILES: *Cc1c(-c2c(Cl)cccc2Cl)noc1C1CC1] | 4 | 546.7 | DMSO-$d_6$: δ 12.94 (brs, 1H), 8.23-8.22 (m, 1H), 7.65-7.52 (m, 4H), 3.45-3.43 (m, 4H), 3.32-3.30 (m, 2H), 2.39-2.34 (m, 5H), 1.15-1.09 (m, 4H). |
| VI-03 | 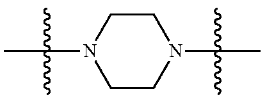 | 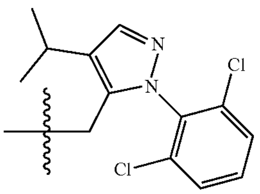 [SMILES: *Cc1c(C(C)C)cnn1-c1c(Cl)cccc1Cl] | 4 | 548.0 | DMSO-$d_6$: δ 8.18 (s, 1H), 7.69-7.67 (m, 3H), 7.59-7.54 (m, 2H), 3.41 (s, 6H), 3.01-2.94 (m, 1H), 2.34 (s, 4H), 1.25 (d, J = 6.8 Hz, 6H). |

TABLE 6-continued

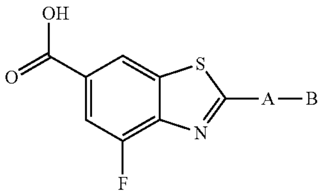

| Compound | A* | B | Scheme | LC-MS (M + H)$^+$ | $^1$HNMR (ppm) |
|---|---|---|---|---|---|
| VI-04 | 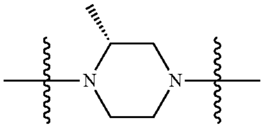 [SMILES: *N1CCN(*)[C@H](C)C1] | 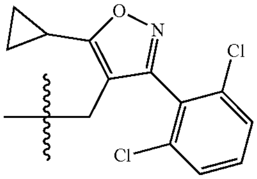 [SMILES: *Cc1c(-c2c(Cl)cccc2Cl)noc1C1CC1] | 6 | 561.0 | DMSO-$d_6$: δ 8.15 (s, 1H), 7.63 (d, J = 8 Hz, 2H), 7.57-7.52 (m, 2H), 4.16 (s, 1H), 3.77 (d, J = 10.8 Hz, 1H), 3.31-3.24 (m, 2H), 3.23-3.16 (m, 1H), 2.82 (d, J = 11.6 Hz, 1H), 2.67-2.56 (m, 1H), 2.39-2.32 (m, 1H), 2.26-2.22 (m, 1H), 1.96-1.90 (m, 1H), 1.17-1.11 (m, 4H), 1.10-0.95 (m, 3H). |
| VI-05 | 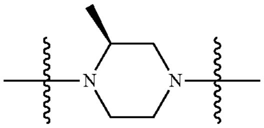 [SMILES: *N1CCN(*)[C@@H](C)C1] | 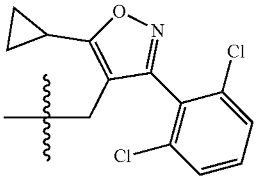 [SMILES: *Cc1c(-c2c(Cl)cccc2Cl)noc1C1CC1] | 6 | 561.3 | $CD_3OD$-$d_4$: δ 8.19 (s, 1H), 7.70-7.55 (m, 4H), 4.69-4.50 (m, 1H), 4.28-4.02 (m, 3H), 3.79-3.35 (m, 3H), 3.24-2.85 (m, 2H), 2.60-2.40 (m, 1H), 1.38-1.30 (m, 7H). |
| VI-06 | 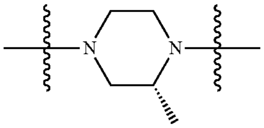 [SMILES: *N1CCN(*)[C@H](C)C1] | 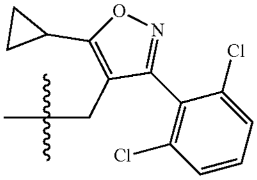 [SMILES: *Cc1c(-c2c(Cl)cccc2Cl)noc1C1CC1] | 6 | 561.1 | DMSO-$d_6$: δ 8.17 (d, J = 1.2 Hz, 1H), 7.65-7.54 (m, 4H), 3.72-3.60 (m, 3H), 3.26-3.20 (m, 1H), 3.09 (d, J = 13.6 Hz, 1H), 2.76-2.71 (m, 2H), 2.44-2.40 (m, 1H), 2.34-2.30 (m, 1H), 2.20-2.14 (m, 1H), 1.15-1.09 (m, 4H), 0.75 (d, J = 6.4 Hz, 3H). |
| VI-07 | 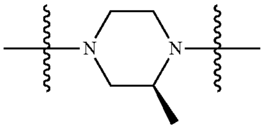 [SMILES: *N1CCN(*)[C@@H](C)C1] | 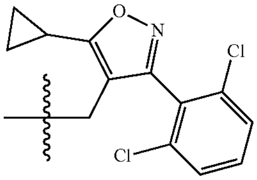 [SMILES: *Cc1c(-c2c(Cl)cccc2Cl)noc1C1CC1] | 6 | 561.1 | DMSO-$d_6$: δ 8.12 (s, 1H), 7.65-7.56 (m, 2H), 7.55-7.53 (m, 2H), 3.72-3.59 (m, 3H), 3.28-3.17 (m, 1H), 3.09 (d, J = 13.6 Hz, 1H), 2.75-2.70 (m, 2H), 2.42-2.41 (m, 1H), 2.33-2.29 (m, 1H), 2.19-2.10 (m, 1H), 1.14-1.07 (m, 4H), 0.76 (d, J = 6.0 Hz, 3H). |
| VI-08 | 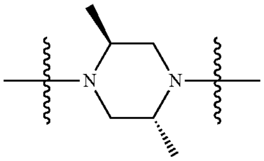 [SMILES: *N1C[C@H](C)N(*)C[C@H]1C] | 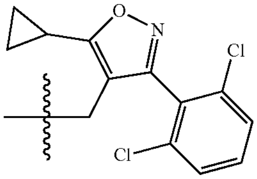 [SMILES: *Cc1c(-c2c(Cl)cccc2Cl)noc1C1CC1] | 6 | 575.3 | DMSO-$d_6$: δ 8.13 (s, 1H), 7.65 (d, 7 = 8 Hz, 2H), 7.56-7.52 (m, 2H), 4.16 (s, 1H), 3.60-3.53 (m, 2H), 3.39-3.35 (m, 1H), 3.32-3.23 (m, 1H), 2.96 (d, J = 2.8 Hz, 1H), 2.83-2.78 (m, 1H), 2.40-2.33 (m, 1H), 2.24 (d, J = 10.8 Hz, 1H), 1.15-1.08 (m, 4H), 0.96 (d, J = 6.8 Hz, 3H), 0.86 (d, J = 6.4 Hz, 3H). |
| VI-09 | 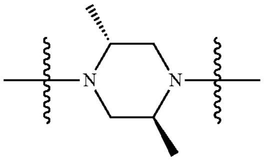 [SMILES: *N1C[C@H](C)N(*)C[C@H]1C] | 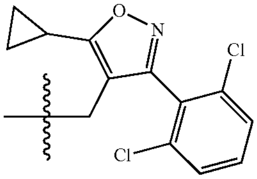 [SMILES: *Cc1c(-c2c(Cl)cccc2Cl)noc1C1CC1] | 6 | 575.1 | DMSO-$d_6$: δ 8.13 (s, 1H), 7.64 (d, J = 8.0 Hz, 2H), 7.57-7.52 (m, 2H), 4.17 (s, 1H), 3.61-3.53 (m, 2H), 3.39-3.35 (m, 1H), 3.32-3.23 (m, 1H), 2.96 (s, 1H), 2.83-2.79 (m, 1H), 2.40-2.33 (m, 1H), 2.24 (d, J = 11.6 Hz, 1H), 1.16-1.08 (m, 4H), 0.96 (d, J = 6.8 Hz, 3H), 0.86 (d, J = 6.4 Hz, 3H). |

TABLE 6-continued

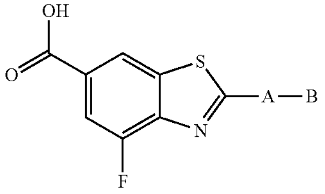

| Compound | A* | B | Scheme | LC-MS $(M + H)^+$ | $^1$HNMR (ppm) |
|---|---|---|---|---|---|
| VI-10 | 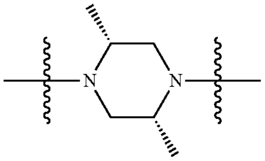 [SMILES: *N1C[C@@H](C)N(*)C[C@H]1C] | 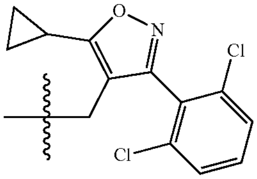 [SMILES: *Cc1c(-c2c(Cl)cccc2Cl)noc1C1CC1] | 6 | 575.3 | $CD_3OD-d_4$: δ 8.21 (s, 1H), 7.70-7.60 (m, 1H), 7.57-7.53 (m, 3H), 4.69-4.34 (m, 2H), 4.20-3.91 (m, 2H), 3.64-3.31 (m, 2H), 3.22-2.81 (m, 2H), 2.51-2.44 (m, 1H), 1.59-1.44 (m, 3H), 1.33-1.12 (m, 7H). |
| VI-11 | 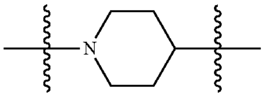 | 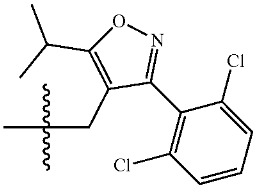 [SMILES: *Cc1c(-c2c(Cl)cccc2Cl)noc1C(C)C] | 7 | 548.1 | DMSO-$d_6$: δ 8.15 (s, 1H), 7.67 (d, J = 7.6 Hz, 2H), 7.62-7.57 (m, 2H), 4.02 (d, J = 12.4 Hz, 2H), 3.05-2.95 (m, 2H), 2.33-2.25 (m, 2H), 1.63 (d, J = 1.6 Hz, 2H), 1.38-1.31 (m, 7H), 1.24-1.20 (m, 3H). |

*It is to be understood that ring A attaches to the thiazole ring at the open valence on the left-hand side of ring A and to the B-ring at the open valence on the right-hand side of ring A.

TABLE 7

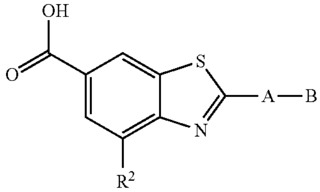

| Compound | $R^2$ | A* | B | Scheme | LC-MS $(M + H)^+$ | $^1$HNMR (ppm) |
|---|---|---|---|---|---|---|
| VII-02 | Cl | 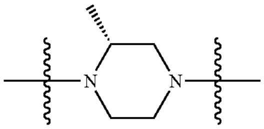 | 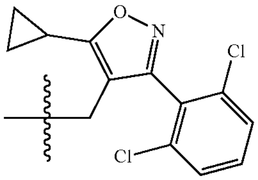 [SMILES: *Cc1c(-c2c(Cl)cccc2Cl)noc1C1CC1] | 6 | 579.1 | DMSO-$d_6$: δ 8.23 (s, 1H), 7.81 (s, 1H), 7.65-7.62 (m, 2H), 7.56-7.51 (m, 1H), 4.16 (s, 1H), 4.36-4.34 (m, 1H), 3.84-3.79 (m, 1H), 3.20-3.16 (m, 2H), 2.82-2.56 (m, 3H), 2.37-2.23 (m, 1H), 1.93-1.90 (m, 1H), 1.15-1.12 (m, 4H), 0.98-0.95 (d, J = 6.6 Hz, 3H). |
| VII-03 | CF3 | 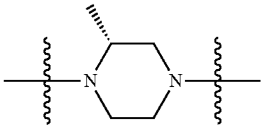 | 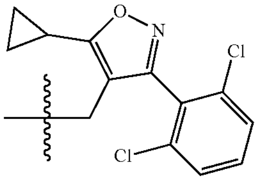 [SMILES: *Cc1c(-c2c(Cl)cccc2Cl)noc1C1CC1] | 9 | 611.0 | DMSO-$d_6$: δ 8.46 (s, 1H), 8.32 (s, 1H), 7.45-7.36 (m, 2H), 7.34-7.31 (m, 1H), 4.41-3.88 (brs, 2H), 3.48-3.21 (m, 3H), 2.96-2.90 (m, 1H), 2.69-2.61 (m, 1H), 2.38-2.31 (m, 1H), 2.19-2.11 (m, 1H), 2.06-1.97 (m, 1H), 1.32-1.26 (m, 2H), 1.18-1.01 (m, 5H). |

TABLE 7-continued

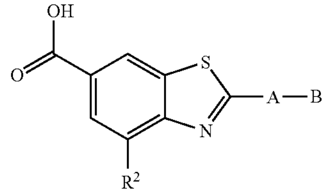

| Compound | $R^2$ | A* | B | Scheme | LC-MS $(M + H)^+$ | $^1$HNMR (ppm) |
|---|---|---|---|---|---|---|
| VII-05 | Cl | 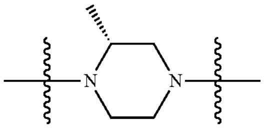 | 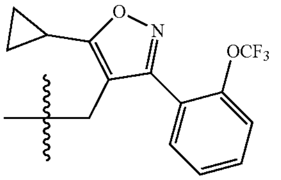 [SMILES: *Cc1c(-c2ccccc2OC(F)(F)F)noc1C1CC1] | 4 | 593.1 | DMSO-$d_6$: δ 12.98 (s, 1H), 8.32 (s, 1H), 7.82-7.51 (m, 5H), 4.18 (s, 1H), 3.83 (s, 1H), 3.49-3.36 (m, 2H), 3.17-3.12 (m, 1H), 2.79 (d, J = 10.4 Hz, 1H), 2.64 (d, J = 11.2 Hz, 1H), 2.40-2.31 (m, 1H), 2.23-2.16 (m, 1H), 2.01-1.96 (m, 1H), 1.22-0.85 (m, 7H). |

*It is to be understood that ring A attaches to the thiazole ring at the open valence on the left-hand side of ring A and to the B-ring at the open valence on the right-hand side of ring A.

Scheme 12 (Compound VIII-04)

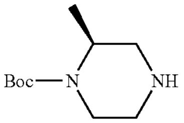

+

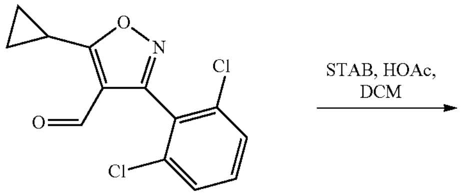

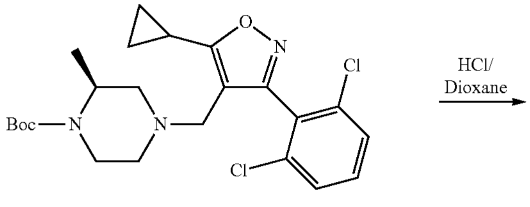

12a

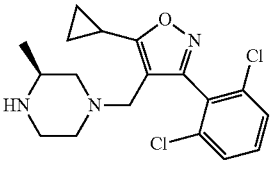

12b

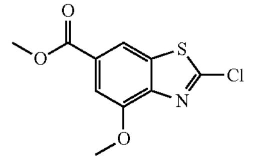

INT-001

$K_2CO_3$, DMSO

-continued

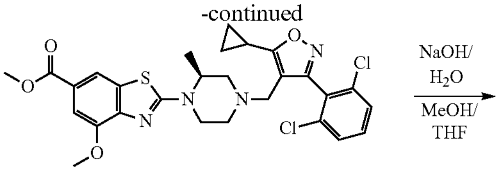

12c

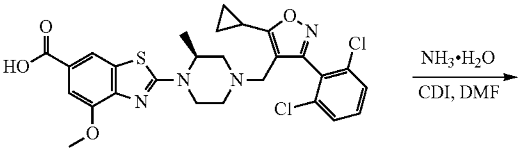

12d

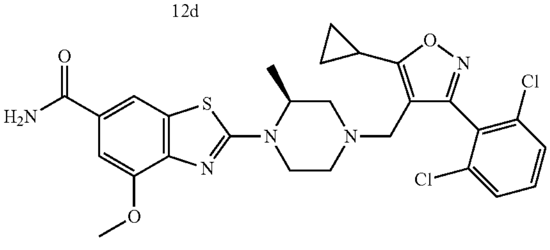

VIII-04

Experimental Details for Compound VIII-04 (Scheme 12)

tert-Butyl (2S)-4-[[5-cyclopropyl-3-(2,6-dichlorophenyl)-1,2-oxazol-4-yl]methyl]-2-methylpiperazine-1-carboxylate (Compound 12a)

To a solution of tert-butyl (2S)-2-methylpiperazine-1-carboxylate (400 mg, 2.00 mmol) in dichloromethane (6 mL) was added acetic acid (120 mg, 2.0 mmol) and 5-cyclopropyl-3-(2,6-dichlorophenyl)-1,2-oxazole-4-carbaldehyde (562 mg, 1.99 mmol). After the mixture was stirred for 30 min, $NaBH(OAc)_3$ (1.3 g, 6.13 mmol) was added. The resulting solution was stirred overnight at room temperature. The solids were filtered out. The resulting mixture was concentrated under vacuum. The residue was applied onto a silica gel column with ethyl acetate/petroleum ether (30:70). This resulted in 670 mg (72%) of the title compound as a white solid. LC-MS (ESI, m/z): $[M+H]^+$=466.2.

(S)-5-Cyclopropyl-3-(2,6-dichlorophenyl)-4-((3-methylpiperazin-1-yl)methyl) isoxazole (Compound 12b)

To a solution of Compound 12a (620 mg, 1.3 mmol) in dioxane (4 mL) was added a solution of HCl in dioxane (8 mL, 4M). The resulting solution was stirred for 2 h at room temperature. The resulting mixture was concentrated under vacuum. This resulted in 48 mg (98%) of the title compound as a white solid. LC-MS (ESI, m/z): $[M+H]^+$=366.2.

(S)-Methyl 2-(4-((5-cyclopropyl-3-(2,6-dichlorophenyl) isoxazol-4-yl)methyl)-2-methylpiperazin-1-yl)-7-methoxybenzo[d]thiazole-5-carboxylate (Compound 12c)

To a solution of Compound 12b (100 mg, 0.27 mmol) in DMSO was added potassium carbonate (162 mg, 1.16 mmol) and methyl 2-chloro-7-methoxy-1,3-benzothiazole-5-carboxylate (143 mg, 0.55 mmol). The resulting solution was stirred for 2 h at 120° C. The reaction was then quenched by the addition of 5 mL of water. The resulting solution was diluted with 50 mL of ethyl acetate. The resulted mixture was washed with water and brine. The residue was concentrated under vacuum after dried over anhydrous sodium sulfate. The residue was applied onto a silica gel column with ethyl acetate/petroleum ether (24:76). This resulted in 120 mg (75%) of the title compound as a light yellow solid. LC-MS (ESI, m/z): $[M+H]^+$=587.2.

(S)-2-(4-((5-Cyclopropyl-3-(2,6-dichlorophenyl) isoxazol-4-yl)methyl)-2-methylpiperazin-1-yl)-7-methoxybenzo[d]thiazole-5-carboxylic acid (Compound 12d)

To a solution of Compound 12c (100 mg, 0.17 mmol) in a mixed solvent of tetrahydrofuran/methanol/$H_2O$ (5 mL, 1:1:1) was added sodium hydroxide (30 mg, 0.75 mmol). The resulting solution was stirred for 3 h at 50° C. The pH value of the solution was adjusted to 6 with hydrogen chloride (2 N). The resulting solution was extracted with dichloromethane 3 times and the organic layers were combined. The organic phase was washed successively with water and brine. The residue was concentrated under vacuum after dried over anhydrous sodium sulfate. The residue was applied onto a silica gel column with dichloromethane/methanol (15:1). This resulted in 60 mg (61%) of the title compound as a white solid. LC-MS (ESI, m/z): $[M+H]^+$=573.2.

(S)-2-(4-((5-Cyclopropyl-3-(2,6-dichlorophenyl) isoxazol-4-yl)methyl)-2-methylpiperazin-1-yl)-7-methoxybenzo[d]thiazole-5-carboxamide (Compound VIII-04)

To a solution of Compound 12d (60 mg, 0.1 mmol) in DMF (2 mL) was added CDI (18 mg, 0.11 mmol) at room temperature. $NH_3.H_2O$ (0.1 ml, 25%, w %) was added into the mixture solution after stirred for 1 h. The resulting solution was stirred for another 2 h at room temperature. The resulting mixture was concentrated under vacuum. The residue was applied onto a reverse column with $H_2O$/$CH_3CN$ (60:40). This resulted in 6.4 mg (13%) of the title compound as a white solid. LC-MS (ESI, m/z): $[M+H]^+$=572.1. $^1$HNMR (300 MHz, DMSO-$d_6$, ppm): δ 7.91 (s, 1H), 7.70-7.58 (s, 3H), 7.40 (s, 1H), 4.44 (s, 1H), 4.02-3.97 (m, 3H), 3.88 (s, 3H), 3.25 (s, 1H), 3.11 (s, 1H), 2.98-2.81 (m, 2H), 2.72-2.66 (m, 2H), 1.30-1.15 (m, 7H).

Scheme 13 (Compound VIII-03)

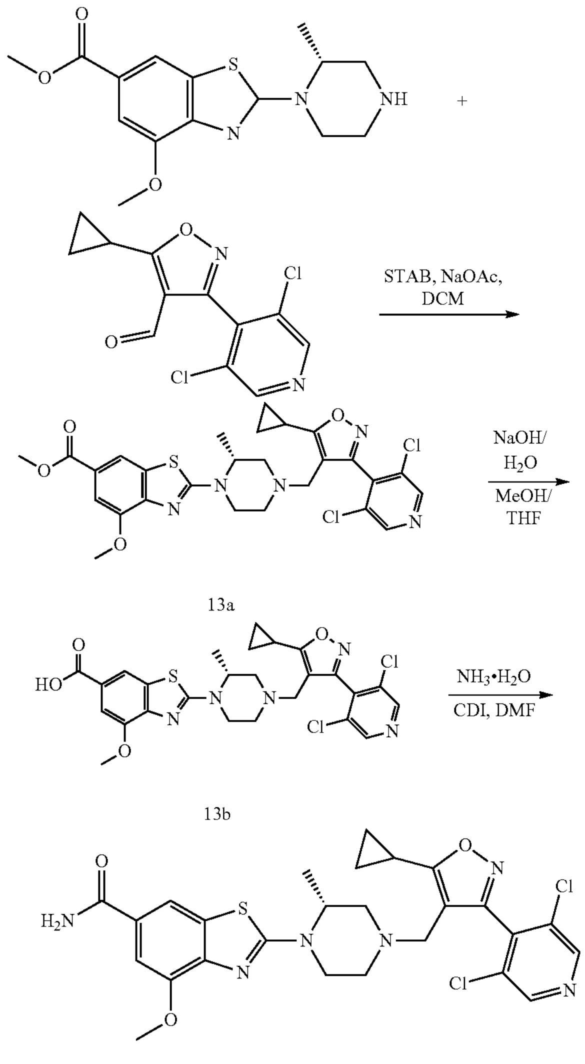

13a

13b

VIII-03

Experimental Details for Compound VIII-03 (Scheme 13)

Methyl 2-[(2R)-4-[[5-cyclopropyl-3-(3,5-dichloropyridin-4-yl)-1,2-oxazol-4-yl]methyl]-2-methylpiperazin-1-yl]-4-methoxy-1,3-benzothiazole-6-carboxylate (Compound 13a)

To a solution of methyl 4-methoxy-2-[(2R)-2-methylpiperazin-1-yl]-1,3-benzothiazole-6-carboxylate (110 mg, 0.34 mmol) and 5-cyclopropyl-3-(3,5-dichloropyridin-4-yl)-1,2- oxazole-4-carbaldehyde (116 mg, 0.41 mmol) in dichloromethane (6 mL) was added NaOAc (93 mg, 0.68 mmol). The mixture was stirred for 1 h at room temperature then $NaBH(OAc)_3$ (291 mg, 1.37 mmol) was added. The resulting mixture was stirred overnight at room temperature. The mixture was concentrated under vacuum. The residue was applied onto a silica gel column with ethyl acetate/petroleum ether (1:4). This resulted in 150 mg (74%) of the title compound as a white solid. LC-MS (ESI, m/z): [M+H]+=588.1.

2-[(2R)-4-[[5-Cyclopropyl-3-(3,5-dichloropyridin-4-yl)-1,2-oxazol-4-yl]methyl]-2-methylpiperazin-1-yl]-4-methoxy-1,3-benzothiazole-6-carboxylic acid (Compound 13b)

To a solution of Compound 13a (150 mg, 0.25 mmol) in a mixed solvent of methanol (2 mL) and tetrahydrofuran (2 mL) was added a solution of sodium hydroxide (51 mg, 1.28 mmol) in water (2 mL). The resulting solution was stirred for 2 h at 50° C. The pH value of the mixture was adjusted to 5 with hydrogen chloride (2 N). The mixture was concentrated under vacuum. The residue was applied onto a silica gel column with dichloromethane/methanol (15:1). This resulted in 90 mg (61%) of the title compound as a white solid. LC-MS (ESI, m/z): $[M+H]^+$=574.1.

2-[(2R)-4-[[5-Cyclopropyl-3-(3,5-dichloropyridin-4-yl)-1,2-oxazol-4-yl]methyl]-2-methylpiperazin-1-yl]-4-methoxy-1,3-benzothiazole-6-carboxamide (Compound VIII-03)

To a solution of Compound 13b (90 mg, 0.16 mmol) in DMF (3 mL) was added CDI (25 mg, 0.15 mmol). Ammonia water (0.2 mL) was added one portion after the mixture was stirred for 30 min. The resulting mixture was stirred for 2 h at room temperature. The reaction solution was concentrated under vacuum. The residue was applied onto a C18 column with ACN/$H_2O$ (1:1). This resulted in 48.8 mg (54%) of the title compound as a white solid. LC-MS (ESI, m/z): $[M+H]^+$=573.2. $^1$HNMR (400 MHz, $CD_3OD$-$d_4$, ppm): δ 8.70 (d, J=0.8 Hz, 2H), 7.83 (d, J=1.6 Hz, 1H), 7.43 (d, J=1.6 Hz, 1H), 4.20-4.17 (m, 1H), 3.99 (s, 3H), 3.85 (d, J=12.4 Hz, 1H), 3.43-3.20 (m, 3H), 2.86 (d, J=11.2 Hz, 1H), 2.61 (d, J=11.2 Hz, 1H), 2.36-2.25 (m, 2H), 2.05-2.01 (m, 1H), 1.19-1.05 (m, 4H), 0.94-0.92 (d, J=6.5 Hz, 3H).

Following the procedure described above for Scheme 12 and substituting the appropriate reagents, starting materials and purification methods known to those skilled in the art, the following compounds of the present invention were prepared.

TABLE 8

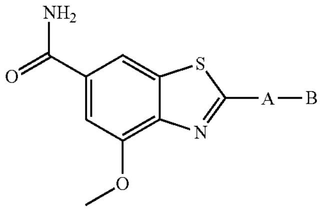

| Compound | A* | B | LC-MS $(M + H)^+$ | $^1$HNMR (ppm) |
|---|---|---|---|---|
| VIII-01 | 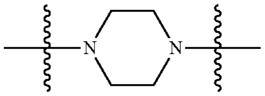 | 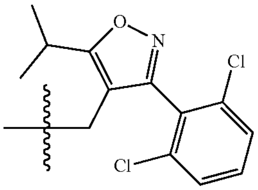 [SMILES: *Cc1c(-c2c(Cl)cccc2Cl)noc1C(C)C] | 560.3 | $CDCl_3$: δ 7.67 (d, J = 1.5 Hz, 1H), 7.43-7.41 (m, 2H), 7.36-7.31 (m, 2H), 4.03 (s, 3H), 3.50 (brs, 4H), 3.30 (brs, 2H), 2.43 (brs, 4H), 1.44 (d, J = 6.9 Hz, 6H). |
| VIII-02 | 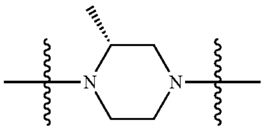 [SMILES: *N1CCN(*)[C@H](C)C1] | 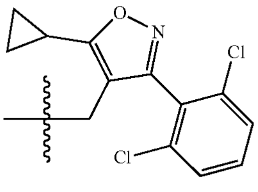 [SMILES: *Cc1c(-c2c(Cl)cccc2Cl)noc1C1CC1] | 572.1 | DMSO-$d_6$: δ 7.88 (s, 2H), 7.65-7.62 (m, 2H), 7.58-7.51 (m, 1H), 7.38 (s, 1H), 7.27 (s, 1H), 4.13 (s, 1H), 3.87 (s, 3H), 3.75-3.71 (m, 1H), 3.28 (s, 1H), 3.23-3.11 (m, 2H), 2.81-2.72 (m, 1H), 2.58-2.57 (m, 1H), 2.39-2.20 (m, 1H), 1.95-1.86 (m, 1H), 1.17-1.07 (m, 4H), 0.94-0.92 (d, J = 6.5 Hz, 3H. |
| VIII-05 | 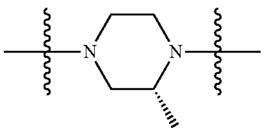 [SMILES: *N1CCN(*)[C@H](C)C1] | 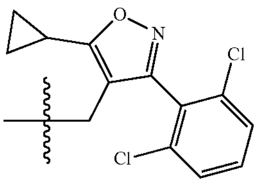 [SMILES: *Cc1c(-c2c(Cl)cccc2Cl)noc1C1CC1] | 572.3 | DMSO-$d_6$: δ 7.89 (s, 2H), 7.64-7.51 (m, 3H), 7.38 (s, 1H), 7.26 (s, 1H), 3.87 (s, 3H), 3.72-3.54 (m, 3H), 3.18-3.03 (m, 2H), 2.73-2.69 (m, 2H), 2.41-2.26 (m, 2H), 2.17-2.07 (m, 1H), 1.16-1.04 (m, 4H), 0.75-0.73 (d, J = 6 Hz, 3H). |

TABLE 8-continued

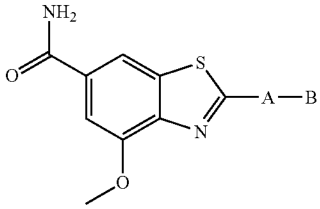

| Compound | A* | B | LC-MS (M + H)$^+$ | $^1$HNMR (ppm) |
|---|---|---|---|---|
| VIII-06 | 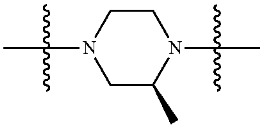 [SMILES: *N1CCN(*)[C@@H](C)C1] | 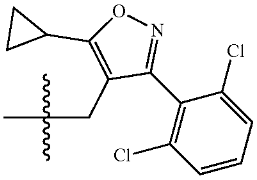 [SMILES: *Cc1c(-c2c(Cl)cccc2Cl)noc1C1CC1] | 572.2 | DMSO-d$_6$: δ 7.88 (s, 2H), 7.64-7.61 (m, 2H), 7.57-7.51(m, 1H), 7.38 (s, 1H), 7.26 (s, 1H), 3.87 (s, 3H), 3.72-3.54 (s, 3H), 3.18-3.15 (m, 1H), 3.11-3.03 (m, 1H), 2.74-2.63 (m, 2H), 2.41-2.36 (m, 1H), 2.33-2.31 (m, 1H), 2.18-2.10 (m, 1H), 1.17-1.04 (m, 4H), 0.76-0.74 (d, J = 6 Hz, 3H). |
| VIII-07 | 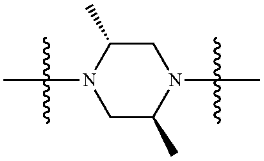 | 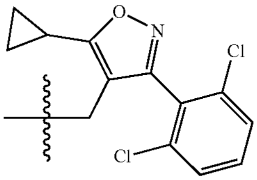 [SMILES: *Cc1c(-c2c(Cl)cccc2Cl)noc1C1CC1] | 586.2 | DMSO-d$_6$: δ 7.86 (s, 2H), 7.65-7.63 (m, 2H), 7.56-7.51 (m, 1H), 7.37 (s, 1H), 7.25 (s, 1H), 4.15-4.13 (s, 1H), 3.87 (s, 3H), 3.57-3.52 (m, 2H), 3.27-3.22 (m, 1H), 2.97-2.93 (m, 1H), 2.84-2.72 (m, 1H), 2.42-2.33 (m, 1H), 2.27-2.19 (m, 1H), 1.15-1.06 (m, 4H), 0.93 (d, J = 6.9 Hz, 3H), 0.86 (d, J = 6.3 Hz, 3H). |

*The A-ring is to be understood as attaching to the thiazole ring at the open valence on the left-hand side and to the B-ring at the open valence on the right-hand side.

Scheme 14 (Compound IX-01 and IX-02)

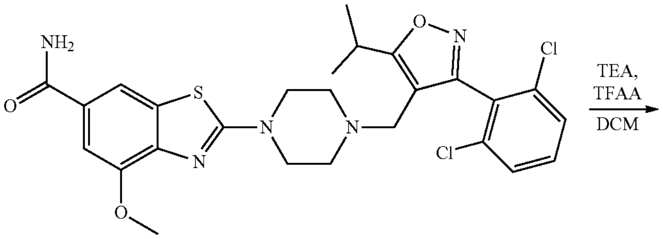

VIII-01

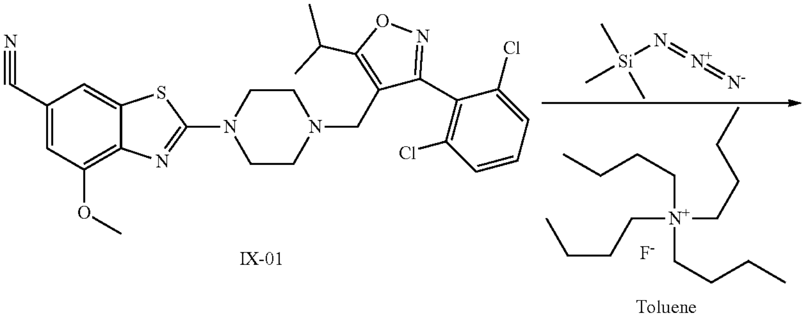

IX-01

-continued

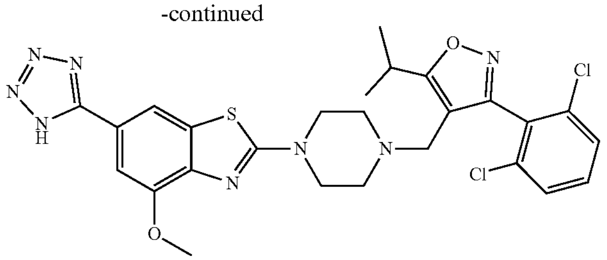

IX-02

Experimental Details for Compound IX-01 and IX-02 (Scheme 14)

2-(4-((3-(2,6-Dichlorophenyl)-5-isopropylisoxazol-4-yl)methyl)piperazin-1-yl)-4-methoxybenzo[d]thiazole-6-carbonitrile (Compound IX-01)

To a solution of Compound VIII-01 (700 mg, 1.25 mmol) in dichloromethane (5 mL) was added TEA (252 mg, 2.50 mmol). After cooling to 0° C., TFAA (529 mg, 5.45 mmol) in DCM (2 mL) was added in dropwise. The resulting solution was stirred for 15 min at 0° C. The resulting mixture was concentrated under vacuum. The residue was applied onto a silica gel column with dichloromethane/methanol (94:6). This resulted in 500 mg (74%) of the title compound as a white solid. LC-MS (ESI, m/z): $[M+H]^+$=542.3. $^1$H-NMR (300 MHz, DMSO-$d_6$, ppm): δ 7.92 (s, 1H), 7.64-7.62 (m, 2H), 7.57-7.52 (m, 1H), 7.27 (s, 1H), 3.88 (s, 3H), 3.39 (brs, 4H), 3.34-3.26 (m 3H), 2.34 (brs, 4H), 1.34 (d, J=6.9 Hz, 6H).

3-(2,6-Dichlorophenyl)-5-isopropyl-4-((4-(4-methoxy-6-(1H-tetrazol-5-yl)benzo[d]thiazol-2-yl)piperazin-1-yl)methyl)isoxazole (Compound IX-02)

To a solution of Compound IX-01 (100 mg, 0.18 mmol) in toluene (3 mL) was added azidotrimethylsilane (42.5 mg, 0.37 mmol) and tetrabutylammonium fluoride (94 mg, 0.36 mmol). The resulting solution was stirred for 18 h at 85° C. The reaction was quenched by the addition of 10 mL of water. The resulting mixture was extracted with 3*20 mL of ethyl acetate and the organic layers were combined. The resulted mixture was washed with water and brine. The residue was concentrated under vacuum after dried over anhydrous sodium sulfate. The crude product was purified by a reverse chromatography with $H_2O/CH_3CN$ (39:61). This resulted in 2.8 mg (3%) of the title compound as a white solid. LC-MS (ESI, m/z): $[M+H]^+$=585.2. $^1$H-NMR (300 MHz, DMSO-$d_6$, ppm): δ 8.01 (s, 1H), 7.64-7.63 (m, 2H), 7.57-7.52 (m, 2H), 3.95 (s, 3H), 3.45-3.37 (m, 5H), 3.27 (s, 2H), 2.35 (brs, 4H), 1.34 (d, J=6.9 Hz, 6H).

Scheme 15 (Compound X-01)

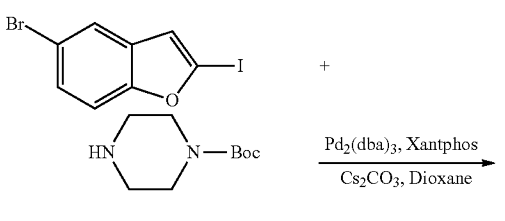

-continued

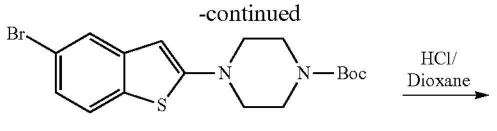

15a

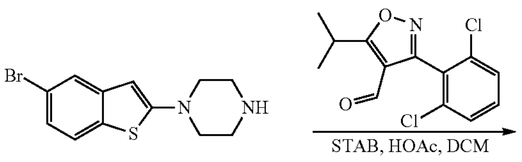

15b

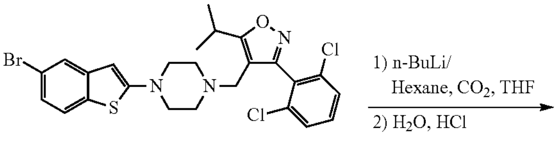

15c

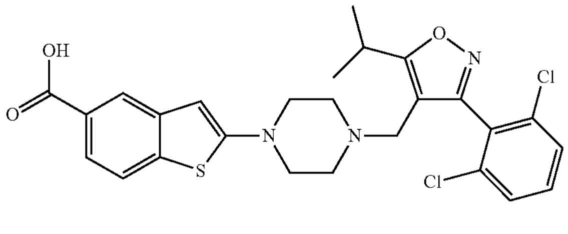

X-01

Experimental Details for Compound X-01 (Scheme 15)

tert-Butyl 4-(5-bromo-1-benzothiophen-2-yl)piperazine-1-carboxylate (Compound 15a)

To a solution of 5-bromo-2-iodo-1-benzothiophene (500 mg, 1.47 mmol) and tert-butyl piperazine-1-carboxylate (412 mg, 2.21 mmol) in dioxane (5 mL) was added $Pd_2(dba)_3.CHCl_3$ (77 mg, 0.074 mmol), Xantphos (85 mg, 0.15 mmol) and $Cs_2CO_3$ (1.2 g, 3.68 mmol). The resulting solution was stirred overnight at 60° C. The solids were filtered out. The resulting mixture was concentrated under vacuum. The residue was applied onto a silica gel column with ethyl acetate/petroleum ether (1:10). This resulted in 200 mg (34%) of the title compound as a yellow solid. LCMS (ESI, m/z): $[M+H]^+$=397.1.

1-(5-Bromo-1-benzothiophen-2-yl)piperazine (Compound 15b)

To a solution of Compound 15a (200 mg, 0.50 mmol) in dioxane (3 mL) was added a solution of hydrogen chloride in dioxane (6 mL, 4 M). The resulting solution was stirred for 1 h at room temperature. The resulting mixture was concentrated under vacuum. This resulted in 120 mg (80%) of the title compound as a yellow solid. LCMS (ESI, m/z): $[M+H]^+$=296.9.

1-(5-Bromo-1-benzothiophen-2-yl)-4-[[3-(2,6-dichlorophenyl)-5-(propan-2-yl)-1,2-oxazol-4-yl]methyl]piperazine (Compound 15c)

To a solution of Compound 15b (150 mg, 0.50 mmol) and 3-(2,6-dichlorophenyl)-5-(propan-2-yl)-1,2-oxazole-4-carbaldehyde (143 mg, 0.50 mmol) in dichloromethane (10 mL) was added acetic acid (30 mg, 0.50 mmol). The reaction was stirred at r.t. for 30 min, then $NaBH(OAc)_3$ (318 mg, 1.5 mmol) was added into the mixture. The resulting solution was stirred overnight at room temperature. The resulting mixture was concentrated under vacuum. The residue was applied onto a silica gel column with ethyl acetate/petroleum ether (1:10). This resulted in 180 mg (63%) of the title compound as a white solid. LCMS (ESI, m/z): $[M+H]^+$=566.2.

2-(4-[[3-(2,6-Dichlorophenyl)-5-(propan-2-yl)-1,2-oxazol-4-yl]methyl]piperazin-1-yl)-1-benzofuran-5-carboxylic acid (Compound X-01)

To a solution of Compound 15c (80 mg, 0.14 mmol) in tetrahydrofuran (1 mL) was added a solution of n-BuLi in hexane (0.056 mL, 0.14 mmol) at −78° C. The resulting solution was stirred for 30 min at this temperature. $CO_2$ gas was bubbled into the mixture at −78° C. until saturated. The mixture was allowed warm to room temperature and stirred for another 1 h. The reaction was then quenched by the addition of 1 mL of water. The pH value of the mixture was adjusted to 3 with HCl (2 N). The resulting solution was extracted with 3×5 mL of dichloromethane and the organic layers were combined. The resulted mixture was washed with water and brine. The residue was concentrated under vacuum after dried over anhydrous sodium sulfate. The residue was applied onto a silica gel column with dichloromethane/methanol (20:1). This resulted in 40 mg (53%) of the title compound as a white solid. LCMS (ESI, m/z): $[M+H]^+$=530.3. $^1H$ NMR (300 MHz, DMSO-$d_6$, ppm): δ 12.67 (s, 1H), 8.05 (s, 1H), 7.80-7.74 (s, 1H), 7.66-7.50 (s, 4H), 6.37 (s, 1H), 3.45-3.35 (s, 1H), 3.28 (s, 2H), 3.06-2.98 (m, 4H), 2.42-2.34 (m, 4H), 1.34 (d, J=6.9 Hz, 6H).

Biological Assays

The compounds of the present technology may be assayed using the following procedures and show or will be shown to have FXR binding activity.

FXR Transactivation Assay

Reagents:

HEK293T pGL4.35 [luc2P/9XGAL4 UAS/Hygro]

pBIND-FXR Vector

DMEM medium, high glucose

Fetal Bovine Serum (FBS, heat-inactivated)

Penicillin-Streptomycin (10000 U/ml, 100 ml)

DMEM, High Glucose, HEPES, no Phenol Red

Opti-MEM® I Reduced Serum Medium

Steady-Glo™ Luciferase Assay System

TransIT-293 Transfection Reagent

GW4064 as a positive control

Process:

1. Hek293T cells were plated at $1.1*10^6$/ml into a 100 mm dish.
2. Cells were transfected with 8.4 μg of pBind-FXR, 1.26 μg of the reporter vector pGL4.35 (Promega). Cells were incubated at 37° C. under 5% CO2 atmosphere.
3. All of compounds were 3-fold serial diluted from 10 mM stock for 10 doses in DMSO.
4. Transfer compound dilutions into 384 well assay plates using liquid workstation.
5. Seed 25 ul HEK293T cells into 384 well assay plate (prepared step 4) at $0.6*10^5$/ml. Cells were incubated at 37° C. under 5% CO2 atmosphere overnight.
6. Add 25 ul steady-Glo™ Luciferase Assay Reagent into each well of 384-well assay plate.
7. Record the luminescence value on Envision 2104 plate reader.
8. Calculate EC50 by fitting % Activity values and log of compound concentrations to nonlinear regression (dose response–variable slope) with Graphpad 5.0.

FXR Coactivator Assay

Reagents:

LanthaScreen™ TR-FRET Farnesoid X Receptor Coactivator Assay GW4064 as a positive control Process:

1. All of compounds were 3-fold serial diluted from 10 mM stock for 10 doses in DMSO.
2. Dilute each 100× agonist serial dilution to 2× using Complete Coregulator buffer G.
3. Transfer 10 μl of each of the 2× agonist serial dilutions to 384 well assay plates.
4. Add 5 μl of 4×FXR-LBD to 384 well assay plates.
5. Add 5 μl of 4× peptide/4× antibody solution to 384 well assay plates.
6. Incubate at room temperature protected from light.
7. Read the plate at wavelengths of 520 nm and 495 nm on Envision 2104 plate reader.
8. Calculate the TR-FRET ratio by dividing the emission signal at 520 nm by the emission signal at 495 nm.
9. Calculate EC50 by fitting % Activity values and log of compound concentrations to nonlinear regression (dose response–variable slope) with Graphpad 5.0.

Results of the above assays with the present compounds are shown in Table 9.

TABLE 9

FXR Coactivator and Transactivation Assays

| Compound | FXR Transactivation Assay ($EC_{50}$) | FXR Coactivator Assay ($EC_{50}$) |
|---|---|---|
| II-01 | B | A |
| II-02 | A | A |
| II-03 | B | A |
| II-04 | B | A |
| II-05 | A | A |
| II-06 | A | — |
| II-07 | C | — |
| II-08 | A | A |
| II-09 | A | A |
| II-10 | B | — |
| II-11 | B | A |
| II-12 | A | — |
| II-13 | A | A |
| II-14 | C | — |
| II-15 | A | — |
| II-16 | B | A |
| II-17 | C | — |
| II-18 | A | A |
| II-19 | B | A |
| II-20 | B | A |

TABLE 9-continued

FXR Coactivator and Transactivation Assays

| Compound | FXR Transactivation Assay ($EC_{50}$) | FXR Coactivator Assay ($EC_{50}$) |
|---|---|---|
| II-21 | B | — |
| II-22 | B | A |
| II-23 | C | — |
| II-24 | A | A |
| II-25 | B | — |
| II-26 | A | A |
| II-27 | A | — |
| II-28 | B | A |
| II-29 | C | — |
| II-30 | B | A |
| II-31 | C | — |
| II-32 | A | A |
| II-33 | B | A |
| II-34 | A | — |
| II-35 | C | — |
| II-36 | A | — |
| II-37 | B | — |
| II-38 | C | — |
| II-39 | B | — |
| II-40 | B | A |
| II-41 | C | — |
| II-42 | B | A |
| II-43 | B | A |
| II-44 | C | — |
| II-45 | A | — |
| II-46 | — | A |
| II-47 | — | B |
| II-48 | — | B |
| II-49 | C | — |
| II-50 | A | — |
| II-51 | — | A |
| III-01 | B | — |
| III-02 | C | — |
| III-03 | A | — |
| III-04 | C | — |
| III-05 | C | — |
| III-06 | C | — |
| III-07 | A | — |
| III-08 | C | — |
| III-09 | C | B |
| III2-01 | — | A |
| III3-01 | — | C |
| IV-01 | A | A |
| IV-02 | A | — |
| IV-03 | B | — |
| IV-04 | A | — |
| IV-05 | C | — |
| IV-06 | B | — |
| IV-07 | C | — |
| IV-08 | A | — |
| IV-09 | C | — |
| IV-10 | B | — |
| V-01 | B | — |
| V-02 | A | — |
| VI-01 | B | A |
| VI-02 | A | — |
| VI-03 | B | — |
| VI-04 | A | A |
| VI-05 | C | — |
| VI-06 | B | — |
| VI-07 | B | — |
| VI-08 | C | — |
| VI-09 | A | — |
| VI-10 | C | — |
| VI-11 | C | — |
| VII-01 | A | A |
| VII-02 | A | — |
| VII-03 | A | — |
| VII-04 | A | — |
| VII-05 | — | A |
| VIII-01 | B | A |
| VIII-02 | A | A |
| VIII-03 | B | — |
| VIII-04 | C | — |
| VIII-05 | A | — |
| VIII-06 | C | — |
| VIII-07 | B | — |
| IX-01 | C | — |
| IX-02 | C | — |
| X-01 | C | — |

A: $EC_{50}$ = 10 nM to 100 nM;
B: $EC_{50}$ = 101 nM-400 nM
C: $EC_{50}$ = 401 nM-5 uM

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound according to formula I (I)

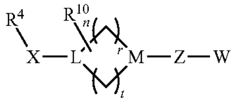

a stereoisomer thereof, a salt thereof, or a salt of the stereoisomer; wherein

L and M are both N;

Z is a substituted or unsubstituted $C_1$-$C_4$ alkylene;

W is

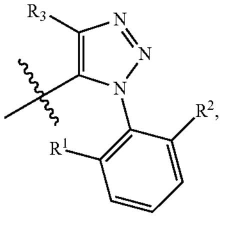
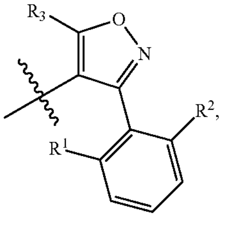

-continued

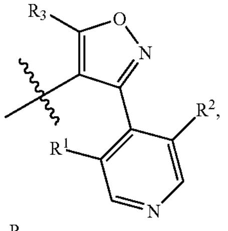
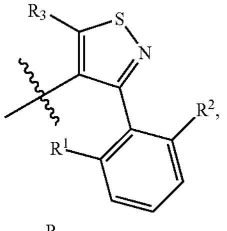
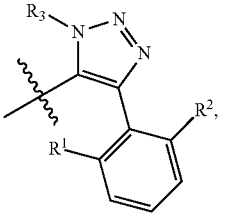
or
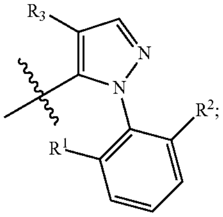

X is

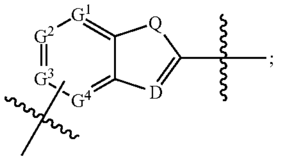

D is N or $CR^9$;

one of $G^1$, $G^2$, $G^3$, and $G^4$ is $CR^{13}$, one of $G^1$, $G^2$, $G^3$, and $G^4$ is C bonded to $R^4$, and the remaining two are selected from the group consisting of CH and $CR^{11}$;

Q is O, S, or $NR^{12}$;

$R^1$ and $R^2$ are independently H, OH, halo, CN, carboxyl, $NR^aR^b$, or a substituted or unsubstituted alkyl, alkoxy, or hydroxyalkyl group;

$R^3$ is a substituted or unsubstituted alkyl or cycloalkyl group;

$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;

$R^9$ and $R^{13}$ are independently H, halo, or a substituted or unsubstituted $C_1$-$C_6$ alkyl, or O—($C_1$-$C_6$ alkyl) group;

$R^{10}$ at each occurrence is independently halo, $CO_2R^c$, or a substituted or unsubstituted alkyl, alkoxy, hydroxyalkyl, cycloalkyl, or fluorinated cycloalkyl group;

$R^{11}$ at each occurrence OH, halo, $CF_3$, CN, carboxyl, $NR^aR^b$, or a substituted or unsubstituted alkyl, alkoxy group, or phenyl group;

$R^{12}$ is H or a substituted or unsubstituted $C_1$-$C_6$ alkyl group; and $R^a$ at each occurrence is independently H, or a substituted or unsubstituted alkyl, haloalkyl, cycloalkyl, aryl, or $SO_2$-alkyl group;

$R^b$ at each occurrence is H or a substituted or unsubstituted alkyl, or haloalkyl group;

$R^c$ is H or a substituted or unsubstituted alkyl, alkenyl, alkynyl, or cycloalkyl group;

n is 1, 2, 3, or 4; and r and t are each independently 1, 2, or 3.

2. The compound of claim 1, wherein t is 2 or 3.

3. The compound of claim 1, wherein $R^4$ is $CO_2H$, CN, $CONH_2$, $SO_2NH_2$, or a substituted or unsubstituted $CO_2$—$C_1$-$C_6$ alkyl, $CO_2$—$C_3$-$C_6$ cycloalkyl, CONH—$C_1$-$C_6$ alkyl, CONH—$C_3$-$C_6$ cycloalkyl, NH—$SO_2$—$C_1$-$C_6$ alkyl, or tetrazolyl group.

4. The compound of claim 3, wherein $R^4$ is $CO_2H$, CN, $CONH_2$, or a substituted or unsubstituted $CO_2$—$C_1$-$C_6$ alkyl, CONH—$C_1$-$C_6$ alkyl, or tetrazolyl group.

5. The compound of claim 3, wherein $R^4$ is $CO_2H$, $CONH_2$, or a tetrazolyl group.

6. The compound of claim 1 having the structure of Formula IA3:

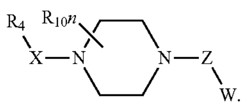

(IA3)

7. The compound of claim 1, wherein Z is a substituted or unsubstituted methylene.

8. The compound of claim 1, wherein W is

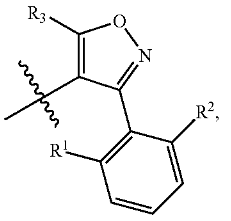

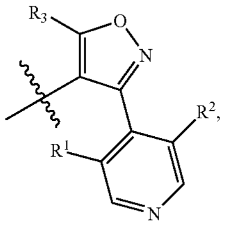

or

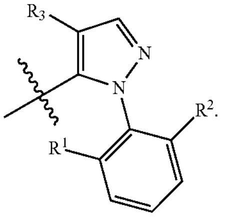

9. The compound of claim 1, wherein $R^1$ and $R^2$ are independently halo, CN, $CO_2R^e$, $NR^eR^f$, or a substituted or unsubstituted $C_1$-$C_6$ alkyl, $C_1$-$C_6$ alkoxy, or $C_1$-$C_6$ hydroxyalkyl group; and wherein $R^e$ and $R^f$ at each occurrence are independently H or a substituted or unsubstituted $C_1$-$C_6$ alkyl group.

10. The compound of claim 9, wherein $R^1$ and $R^2$ are independently H, F, Cl, CN, $CO_2H$, $NR^eR^f$, or a substituted or unsubstituted $C_1$-$C_3$ alkyl, $C_1$-$C_3$ alkoxy, or $C_1$-$C_3$ hydroxyalkyl group.

11. The compound of claim 1, wherein $R^1$ and $R^2$ are independently H, F, Cl, CN, $CO_2H$, $NH_2$, $CH_3$, $CH_2NH_2$, $OCF_3$, or $OCH_3$.

12. The compound of claim 1, wherein $R^1$ and $R^2$ are both Cl.

13. The compound of claim 1, wherein $R^3$ is a substituted or unsubstituted $C_1$-$C_6$ alkyl or $C_3$-$C_6$ cycloalkyl group.

14. The compound of claim 1, wherein $R^3$ is $CH_3$, $CH_2CH_3$, $CH(CH_3)_2$, $CH_2CH(CH_3)_2$, $CH(CH_2CH_3)_2$, $CH(CH_2CH_3)(CH_3)$, $C(CH_3)_3$, or cyclopropyl.

15. The compound of claim 1, wherein $R^3$ is an isopropyl or cyclopropyl group.

16. The compound of claim 1, wherein $R^{10}$ at each occurrence is independently halo, $CO_2R^c$, or a substituted or unsubstituted alkyl, alkoxy, hydroxyalkyl, cycloalkyl, or fluorinated cycloalkyl group.

17. The compound of claim 1 wherein X is

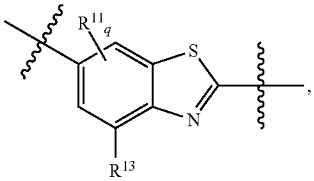

,

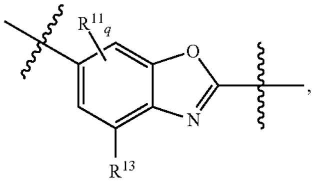

,

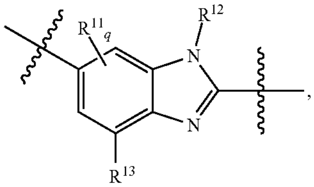

,

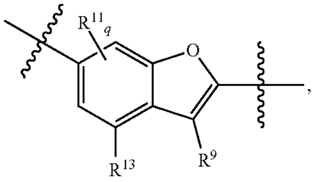

,

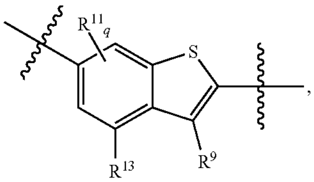

, or

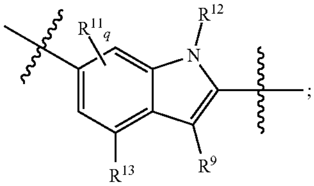

;

wherein q is 0, 1, or 2.

18. The compound of claim 1, wherein $R^{11}$ at each occurrence is independently halo, $CF_3$, or a substituted or unsubstituted alkyl, alkoxy, or phenyl group.

19. The compound of claim 1, wherein $R^{13}$ is H, F, or a substituted or unsubstituted $C_1$-$C_3$ alkyl, or O—($C_1$-$C_3$ alkyl) group.

20. The compound of claim 19, wherein $R^{13}$ is H, F, $CH_3$, or O—$CH_3$.

21. The compound of claim 1, wherein $R^9$ is H.

22. The compound of claim 17, wherein q is 1 and $R^{11}$ is $CH_3$ or F.

23. A composition comprising the compound of claim 1 and a pharmaceutically acceptable carrier.

24. A pharmaceutical composition comprising an effective amount of the compound of claim 1 for treating an FXR-mediated disorder or condition selected from the group consisting of liver disease and diabetes.

25. The pharmaceutical composition of claim 24 wherein the liver disease is selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

26. A method of treatment comprising administering an effective amount of a compound of claim 1 to a subject suffering from an FXR-mediated disorder or condition selected from the group consisting of liver disease and diabetes.

27. The method of claim 26, wherein the disorder or condition is liver disease and is selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

28. The compound of claim 6 wherein Z is unsubstituted methylene.

29. The compound of claim 28 wherein X is

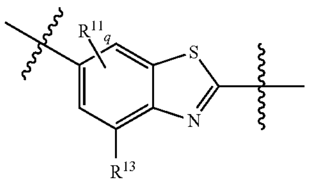

wherein q is 0.

30. The compound of claim 29 wherein W is

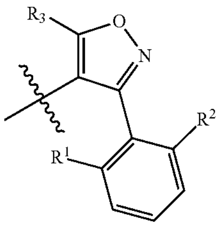

and $R^1$ and $R^2$ are both Cl.

31. The compound of claim 30 wherein $R^3$ is an isopropyl or cyclopropyl group.

32. The compound of claim 31 wherein $R^4$ is $CO_2H$, $CONH_2$, or a tetrazolyl group.

33. The compound of claim 32 wherein n is 1 or 2, and $R^{10}$ at each occurrence is independently an unsubstituted alkyl group.

* * * * *

UNITED STATES PATENT AND TRADEMARK OFFICE

CERTIFICATE OF CORRECTION

PATENT NO. : 10,919,903 B2
APPLICATION NO. : 16/346807
DATED : February 16, 2021
INVENTOR(S) : Xiaodong Xu It is certified that error appears in the above-identified patent and that said Letters Patent is hereby corrected as shown below:

In the Specification

Column 18, Line 25, should read:
In some embodiments of the present compounds, $R^1$ and $R^2$ are independently halo, CN, $CO_2H$, $NR^aR^b$, or a substituted or unsubstituted $C_1$-$C_6$ alkyl, $C_1$-$C_6$ alkoxy, or $C_1$-$C_6$ hydroxyalkyl group; and wherein $R^a$ and $R^b$ at each occurrence are independently H or a substituted or unsubstituted $C_1$-$C_6$ alkyl group. In some embodiments, $R^1$ and $R^2$ are independently H, F, Cl, CN, $CO_2H$, $NR^aR^b$, or a substituted or unsubstituted $C_1$-$C_3$ alkyl, $C_1$-$C_3$ alkoxy, or $C_1$-$C_3$ hydroxyalkyl group. In some embodiments, $R^1$ and $R^2$ are independently H, F, Cl, CN, $CO_2H$, $NH_2$, $CH_3$, $CH_2NH_2$, $OCF_3$, or $OCH_3$. In some embodiments, $R^1$ and $R^2$ are both Cl. In some embodiments, one of $R^1$ and $R^2$ is H and the other is $OCF_3$.

In the Claims

Claim 9, Column 97, Line 40, should read:
9. The compound of claim 1, wherein $R^1$ and $R^2$ are independently halo, CN, $CO_2H$, $NR^aR^b$, or a substituted or unsubstituted $C_1$-$C_6$ alkyl, $C_1$-$C_6$ alkoxy, or $C_1$-$C_6$ hydroxyalkyl group; and wherein $R^a$ and $R^b$ at each occurrence are independently H or a substituted or unsubstituted $C_1$-$C_6$ alkyl group.

Claim 10, Column 97, Line 46, should read:
10. The compound of claim 9, wherein $R^1$ and $R^2$ are independently H, F, Cl, CN, $CO_2H$, $NR^aR^b$, or a substituted or unsubstituted $C_1$-$C_3$ alkyl, $C_1$-$C_3$ alkoxy, or $C_1$-$C_3$ hydroxyalkyl group.

Signed and Sealed this
Twentieth Day of June, 2023

Katherine Kelly Vidal

Katherine Kelly Vidal
*Director of the United States Patent and Trademark Office*